(12) United States Patent
Coon et al.

(10) Patent No.: US 9,040,903 B2
(45) Date of Patent: May 26, 2015

(54) PRECURSOR SELECTION USING AN ARTIFICIAL INTELLIGENCE ALGORITHM INCREASES PROTEOMIC SAMPLE COVERAGE AND REPRODUCIBILITY

(75) Inventors: Joshua J. Coon, Middleton, WI (US); Michael S. Westphall, Fitchburg, WI (US); Graeme McAlister, Cambridge, MA (US); Derek Bailey, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 466 days.

(21) Appl. No.: 13/438,301

(22) Filed: Apr. 3, 2012

(65) Prior Publication Data
US 2012/0261568 A1    Oct. 18, 2012

Related U.S. Application Data

(60) Provisional application No. 61/471,464, filed on Apr. 4, 2011, provisional application No. 61/601,856, filed on Feb. 22, 2012.

(51) Int. Cl.
*B01D 59/44*    (2006.01)
*G06F 19/18*    (2011.01)
*H01J 49/00*    (2006.01)
*G06F 19/00*    (2011.01)

(52) U.S. Cl.
CPC .............. *G06F 19/18* (2013.01); *G06F 19/703* (2013.01); *H01J 49/0027* (2013.01); *H01J 49/004* (2013.01)

(58) Field of Classification Search
None
See application file for complete search history.

(56) References Cited

U.S. PATENT DOCUMENTS

| | | | |
|---|---|---|---|
| 6,057,543 A | 5/2000 | Vestal et al. | |
| 6,281,493 B1 | 8/2001 | Vestal et al. | |
| 6,489,610 B1 | 12/2002 | Barofsky et al. | |
| 6,541,765 B1 | 4/2003 | Vestal | |
| 6,570,153 B1 | 5/2003 | Li et al. | |
| 6,586,727 B2 | 7/2003 | Bateman et al. | |

(Continued)

FOREIGN PATENT DOCUMENTS

| | | |
|---|---|---|
| WO | 03/025576 | 3/2003 |
| WO | 2004/086050 | 10/2004 |

(Continued)

OTHER PUBLICATIONS

Addona et al. (2009) "Multi-Site Assessment of the Precision and Reproducibility of Multiple Reaction Monitoring-Based Measurements of Proteins in Plasma," Nature Biotechnology 27(7):633-641, and Online Methods, 3 pgs. Corrections, Nature Biotechnology 27(9):864.

(Continued)

*Primary Examiner* — Andrew Smyth
(74) *Attorney, Agent, or Firm* — Lathrop & Gage LLP

(57) ABSTRACT

Described herein are mass spectrometry systems and methods which utilize a dynamic new data acquisition/instrument control methodology. These systems and methods employ novel artificial intelligence algorithms to greatly increase quantitative and/or identification accuracy during data acquisition. In an embodiment, the algorithms can adapt the instrument methods and systems during data acquisition to direct data acquisition resources to increase quantitative or identification accuracy of target analytes, such as proteins, peptides, and peptide fragments.

21 Claims, 31 Drawing Sheets

(56) References Cited

U.S. PATENT DOCUMENTS

| | | | |
|---|---|---|---|
| 6,670,194 B1 | 12/2003 | Aebersold et al. | |
| 6,863,790 B1* | 3/2005 | Moini et al. | 204/452 |
| 6,940,065 B2 | 9/2005 | Graber et al. | |
| 7,195,751 B2 | 3/2007 | Pappin et al. | |
| 7,223,966 B2 | 5/2007 | Weiss et al. | |
| 7,534,622 B2 | 5/2009 | Hunt et al. | |
| 7,558,682 B2 | 7/2009 | Yamamoto | |
| 7,633,059 B2 | 12/2009 | Russ et al. | |
| 7,749,769 B2 | 7/2010 | Hunt et al. | |
| 7,755,036 B2 | 7/2010 | Satoh | |
| 7,884,318 B2* | 2/2011 | Milgram et al. | 250/282 |
| 7,928,361 B1 | 4/2011 | Whitehouse et al. | |
| 7,932,491 B2 | 4/2011 | Vestal | |
| 7,982,070 B2 | 7/2011 | Smith et al. | |
| 8,071,938 B2 | 12/2011 | Guharay | |
| 8,278,115 B2 | 10/2012 | Coon et al. | |
| 2002/0125423 A1* | 9/2002 | Ebeling et al. | 250/288 |
| 2002/0166961 A1* | 11/2002 | Berggren et al. | 250/288 |
| 2005/0147982 A1 | 7/2005 | Pappin et al. | |
| 2005/0148087 A1 | 7/2005 | Pappin et al. | |
| 2005/0153456 A1 | 7/2005 | Pappin | |
| 2006/0105416 A1 | 5/2006 | Pappin et al. | |
| 2006/0115871 A1 | 6/2006 | Bruce et al. | |
| 2006/0172319 A1 | 8/2006 | Yan et al. | |
| 2006/0255263 A1* | 11/2006 | Ishimaru et al. | 250/288 |
| 2007/0051886 A1* | 3/2007 | Rather | 250/288 |
| 2007/0054345 A1 | 3/2007 | Hunter | |
| 2007/0207555 A1 | 9/2007 | Guerra et al. | |
| 2007/0218560 A1 | 9/2007 | Pillai et al. | |
| 2008/0070314 A1 | 3/2008 | Geromanos et al. | |
| 2008/0087814 A1 | 4/2008 | Loucks | |
| 2008/0111068 A1* | 5/2008 | Zabrouskov | 250/282 |
| 2008/0113441 A1 | 5/2008 | Orlando et al. | |
| 2008/0149825 A1 | 6/2008 | Kozlovski et al. | |
| 2008/0203288 A1* | 8/2008 | Makarov et al. | 250/282 |
| 2008/0206737 A1 | 8/2008 | Hunter | |
| 2008/0272292 A1 | 11/2008 | Geromanos et al. | |
| 2009/0065686 A1 | 3/2009 | Shilov et al. | |
| 2009/0179147 A1* | 7/2009 | Milgram et al. | 250/282 |
| 2009/0194682 A1 | 8/2009 | Zhang et al. | |
| 2009/0283673 A1 | 11/2009 | Shilov et al. | |
| 2010/0227352 A1 | 9/2010 | Hunter | |
| 2010/0330680 A1 | 12/2010 | Frey et al. | |
| 2011/0111512 A1* | 5/2011 | Bystrom et al. | 436/86 |
| 2011/0121172 A1* | 5/2011 | Savitski et al. | 250/282 |
| 2011/0161273 A1* | 6/2011 | Nakayama et al. | 706/47 |
| 2011/0297823 A1 | 12/2011 | Coon et al. | |
| 2012/0022230 A1 | 1/2012 | Smith et al. | |
| 2012/0091330 A1 | 4/2012 | Coon et al. | |
| 2012/0158318 A1* | 6/2012 | Wright | 702/28 |
| 2012/0309040 A1* | 12/2012 | Madian et al. | 435/23 |
| 2013/0005050 A1* | 1/2013 | Zhang et al. | 436/501 |
| 2013/0035403 A1* | 2/2013 | Schaffer et al. | 514/777 |
| 2013/0084645 A1 | 4/2013 | Coon et al. | |

FOREIGN PATENT DOCUMENTS

| | | |
|---|---|---|
| WO | 2006/084130 | 8/2006 |
| WO | 2007/076606 | 7/2007 |
| WO | 2007/109292 | 9/2007 |
| WO | 2008/053399 | 5/2008 |
| WO | 2008/111911 | 9/2008 |
| WO | 2008/151207 | 12/2008 |
| WO | 2009/073505 | 6/2009 |

OTHER PUBLICATIONS

Ashburner et al. (2000) "Gene Ontology: Tool for the Unification of Biology," Nature Genetics 25(1):25-29.
Bailey et al. (2011) "How High Mass Accuracy Measurements Will Transform Targeted Proteomics," Proceedings of the 59th ASMS Conference on Mass Spectrometry and Allied Topics, (ASMS, Jun. 5-9, 2011, Denver, Colorado) ThOE:278.
Bakalarski et al. (2008) "The Impact of Peptide Abundance and Dynamic Range on Stable-Isotope-Based Quantitative Proteomic Analyses," J Proteome Res 7:4756-4765.
Baynes et al. (1990) "Iron Deficiency," Annu Rev Nutr 10:133-148.
Beausoleil et al. (2006) "A Probability-Based Approach for High-Throughput Protein Phosphorylation Analysis and Site Localization," Nat Biotechnol 24(10):1285-1292.
Belov et al. (2001) "Ion Discrimination During Ion Accumulation in a Quadrupole Interface External to a Fourier Transform Ion Cyclotron Resonance Mass Spectrometer," International Journal of Mass Spectrometry 208(1-3):205-225.
Bern et al. (2010) "Deconvolution of Mixture Spectra from Ion-Trap Data-Independent-Acquisition Tandem Mass Spectrometry," Analytical Chemistry 82(3):833-841.
Blackburn et al. (2010) "Improving Protein and Proteome Coverage Through Data-Independent Multiplexed Peptide Fragmentation," Journal of Proteome Research 9(7):3621-3637.
Busch, K. (2004) "Mass Spectrometry Forum—Space Charge in Mass Spectrometry," Spectroscopy 19(6):35-38.
Calvo et al. (2009) "Upstream Open Reading Frames Cause Widespread Reduction of Protein Expression and Are Polymorphic Among Humans," Proc Natl Acad Sci USA 106(18): 7507-7512.
Casey et al. (1988) "Iron-Responsive Elements: Regulatory RNA Sequences That Control mRNA Levels and Translation," Science 240(4854):924-928.
Chi et al. (2007) "Analysis of Phosphorylation Sites on Proteins from *Saccharomyces cerevisiae* by Electron Transfer Dissociation (ETD) Mass Spectrometry," Proc Natl Acad Sci USA 104(7):2193-2198.
Cox et al. (1995) "Mass Shifts and Local Space Charge Effects Observed in the Quadrupole Ion Trap at Higher Resolution," International Journal of Mass Spectrometry and Ion Processes 144(1-2):47-65.
Deutsch et al. (2008) "PeptideAtlas: A Resource for Target Selection for Emerging Targeted Proteomics Workflows," Embo Reports 9(5):429-434.
Dimauro et al. (2003) "Mitochondrial Respiratory-Chain Diseases," N Engl J Med 348(26):2656-2668.
Ducret et al. (1998) "High Throughput Protein Characterization by Automated Reverse-Phase Chromatography Electrospray Tandem Mass Spectrometry," Protein Science 7(3):706-719.
Duellman et al. (2009) "Phosphorylation Sites of Epstein-Barr Virus EBNA1 Regulate its Function," Journal of General Virology 90:2251-2259.
Duncan et al. (2009) "Quantifying Proteins by Mass Spectrometry: The Selectivity of SRM is Only Part of the Problem," Proteomics 9(5):1124-1127.
Eng et al. (1994) "An Approach to Correlate Tandem Mass Spectral Data of Peptides with Amino Acid Sequences in a Protein Database," J Am Soc Mass Spectrom 5(11):976-989.
Fusaro et al. (2009) "Prediction of High-Responding Peptides for Targeted Protein Assays by Mass Spectrometry," Nature Biotechnology 27(2):190-198.
Graumann et al. (2012) "A Framework for Intelligent Data Acquisition and Real-Time Database Searching for Shotgun Proteomics," Molecular & Cellular Proteomics 11(10.1074/mcp.M111.013185):1-11.
Grimsrud et al. (2010) "Large-Scale Phosphoprotein Analysis in *Medicago truncatula* Roots Provides Insight into in Vivo Kinase Activity in Legumes," Plant Physiology 152(1):19-28.
Grossmann et al. (2010) "Implementation and Evaluation of Relative and Absolute Quantification in Shotgun Proteomics with Label-Free Methods," Journal of Proteomics 73(9):1740-1746.
Gruhlert et al. (2005) "Quantitative Phosphoproteomics Applied to the Yeast Pheromone Signaling Pathway," Mol Cell Proteomics 4:310-327.
Gupta et al. (2009) "Combining Selected Reaction Monitoring with Discovery Proteomics in Limited Biological Samples," Proteomics 9(21):4834-4836.
Harscoat-Schiavo et al. (2010) "Modeling the Separation of Small Peptides by Cation-Exchange Chromatography," Journal of Separation Science 33(16):2447-2457.
Haubitz et al. (2009) "Identification and Validation of Urinary Biomarkers for Differential Diagnosis and Evaluation of Therapeutic

(56) References Cited

OTHER PUBLICATIONS

Intervention in Anti-neutrophil Cytoplasmic Antibody-Associated Vasculitis," Molecular & Cellular Proteomics 8(10):2296-2307.
Hoopmann et al. (2009) "Post Analysis Data Acquisition for the Iterative MS/MS Sampling of Proteomics Mixtures," J Proteome Res 8:1870-1875.
Huttlin et al. (2007) "Prediction of Error Associated with False Positive Rate Determination for Peptide Identification in Large-Scale Proteomics Experiments Using a Combined Reverse and Forward Peptide Sequence Database Strategy," Journal of Proteome Research 6(1):392-398.
Izrael-Tomasevic et al. (2009) "Targeting Interferon Alpha Subtypes in Serum: A Comparison of Analytical Approaches to the Detection and Quantitation of Proteins in Complex Biological Matrices," Journal of Proteome Research 8(6):3132-3140.
Jaffe et al. (2008) "Accurate Inclusion Mass Screening: A Bridge from Unbiased Discovery to Targeted Assay Development for Biomarker Verification," Molecular & Cellular Proteomics 7(10):1952-1962.
Kaplan et al. (2009) "Iron Acquisition and Transcriptional Regulation," Chem Rev 109(10):4536-4552.
Kennedy et al. (2008) "Use of Gas-Phase Fractionation to Increase Protein Identifications: Application to the Peroxisome," Methods Mol Biol 432:217-228.
Khidekel et al. (2007) "Probing the Dynamics of O-GlcNAc Glycosylation in the Brain Using Quantitative Proteomics," Nature Chemical Biology 3(6):339-348.
Kirkpatrick et al. (2005) "The Absolute Quantification Strategy: a General Procedure for the Quantification of Proteins and Post-Translational Modifications," Methods 35(3):265-273.
Kiyonami et al. (2011) "Increased Selectivity, Analytical Precision, and Throughput in Targeted Proteomics," Mol Cell Proteomics 10(10.1074/mcp.M110.002931):1-11.
Krokhin et al. (2004) "An Improved Model for Prediction of Retention Times of Tryptic Peptides in Ion Pair Reversed-Phase HPLC: Its Application to Protein Peptide Mapping by Off-Line HPLC-MALDI MS," Mol Cell Proteomics 3:908-919.
Krokhin, O.V. (2006) "Sequence-Specific Retention Calculator. Algorithm for Peptide Retention Prediction in Ion-Pair RP-HPLC: Application to 300-and 100-Å Pore Size C18 Sorbents," Analytical Chemistry 78(22):7785-7795.
Krokhin et al. (2006) "Use of Peptide Retention Time Prediction for Protein Identification by Off-Line Reversed-Phase HPLC-MALDI MS/MS," Analytical Chemistry 78(17):6265-6269.
Lange et al. (2008) "Selected Reaction Monitoring for Quantitative Proteomics: a Tutorial," Molecular Systems Biology 4:(222, 10.1038/msb.2008.61):1-14.
Lecchi et al. (2007) "Tandem Phosphorylation of Ser-911 and Thr-912 at the C Terminus of Yeast Plasma Membrane $H^+$-ATPase Leads to Glucose-Dependent Activation," Journal of Biological Chemistry 282(49):35471-35481.
Lee et al. (2011) "A Dynamic Model of Proteome Changes Reveals New Roles for Transcript Alteration in Yeast," Mol Syst Biol 7:(514, 10.1038/msb.2011.48):1-12.
Link et al. (1999) "Direct Analysis of Protein Complexes Using Mass Spectrometry," Nature Biotechnology 17(7):676-682.
Little et al. (1994) "Infrared Multiphoton Dissociation of Large Multiply-Charged Ions for Biomolecule Sequencing," Anal Chem 66:2809-2815.
Liu et al. (2004) "A Model for Random Sampling and Estimation of Relative Protein Abundance in Shotgun Proteomics," Analytical Chemistry 76(14):4193-4201.
Lowell et al. (2005) "Mitochondrial Dysfunction and Type 2 Diabetes," Science 307(5708):384-387.
Lu et al. (2007) "Absolute Protein Expression Profiling Estimates the Relative Contributions of Transcriptional and Translational Regulation," Nature Biotechnology 25(1):117-124.
Mallick et al. (2007) "Computational Prediction of Proteotypic Peptides for Quantitative Proteomics," Nature Biotechnology 25(1):125-131.

Mallick et al. (2010) "Proteomics: A Pragmatic Perspective," Nature Biotechnology 28(7):695-709.
Manning et al. (2002) "The Protein Kinase Complement of the Human Genome," Science 298(5600):1912-1934.
Marzolf et al. (2006) "SBEAMS-Microarray: Database Software Supporting Genomic Expression Analyses for Systems Biology," BMC Bioinformatics 7(286, 10.1186/1471-2105-7-286)):1-7.
Matallana-Surget et al. (2010) "Shotgun Proteomics: Concept, Key Points and Data Mining," Expert Review of Proteomics 7(1):5-7.
McAlister et al. (2007) "Implementation of Electron-Transfer Dissociation on a Hybrid Linear Ion Trap—Orbitrap Mass Spectrometer," Analytical Chemistry 79(10):3525-3534.
McAlister et al. (2008) "A Proteomics Grade Electron Transfer Dissociation-Enabled Hybrid Linear Ion Trap—Orbitrap Mass Spectrometer," Journal of Proteome Research 7(8):3127-3136.
McAlister et al. (2011) "Higher-Energy Collision-Activated Dissociation Without a Dedicated Collision Cell," Mol Cell Proteomics 10(10.1074/mcp.O111.009456):1-6.
McGivern et al. (2009) "Toward Defining the Phosphoproteome of *Xenopus laevis* Embryos," Developmental Dynamics 238(6):1433-1443.
Michalski et al. (2011) "Mass Spectrometry-Based Proteomics Using Q Exactive, a High-Performance Benchtop Quadrupole Orbitrap Mass Spectrometer," Mol Cell Proteomics 10(10.1074/mcp.M111.011015):1-11.
Mignone et al. (2002) "Untranslated Regions of mRNAs," Genome Biol 3(3, REVIEWS0004.1-0004.10):1-10.
Mignone et al. (2005) "UTRdb and UTRsite: A Collection of Sequences and Regulatory Motifs of the Untranslated Regions of Eukaryotic mRNAs," Nucleic Acids Res 33(Database issue):D141-D146.
Mootha et al. (2004) "Errα and Gabpa/b Specify PGC-1α-Dependent Oxidative Phosphorylation Gene Expression that is Altered in Diabetic Muscle," Proc Natl Acad Sci USA 101(17):6570-6575. Correction printed PNAS (2005) 102(29):10405.
Moritz et al. (2010) "Akt-RSK-S6-Kinase Signaling Networks Activated by Oncogenic Receptor Tyrosine Kinases," Science Signaling 3(136, ra64, 10.1126/2disignal.2000998): 1-19.
Murphy et al. (2000) "Origin of Mass Shifts in the Quadrupole Ion Trap: Dissociation of Fragile Ions Observed with a Hybrid Ion Trap/Mass Filter Instrument," Rapid Communications in Mass Spectrometry 14(4):270-273.
Nilsson et al. (2010) "Mass Spectrometry in High-Throughput Proteomics: Ready for the Big Time," Nat Methods 7(9):681-685.
Olsen et al. (2004) "Improved Peptide Identification in Proteomics by Two Consecutive Stages of Mass Spectrometric Fragmentation," P Natl Acad Sci USA 101(37):13417-13422.
Olsen et al. (2007) "Higher-Energy C-Trap Dissociation for Peptide Modification Analysis," Nat Methods 4(9):709-712.
Olsen et al. (2010) "Quantitative Phosphoproteomics Reveals Widespread Full Phosphorylation Site Occupancy During Mitosis," Science Signaling 3(104, ra3):1-15.
Oppermann et al. (2009) "Large-Scale Proteomics Analysis of the Human Kinome," Molecular & Cellular Proteomics 8(7):1751-1764.
Pagliarini et al. (2008) "A Mitochondrial Protein Compendium Elucidates Complex I Disease Biology," Cell 134(1):112-123.
Panchaud et al. (2009) "Precursor Acquisition Independent From Ion Count: How to Dive Deeper into the Proteomics Ocean," Analytical Chemistry 81(15):6481-6488.
Parker et al. (2010) "Mass-Spectrometry-Based Clinical Proteomics—a Review and Prospective," Analyst 135(8):1830-1838.
Pecqueur et al. (2001) "Uncoupling Protein 2, in Vivo Distribution, Induction Upon Oxidative Stress, and Evidence for Translational Regulation," J Biol Chem 276(12):8705-8712.
Perez-Martinez et al. (2003) "Mss51p Promotes Mitochondrial Cox1p Synthesis and Interacts with Newly Synthesized Cox1p," Embo J 22(21):5951-5961.
Perkins et al. (1999) "Probability-Based Protein Identification by Searching Sequence Databases Using Mass Spectrometry Data," Electrophoresis 20(18):3551-3567.
Phanstiel et al. (2008) "Mass Spectrometry Identifies and Quantifies 74 Unique Histone H4 Isoforms in Differentiating Human Embryonic Stem Cells," Proc Natl Acad Sci USA 105(11):4093-4098.

(56) References Cited

OTHER PUBLICATIONS

Phanstiel et al. (2009) "New Technology for the Large-Scale Proteomic Comparison of Human Embryonic Stem Cells, Induced Pluripotent Stem Cells, and Somatic Cells," Molecular & Cellular Proteomics MS.1:S11.
Phanstiel et al. (2009) "Peptide Quantification Using 8-Plex Isobaric Tags and Electron Transfer Dissociation Tandem Mass Spectrometry," Analytical Chemistry 81(4):1693-1698.
Phanstiel et al. (2011) "Proteomic and Phosphoproteomic Comparison of Human ES and iPS Cells," Nat Methods 8(10):821-830.
Picotti et al. (2007) "The Implications of Proteolytic Background for Shotgun Proteomics," Molecular & Cellular Proteomics 6(9):1589-1598.
Picotti et al. (2009) "Full Dynamic Range Proteome Analysis of *S. cerevisiae* by Targeted Proteomics," Cell 138(4):795-806.
Picotti et al. (2010) "High-Throughput Generation of Selected Reaction-Monitoring Assays for Proteins and Proteomes," Nature Methods 7(1): 43-48.
Piruat et al. (2005) "Oxygen Tension Regulates Mitochondrial DNA-Encoded Complex I Gene Expression," J Biol Chem 280(52):42676-42684.
Puig et al. (2005) "Coordinated Remodeling of Cellular Metabolism During Iron Deficiency Through Targeted mRNA Degradation," Cell 120(1):99-110.
Puigserver et al. (1998) "A Cold-Inducible Coactivator of Nuclear Receptors Linked to Adaptive Thermogenesis," Cell 92(6):829-839.
Rocher et al. (1998) "Study of Ghost Peaks Resulting from Space Charge and Non-Linear Fields in an Ion Trap Mass Spectrometer," Journal of Mass Spectrometry 33(10):921-935.
Rudomin et al. (2009) "Directed Sample Interrogation Utilizing an Accurate Mass Exclusion-Based Data-Dependent Acquisition Strategy (AMEx)," Journal of Proteome Research 8(6):3154-3160.
Sandhu et al. (2008) "Evaluation of Data-Dependent Versus Targeted Shotgun Proteomic Approaches for Monitoring Transcription Factor Expression in Breast Cancer," Journal of Proteome Research 7(4):1529-1541.
Scherl et al. (2008) "Genome-Specific Gas-Phase Fractionation Strategy for Improved Shotgun Proteomic Profiling of Proteotypic Peptides," Analytical Chemistry 80(4):1182-1191.
Schmidt et al. (2008) "An Integrated, Directed Mass Spectrometric Approach for In-Depth Characterization of Complex Peptide Mixtures," Molecular & Cellular Proteomics 7(11):2138-2150.
Schmidt et al. (2009) "Directed Mass Spectrometry: Towards Hypothesis-Driven Proteomics," Current Opinion in Chemical Biology 13(5-6):510-517.
Schroeder et al. (2004) "A Neutral Loss Activation Method for Improved Phosphopeptide Sequence Analysis by Quadrupole Ion Trap Mass Spectrometry," Anal Chem 76:3590-3598.
Second et al. (2009) "Dual-Pressure Linear Ion Trap Mass Spectrometer Improving the Analysis of Complex Protein Mixtures," Analytical Chemistry 81(18):7757-7765.
Sherman et al. (2009) "How Specific is My SRM?: The issue of Precursor and Product Ion Redundancy," Proteomics 9(5):1120-1123.
Storey et al. (2003) "Statistical Significance for Genomewide Studies," Proc Natl Acad Sci USA 100(16):9440-9445.
Swaney et al. (2007) "Supplemental Activation Method for High-Efficiency Electron-Transfer Dissociation of Doubly Protonated Peptide Precursors," Analytical Chemistry 79(2):477-485.
Swaney et al. (2008) "Decision Tree-Driven Tandem Mass Spectrometry for Shotgun Proteomics," Nature Methods 5(11):959-964.
Swaney et al. (2009) "Human Embryonic Stem Cell Phosphoproteome Revealed by Electron Transfer Dissociation Tandem Mass Spectrometry," Proc Natl Acad Sci USA 106(4)995-1000.
Syka et al. (2004) "Peptide and Protein Sequence Analysis by Electron Transfer Dissociation Mass Spectrometry," Proc Natl Acad Sci USA 101(26):9528-9533.
Tabb et al. (2010) "Repeatability and Reproducibility in Proteomic Identifications by Liquid Chromatography—Tandem Mass Spectrometry," Journal of Proteome Research 9(2):761-776.
Tang et al. (2006) "A Computational Approach Toward Label-Free Protein Quantification Using Predicted Peptide Detectability," Bioinformatics 22(14):E481-E488.
Tusher et al. (2001) "Significance Analysis of Microarrays Applied to the Ionizing Radiation Response," Proc Natl Acad Sci USA 98(9):5116-5121.
Venable et al. (2004) "Automated Approach for Quantitative Analysis of Complex Peptide Mixtures from Tandem Mass Spectra," Nature Methods 1(1):39-45.
Wallace, D.C. (2005) "A Mitochondrial Paradigm of Metabolic and Degenerative Diseases, Aging, and Cancer: A Dawn for Evolutionary Medicine," Annu Rev Genet 39:359-407.
Wang et al. (2010) "Comparison of Extensive Protein Fractionation and Repetitive LC-MS/MS Analyses on Depth of Analysis for Complex Proteomes," Journal of Proteome Research 9(2):1032-1040.
Washburn et al. (2001) "Large-Scale Analysis of the Yeast Proteome by Multidimensional Protein Identification Technology," Nat Biotechnol 19:242-247.
Webb-Robertson et al. (2008) "A Support Vector Machine Model for the Prediction of Proteotypic Peptides for Accurate Mass and Time Proteomics," Bioinformatics 24(13):1503-1509.
Wenger et al. (2010) "Sub-Part-Per-Million Precursor and Product Mass Accuracy for High-Throughput Proteomics on an Electron Transfer Dissociation-Enabled Orbitrap Mass Spectrometer," Molecular & Cellular Proteomics 9(5):754-763.
Wenger et al. (2011) "Gas-Phase Purification Enables Accurate, Multiplexed Proteome Quantification with Isobaric Tagging," Nat Methods 8(11):933-937.
Wienkoop et al. (2006) "Relative and Absolute Quantitative Shotgun Proteomics: Targeting Low-Abundance Proteins in *Arabidopsis thaliana*," Journal of Experimental Botany 57(7):1529-1535.
Williams et al. (2007) "Dual Electrospray Ion Source for Electron-Transfer Dissociation on a Hybrid Linear Ion Trap—Orbitrap Mass Spectrometer," Analytical Chemistry 79:7916-7919.
Wisniewski et al. (2009) "Universal Sample Preparation Method for Proteome Analysis," Nature Methods 6(5):359-362.
Wu et al. (2002) "Shotgun Proteomics: Tools for the Analysis of Complex Biological Systems," Current Opinion in Molecular Therapeutics 4(3):242-250.
Wu et al. (2003) "A Method for the Comprehensive Proteomic Analysis of Membrane Proteins," Nature Biotechnology 21(5):532-538.
Wu et al. (2004) "Metabolic Labeling of Mammalian Organisms with Stable Isotopes for Quantitative Proteomic Analysis," Analytical Chemistry 76(17):4951-4959.
Xiao et al. (2010) "Global Phosphorylation Analysis of β-Arrestin-Mediated Signaling Downstream of a Seven Transmembrane Receptor (7TMR)," Proc Natl Acad Sci USA 107(34):15299-15304.
Yan et al. (2011) "Index-Ion Triggered MS2 Ion Quantification: A Novel Proteomics Approach for Reproducible Detection and Quantification of Targeted Proteins in Complex Mixtures," Mol Cell Proteomics 10(3, 10.1074/mcp.M110.005611):1-15.
Yang et al. (2009) "MRM Screening/Biomarker Discovery with Linear Ion Trap MS: A Library of Human Cancer-Specific Peptides," BMC Cancer 9(96):1-11.
Zerck et al. (2009) "An Iterative Strategy for Precursor Ion Selection for LC-MS/MS Based Shotgun Proteomics," Journal of Proteome Research 8(7):3239-3251.
Zhang et al. (2010) "A Robust Error Model for iTRAQ Quantification Reveals Divergent Signaling Between Oncogenic FLT3 Mutants in Acute Myeloid Leukemia," Mol Cell Proteomics 9(5):780-790.

\* cited by examiner

|   | Protein | | mRNA | |
|---|---|---|---|---|
| n | # | % | # | % |
| 1 | 3061 | 100.0 | 1931 | 100.0 |
| 2 | 2089 | 68.2 | 1897 | 98.2 |
| 3 | 1640 | 53.6 | 1881 | 97.4 |
| 4 | 1270 | 41.5 | 1867 | 96.7 |
| 5 | 954 | 31.2 | 1841 | 95.3 |

Figure 1

Expected OrbiQ Performance Specifications

| Scan rate | 10 Hz @ 10,000 resolving power |
|---|---|
| Mass accuracy<br>   $MS^1$<br>   $MS^2$ | < 5 ppm with external calibration<br>< 2 ppm with internal calibration |
| Isolation width | ± 0.2 $m/z$ |
| Dynamic range<br>   intrascan<br>   interscan | > 15,000<br>> 500,000 |
| Sensitivity (SRM mode) | Neat sample on column < 25 amol<br>in complex mixture > 50 amol |

Figure 8

| Q-Exactive | PSMs by OMSSA at 1% FDR | | | |
| --- | --- | --- | --- | --- |
| | Data Dependent | | inSeq Targeted | |
| AQUA Peptides (2 fmol) | 1 | 2 | 1 | 2 |
| GVSAFSTWEk (SEQ ID NO:15) | 0 | 0 | 10 √ | 7 √ |
| TVFSSTQLCVLNDr (SEQ ID NO:10) | 1 | 1 | 19 √ | 16 √ |
| EGQLAAGTCEIVTLDr (SEQ ID NO:63) | 0 | 0 | 12 √ | 8 √ |
| HFLTLAPIk (SEQ ID NO:62) | 0 | 0 | 7 √ | 0 √ |
| SEDEDEDGDATr (SEQ ID NO:59) | 0 | 0 | 3 √ | 0 √ |
| LWSLAEIATSDLk (SEQ ID NO:64) | 0 | 0 | 0 √ | 1 √ |
| HTGTPLGDIPYGk (SEQ ID NO:60) | 0 | 0 | 4 √ | 6 √ |
| FSDLTEEEFr (SEQ ID NO:61) | 0 | 0 | 8 √ | 4 √ |
| SGWTCTQPGGr (SEQ ID NO:65) (Not Targeted) | 1 | 1 | 0 | 0 |
| LEQNPEESQDIk (SEQ ID NO:66) (Not Targeted) | 1 | 0 | 0 | 0 |

Order in which LC-MS/MS runs were conducted: 1. inSeq, 2. DDA, 3. DDA, 4. inSeq    √ detected with PRM

Figure 24 inSeq: Instant Sequence Confirmation

Step 1: Construct a list of peptide targets (from previous DDA experiments) and sort them by their elution order (CEO)

| ID | Sequence | CEO | z | Target with PRM |
|---|---|---|---|---|
| PE715 | RPEYFITANDVK (SEQ ID NO:67) | 28.373 | z=2 | |
| PE716 | KADNIYIEEIK (SEQ ID NO:68) | 28.349 | z=2 | |
| PE717 | STSKEDLIASIDSK (SEQ ID NO:69) | 28.262 | z=2 | |
| PE718 | AAQLGFNTACVEK (SEQ ID NO:70) | 28.420 | z=2 | |
| PE719 | FVIGGPQGDAGLTGRK (SEQ ID NO:71) | 28.411 | z=3 | |
| PE720 | SVEPVVVIDGK (SEQ ID NO:72) | 28.508 | z=2 | |
| PE721 | HTGTPLGDIPYGK (SEQ ID NO:80) | 28.508 | z=2 | YES ← 8 of these AQUA targets in the full list |
| PE722 | LSNPSGGWGVPR (SEQ ID NO:73) | 28.828 | z=3 | |
| PE723 | YGSANVEGTILK (SEQ ID NO:74) | 28.422 | z=2 | |
| PE724 | VDEGSDVLNTWKK (SEQ ID NO:75) | 28.422 | z=3 | |
| PE725 | TATYDGEEGILAAK (SEQ ID NO:76) | 28.375 | z=2 | |
| PE726 | TSNGEPFWSGAK (SEQ ID NO:77) | 28.559 | z=2 | |
| PE727 | LPLQDVYK (SEQ ID NO:78) | 28.564 | z=2 | |
| PE728 | AIANGQVDGFPTQEECR (SEQ ID NO:79) | 29.113 | z=2,3 | |
| PE729 | TTVEFTGESLR (SEQ ID NO:80) | 28.517 | z=2 | | n = 6,428

Figure 25

SEQUENCE LISTING

```
<160> NUMBER OF SEQ ID NOS: 81

<210> SEQ ID NO 1
<211> LENGTH: 17
<212> TYPE: PRT
<213> ORGANISM: Artificial sequence
<220> FEATURE:
<223> OTHER INFORMATION: Synthetic peptide

<400> SEQUENCE: 1

Ile Glu Glu Leu Asp Gln Glu Asn Glu Ala Ala Leu Glu Asn Gly Ile
1               5                   10                  15

Lys

<210> SEQ ID NO 2
<211> LENGTH: 15
<212> TYPE: PRT
<213> ORGANISM: Artificial sequence
<220> FEATURE:
<223> OTHER INFORMATION: Synthetic peptide

<400> SEQUENCE: 2

Arg Asn Ser Ser Glu Ala Ser Ser Gly Asp Phe Leu Asp Leu Lys
1               5                   10                  15

<210> SEQ ID NO 3
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 3

Phe Cys Ala Asp His Pro Phe Leu Phe Phe Ile Arg
1               5                   10

<210> SEQ ID NO 4
<211> LENGTH: 9
<212> TYPE: PRT
<213> ORGANISM: Artificial sequence
<220> FEATURE:
<223> OTHER INFORMATION: Synthetic peptide

<400> SEQUENCE: 4

Ala Pro Cys Gln Ala Gly Asp Leu Arg
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic peptide

<400> SEQUENCE: 5

Phe Ser Asp Leu Thr Glu Glu Glu Phe Arg
1               5                   10

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Thr Leu Asn Gly Ile Gln Leu Ala Arg
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Gly Ala Leu Asp Gly Glu Ala Pro Arg
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide

<400> SEQUENCE: 8

Ala Glu Thr Leu Val Gln Ala Arg
1               5

<210> SEQ ID NO 9
<211> LENGTH: 16
<212> TYPE: PRT
<213> ORGANISM: Artificial sequence
<220> FEATURE:
<223> OTHER INFORMATION: Synthetic peptide

<400> SEQUENCE: 9
```

```
Ser Glu Ala Ser Ser Pro Pro Trp Thr Ser Ser His Ser Arg
1               5                   10                  15

<210> SEQ ID NO 10
<211> LENGTH: 14
<212> TYPE: PRT
<213> ORGANISM: Artificial sequence
<220> FEATURE:
<223> OTHER INFORMATION: Synthetic peptide

<400> SEQUENCE: 10

Thr Val Phe Ser Ser Thr Gln Leu Cys Val Leu Asn Asp Arg
1               5                   10

<210> SEQ ID NO 11
<211> LENGTH: 16
<212> TYPE: PRT
<213> ORGANISM: Artificial sequence
<220> FEATURE:
<223> OTHER INFORMATION: Synthetic peptide

<400> SEQUENCE: 11

Glu Gly Gln Leu Ala Ala Gly Thr Cys Glu Ile Val Thr Leu Asp Arg
1               5                   10                  15

<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Asp Ile Gln Phe Gly Ser Gln Ile Lys
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic peptide

<400> SEQUENCE: 13

Ser Phe Glu Gly Thr Asp Tyr Gly Lys
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Trp Pro Gly Tyr Leu Asn Gly Gly Arg
1               5

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15
```

```
Gly Val Ser Ala Phe Ser Thr Trp Glu Lys
1               5                   10

<210> SEQ ID NO 16
<211> LENGTH: 8
<212> TYPE: PRT
<213> ORGANISM: Artificial sequence
<220> FEATURE:
<223> OTHER INFORMATION: Synthetic peptide

<400> SEQUENCE: 16

Phe Ser Glu Val Ser Ala Asp Lys
1               5

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Asn Ser Trp Gly Thr Asp Trp Gly Glu Lys
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic peptide

<400> SEQUENCE: 18

Ala Ala Ala Ser Ala Asn Glu Ser Glu Arg Leu Leu Asp Lys
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic peptide

<400> SEQUENCE: 19

Ser Gly Ala Thr Ala Tyr Ile Tyr Lys Ala Gln Ser Ser Lys
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20

Arg Gln Ser Met Val Glu Ala Ala Ala Glu Asn Leu Arg
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic peptide

<400> SEQUENCE: 21

Gly Trp Phe Pro Gln Asn Phe Gly Arg Pro Leu Arg
```

```
1               5                   10
```

<210> SEQ ID NO 22
<211> LENGTH: 13
<212> TYPE: PRT
<213> ORGANISM: Artificial sequence
<220> FEATURE:
<223> OTHER INFORMATION: Synthetic peptide

<400> SEQUENCE: 22

```
Ser Tyr Val Ile Asp Val Asn Gly Phe Ser Phe Val Lys
1               5                   10
```

<210> SEQ ID NO 23
<211> LENGTH: 11
<212> TYPE: PRT
<213> ORGANISM: Artificial sequence
<220> FEATURE:
<223> OTHER INFORMATION: Synthetic peptide

<400> SEQUENCE: 23

```
Leu Tyr Tyr Asp Leu Asp Thr Ile Arg Phe Arg
1               5                   10
```

<210> SEQ ID NO 24
<211> LENGTH: 11
<212> TYPE: PRT
<213> ORGANISM: Artificial sequence
<220> FEATURE:
<223> OTHER INFORMATION: Synthetic peptide

<400> SEQUENCE: 24

```
Leu Asn Phe Asn Asp His Phe Trp Leu Leu Arg
1               5                   10
```

<210> SEQ ID NO 25
<211> LENGTH: 12
<212> TYPE: PRT
<213> ORGANISM: Artificial sequence
<220> FEATURE:
<223> OTHER INFORMATION: Synthetic peptide

<400> SEQUENCE: 25

```
Ala Leu Ala Tyr Asn Phe Trp Pro Ser Leu His Arg
1               5                   10
```

<210> SEQ ID NO 26
<211> LENGTH: 13
<212> TYPE: PRT
<213> ORGANISM: Artificial sequence
<220> FEATURE:
<223> OTHER INFORMATION: Synthetic peptide

<400> SEQUENCE: 26

```
Asn Leu Thr Asp Glu Val Trp Ala Val Lys Asp Gly Lys
1               5                   10
```

<210> SEQ ID NO 27
<211> LENGTH: 13
<212> TYPE: PRT
<213> ORGANISM: Artificial sequence
<220> FEATURE:
<223> OTHER INFORMATION: Synthetic peptide

<400> SEQUENCE: 27

```
Leu Pro Asn Ser Asn Val Asn Ile Glu Phe Ala Thr Arg
1               5                   10
```

```
<210> SEQ ID NO 28
<211> LENGTH: 12
<212> TYPE: PRT
<213> ORGANISM: Artificial sequence
<220> FEATURE:
<223> OTHER INFORMATION: Synthetic peptide

<400> SEQUENCE: 28

Glu Thr Asp Leu Asn Gly Trp Ile Lys Asp Lys Arg
1               5                   10

<210> SEQ ID NO 29
<211> LENGTH: 13
<212> TYPE: PRT
<213> ORGANISM: Artificial sequence
<220> FEATURE:
<223> OTHER INFORMATION: Synthetic peptide

<400> SEQUENCE: 29

Gln Phe Glu Thr Gly Thr His Ser Lys Val Val Asn Lys
1               5                   10

<210> SEQ ID NO 30
<211> LENGTH: 13
<212> TYPE: PRT
<213> ORGANISM: Artificial sequence
<220> FEATURE:
<223> OTHER INFORMATION: Synthetic peptide

<400> SEQUENCE: 30

Thr Asn Val Asn Val Pro Asn Val Phe Ile Asp Asp Lys
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic peptide

<400> SEQUENCE: 31

Lys Gly Leu Phe Phe Ser Glu Arg Asp Phe Thr Lys
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic peptide

<400> SEQUENCE: 32

Glu Thr Cys Gln Gly Leu Lys Phe Leu His Asn Lys
1               5                   10

<210> SEQ ID NO 33
<211> LENGTH: 12
<212> TYPE: PRT
<213> ORGANISM: Artificial sequence
<220> FEATURE:
<223> OTHER INFORMATION: Synthetic peptide

<400> SEQUENCE: 33

Glu Trp Ser Met Ile Lys Ser Leu Ser His Thr Arg
1               5                   10
```

```
<210> SEQ ID NO 34
<211> LENGTH: 11
<212> TYPE: PRT
<213> ORGANISM: Artificial sequence
<220> FEATURE:
<223> OTHER INFORMATION: Synthetic peptide

<400> SEQUENCE: 34

Leu Val Ala Phe Asn Arg Tyr Ile Cys Tyr Arg
1               5                   10

<210> SEQ ID NO 35
<211> LENGTH: 11
<212> TYPE: PRT
<213> ORGANISM: Artificial sequence
<220> FEATURE:
<223> OTHER INFORMATION: Synthetic peptide

<400> SEQUENCE: 35

Leu Phe Gln Asn Phe Gln Leu Val Tyr Phe Arg
1               5                   10

<210> SEQ ID NO 36
<211> LENGTH: 13
<212> TYPE: PRT
<213> ORGANISM: Artificial sequence
<220> FEATURE:
<223> OTHER INFORMATION: Synthetic peptide

<400> SEQUENCE: 36

Asn Ile Asp Thr Ile Ile Pro Phe Ile Asp Asp Ala Lys
1               5                   10

<210> SEQ ID NO 37
<211> LENGTH: 7
<212> TYPE: PRT
<213> ORGANISM: Artificial sequence
<220> FEATURE:
<223> OTHER INFORMATION: Synthetic peptide

<400> SEQUENCE: 37

Asp Arg Thr Pro Pro Pro Arg
1               5

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Ala Ala Asp Glu Ser Glu Arg
1               5

<210> SEQ ID NO 39
<211> LENGTH: 10
<212> TYPE: PRT
<213> ORGANISM: Artificial sequence
<220> FEATURE:
<223> OTHER INFORMATION: Synthetic peptide

<400> SEQUENCE: 39

Ala His Ala His Leu Asp Thr Gly Arg Arg
1               5                   10
```

```
<210> SEQ ID NO 40
<211> LENGTH: 8
<212> TYPE: PRT
<213> ORGANISM: Artificial sequence
<220> FEATURE:
<223> OTHER INFORMATION: Synthetic peptide

<400> SEQUENCE: 40

Ala Phe Leu Ile Glu Glu Gln Lys
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic peptide

<400> SEQUENCE: 41

Val Gln Glu Val Leu Leu Lys
1               5

<210> SEQ ID NO 42
<211> LENGTH: 6
<212> TYPE: PRT
<213> ORGANISM: Artificial sequence
<220> FEATURE:
<223> OTHER INFORMATION: Synthetic peptide

<400> SEQUENCE: 42

Leu Val Leu Ile Asn Lys
1               5

<210> SEQ ID NO 43
<211> LENGTH: 12
<212> TYPE: PRT
<213> ORGANISM: Artificial sequence
<220> FEATURE:
<223> OTHER INFORMATION: Synthetic peptide

<400> SEQUENCE: 43

Gly Val Ala Ile Asn Met Val Thr Glu Glu Asp Lys
1               5                   10

<210> SEQ ID NO 44
<211> LENGTH: 14
<212> TYPE: PRT
<213> ORGANISM: Artificial sequence
<220> FEATURE:
<223> OTHER INFORMATION: Synthetic peptide

<400> SEQUENCE: 44

Asn Val Val Leu Pro Thr Glu Thr Glu Val Ala Pro Ala Lys
1               5                   10

<210> SEQ ID NO 45
<211> LENGTH: 14
<212> TYPE: PRT
<213> ORGANISM: Artificial sequence
<220> FEATURE:
<223> OTHER INFORMATION: Synthetic peptide

<400> SEQUENCE: 45

Ala Gly Gly Ile Glu Thr Ile Ala Asn Glu Tyr Ser Asp Arg
1               5                   10

<210> SEQ ID NO 46
```

```
<211> LENGTH: 11
<212> TYPE: PRT
<213> ORGANISM: Artificial sequence
<220> FEATURE:
<223> OTHER INFORMATION: Synthetic peptide

<400> SEQUENCE: 46

Phe Asn Thr Ser Asp Val Ser Ala Ile Glu Lys
1               5                   10

<210> SEQ ID NO 47
<211> LENGTH: 7
<212> TYPE: PRT
<213> ORGANISM: Artificial sequence
<220> FEATURE:
<223> OTHER INFORMATION: Synthetic peptide

<400> SEQUENCE: 47

Arg Gln Pro Ala Pro Pro Arg
1               5

<210> SEQ ID NO 48
<211> LENGTH: 9
<212> TYPE: PRT
<213> ORGANISM: Artificial sequence
<220> FEATURE:
<223> OTHER INFORMATION: Synthetic peptide

<400> SEQUENCE: 48

Ala His Ala His Leu Asp Thr Gly Arg
1               5

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Val Pro Ala Ile Asn Val Asn Asp Ser Val Thr Lys
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic peptide

<400> SEQUENCE: 50

Ala Ile Val Asn Val Ile Gly Met His Lys
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic peptide

<400> SEQUENCE: 51

Ile Asp Glu Met Pro Glu Ala Ala Val Lys
1               5                   10

<210> SEQ ID NO 52
<211> LENGTH: 6
```

```
<212> TYPE: PRT
<213> ORGANISM: Artificial sequence
<220> FEATURE:
<223> OTHER INFORMATION: Synthetic peptide

<400> SEQUENCE: 52

Ala Phe Asn Leu Val Lys
1               5

<210> SEQ ID NO 53
<211> LENGTH: 13
<212> TYPE: PRT
<213> ORGANISM: Artificial sequence
<220> FEATURE:
<223> OTHER INFORMATION: Synthetic peptide

<400> SEQUENCE: 53

Ala Asn Leu Val Leu Leu Ser Gly Ala Asn Glu Gly Lys
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Thr Val Ile Ile Glu Gln Ser Trp Gly Ser Pro Lys
1               5                   10

<210> SEQ ID NO 55
<211> LENGTH: 10
<212> TYPE: PRT
<213> ORGANISM: Artificial sequence
<220> FEATURE:
<223> OTHER INFORMATION: Synthetic peptide

<400> SEQUENCE: 55

Lys Ile Glu Phe Pro Leu Pro Asp Glu Lys
1               5                   10

<210> SEQ ID NO 56
<211> LENGTH: 11
<212> TYPE: PRT
<213> ORGANISM: Artificial sequence
<220> FEATURE:
<223> OTHER INFORMATION: Synthetic peptide

<400> SEQUENCE: 56

Ile His Val Phe Tyr Ile Asp Tyr Gly Asn Arg
1               5                   10

<210> SEQ ID NO 57
<211> LENGTH: 20
<212> TYPE: PRT
<213> ORGANISM: Artificial sequence
<220> FEATURE:
<223> OTHER INFORMATION: Synthetic peptide

<400> SEQUENCE: 57

Phe Thr Ala Ser Ala Gly Ile Gln Val Val Gly Asp Asp Leu Thr Val
1               5                   10                  15

Thr Asn Pro Lys
            20
```

```
<210> SEQ ID NO 58
<211> LENGTH: 18
<212> TYPE: PRT
<213> ORGANISM: Artificial sequence
<220> FEATURE:
<223> OTHER INFORMATION: Synthetic peptide

<400> SEQUENCE: 58

Ala Ala Val Glu Gly Thr Val Glu Ala Gly Ala Thr Val Glu Ser Thr
1               5                   10                  15
Ala Cys

<210> SEQ ID NO 59
<211> LENGTH: 12
<212> TYPE: PRT
<213> ORGANISM: Artificial sequence
<220> FEATURE:
<223> OTHER INFORMATION: Synthetic peptide

<400> SEQUENCE: 59

Ser Glu Asp Glu Asp Glu Asp Gly Asp Ala Thr Arg
1               5                   10

<210> SEQ ID NO 60
<211> LENGTH: 13
<212> TYPE: PRT
<213> ORGANISM: Artificial sequence
<220> FEATURE:
<223> OTHER INFORMATION: Synthetic peptide

<400> SEQUENCE: 60

His Thr Gly Thr Pro Leu Gly Asp Ile Pro Tyr Gly Lys
1               5                   10

<210> SEQ ID NO 61
<211> LENGTH: 10
<212> TYPE: PRT
<213> ORGANISM: Artificial sequence
<220> FEATURE:
<223> OTHER INFORMATION: Synthetic peptide

<400> SEQUENCE: 61

Phe Ser Asp Leu Thr Glu Glu Glu Phe Arg
1               5                   10

<210> SEQ ID NO 62
<211> LENGTH: 9
<212> TYPE: PRT
<213> ORGANISM: Artificial sequence
<220> FEATURE:
<223> OTHER INFORMATION: Synthetic peptide

<400> SEQUENCE: 62

His Phe Leu Thr Leu Ala Pro Ile Lys
1               5

<210> SEQ ID NO 63
<211> LENGTH: 16
<212> TYPE: PRT
<213> ORGANISM: Artificial sequence
<220> FEATURE:
<223> OTHER INFORMATION: Synthetic peptide

<400> SEQUENCE: 63

Glu Gly Gln Leu Ala Ala Gly Thr Cys Glu Ile Val Thr Leu Asp Arg
1               5                   10                  15
```

```
<210> SEQ ID NO 64
<211> LENGTH: 13
<212> TYPE: PRT
<213> ORGANISM: Artificial sequence
<220> FEATURE:
<223> OTHER INFORMATION: Synthetic peptide

<400> SEQUENCE: 64

Leu Trp Ser Leu Ala Glu Ile Ala Thr Ser Asp Leu Lys
1               5                   10

<210> SEQ ID NO 65
<211> LENGTH: 11
<212> TYPE: PRT
<213> ORGANISM: Artificial sequence
<220> FEATURE:
<223> OTHER INFORMATION: Synthetic peptide

<400> SEQUENCE: 65

Ser Gly Trp Thr Cys Thr Gln Pro Gly Gly Arg
1               5                   10

<210> SEQ ID NO 66
<211> LENGTH: 12
<212> TYPE: PRT
<213> ORGANISM: Artificial sequence
<220> FEATURE:
<223> OTHER INFORMATION: Synthetic peptide

<400> SEQUENCE: 66

Leu Glu Gln Asn Pro Glu Glu Ser Gln Asp Ile Lys
1               5                   10

<210> SEQ ID NO 67
<211> LENGTH: 12
<212> TYPE: PRT
<213> ORGANISM: Artificial sequence
<220> FEATURE:
<223> OTHER INFORMATION: Synthetic peptide

<400> SEQUENCE: 67

Arg Pro Glu Tyr Phe Ile Thr Ala Asn Asp Val Lys
1               5                   10

<210> SEQ ID NO 68
<211> LENGTH: 11
<212> TYPE: PRT
<213> ORGANISM: Artificial sequence
<220> FEATURE:
<223> OTHER INFORMATION: Synthetic peptide

<400> SEQUENCE: 68

Lys Ala Asp Asn Ile Tyr Ile Glu Glu Ile Lys
1               5                   10

<210> SEQ ID NO 69
<211> LENGTH: 14
<212> TYPE: PRT
<213> ORGANISM: Artificial sequence
<220> FEATURE:
<223> OTHER INFORMATION: Synthetic peptide

<400> SEQUENCE: 69

Ser Thr Ser Lys Glu Asp Leu Ile Ala Ser Ile Asp Ser Lys
1               5                   10
```

<210> SEQ ID NO 70
<211> LENGTH: 13
<212> TYPE: PRT
<213> ORGANISM: Artificial sequence
<220> FEATURE:
<223> OTHER INFORMATION: Synthetic peptide

<400> SEQUENCE: 70

Ala Ala Gln Leu Gly Phe Asn Thr Ala Cys Val Glu Lys
1               5                   10

<210> SEQ ID NO 71
<211> LENGTH: 16
<212> TYPE: PRT
<213> ORGANISM: Artificial sequence
<220> FEATURE:
<223> OTHER INFORMATION: Synthetic peptide

<400> SEQUENCE: 71

Phe Val Ile Gly Gly Pro Gln Gly Asp Ala Gly Leu Thr Gly Arg Lys
1               5                   10                  15

<210> SEQ ID NO 72
<211> LENGTH: 11
<212> TYPE: PRT
<213> ORGANISM: Artificial sequence
<220> FEATURE:
<223> OTHER INFORMATION: Synthetic peptide

<400> SEQUENCE: 72

Ser Val Glu Pro Val Val Val Ile Asp Gly Lys
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic peptide

<400> SEQUENCE: 73

Leu Ser Asn Pro Ser Gly Gly Trp Gly Val Pro Arg
1               5                   10

<210> SEQ ID NO 74
<211> LENGTH: 12
<212> TYPE: PRT
<213> ORGANISM: Artificial sequence
<220> FEATURE:
<223> OTHER INFORMATION: Synthetic peptide

<400> SEQUENCE: 74

Tyr Gly Ser Ala Asn Val Glu Gly Thr Ile Leu Lys
1               5                   10

<210> SEQ ID NO 75
<211> LENGTH: 13
<212> TYPE: PRT
<213> ORGANISM: Artificial sequence
<220> FEATURE:
<223> OTHER INFORMATION: Synthetic peptide

<400> SEQUENCE: 75

Val Asp Glu Gly Ser Asp Val Leu Asn Thr Trp Lys Lys
1               5                   10

<210> SEQ ID NO 76

```
<211> LENGTH: 14
<212> TYPE: PRT
<213> ORGANISM: Artificial sequence
<220> FEATURE:
<223> OTHER INFORMATION: Synthetic peptide

<400> SEQUENCE: 76

Thr Ala Thr Tyr Asp Gly Glu Glu Gly Ile Leu Ala Ala Lys
1               5                   10

<210> SEQ ID NO 77
<211> LENGTH: 12
<212> TYPE: PRT
<213> ORGANISM: Artificial sequence
<220> FEATURE:
<223> OTHER INFORMATION: Synthetic peptide

<400> SEQUENCE: 77

Thr Ser Asn Gly Glu Pro Phe Trp Ser Gly Ala Lys
1               5                   10

<210> SEQ ID NO 78
<211> LENGTH: 8
<212> TYPE: PRT
<213> ORGANISM: Artificial sequence
<220> FEATURE:
<223> OTHER INFORMATION: Synthetic peptide

<400> SEQUENCE: 78

Leu Pro Leu Gln Asp Val Tyr Lys
1               5

<210> SEQ ID NO 79
<211> LENGTH: 17
<212> TYPE: PRT
<213> ORGANISM: Artificial sequence
<220> FEATURE:
<223> OTHER INFORMATION: Synthetic peptide

<400> SEQUENCE: 79

Ala Ile Ala Asn Gly Gln Val Asp Gly Phe Pro Thr Gln Glu Glu Cys
1               5                   10                  15

Arg

<210> SEQ ID NO 80
<211> LENGTH: 11
<212> TYPE: PRT
<213> ORGANISM: Artificial sequence
<220> FEATURE:
<223> OTHER INFORMATION: Synthetic peptide

<400> SEQUENCE: 80

Thr Thr Val Glu Phe Thr Gly Glu Ser Leu Arg
1               5                   10

<210> SEQ ID NO 81
<211> LENGTH: 14
<212> TYPE: PRT
<213> ORGANISM: Artificial sequence
<220> FEATURE:
<223> OTHER INFORMATION: Synthetic peptide

<400> SEQUENCE: 81

Thr His Thr Gly Thr Pro Leu Gly Asp Ile Pro Tyr Gly Lys
1               5                   10
```

PRECURSOR SELECTION USING AN ARTIFICIAL INTELLIGENCE ALGORITHM INCREASES PROTEOMIC SAMPLE COVERAGE AND REPRODUCIBILITY

CROSS REFERENCE TO RELATED APPLICATIONS

This application claims the benefit of and priority under 35 U.S.C. 119(e) to U.S. Provisional Application 61/471,464 filed on Apr. 4, 2011 and U.S. Provisional Application 61/601,856 filed on Feb. 22, 2012, both entitled "Precursor Selection Using an Artificial Intelligence Algorithm Increases Proteomic Sample Coverage and Reproducibility", both of which are hereby incorporated by reference in their entirety.

STATEMENT REGARDING FEDERALLY SPONSORED RESEARCH OR DEVELOPMENT

This invention was made with government support under GM080148 awarded by the National Institutes of Health. The government has certain rights in the invention.

BACKGROUND

The ability to identify proteins and determine their chemical structures has become central to the life sciences. The amino acid sequence of proteins provides a link between proteins and their coding genes via the genetic code, and, in principle, a link between cell physiology and genetics. The identification of proteins provides a window into complex cellular regulatory networks.

Ion trap mass spectrometers are among the most widely used platforms for molecular analysis—spanning natural products, to pharmaceuticals, to biologics such as proteins. Most mass spectrometer-based experiments begin with the isolation of a group of compounds from a set of samples through some sort of extraction technique, e.g., proteins from tissues, cell lysates, or fluids followed by proteolytic digestion of those proteins into peptides (i.e., bottom-up proteomics). Frequently, but not necessarily, the mass spectrometers are then coupled with some form of separations, e.g., electrophoretic or chromatographic. Over the course of just a few hours, mass spectral instruments can autonomously interrogate tens of thousands of molecular species via tandem mass spectrometry.

Quantitative analysis in chemistry is the determination of the absolute or relative abundance of one, several, or all particular substance(s) present in a sample. For biological samples, quantitative analysis performed via mass spectrometry can determine the relative abundance of peptides and proteins. The accepted methodology for performing mass spectrometric quantitation is accomplished using a mass spectrometer capable of MS/MS fragmentation (i.e., triple quadropole or ion trap). The quantitation process can involve isobaric tagging of peptide precursors, which when combined with post-acquisition software, provides the relative abundance of peptides. However, when a peptide precursor is selected for tandem mass spectrometry, there are often interfering species with similar mass-to-charge ratios that are co-isolated and subjected to activation. These species are often other isobarically tagged peptides with different relative quantitation, which therefore disturb the quantitative measurement of the peptide of interest.

Isobaric labeling is an important quantitative method as it allows for multiplexing and is directly applicable to clinical samples. A significant source of error, however, occurs when another eluting peptide ion has a m/z value that is very near that of the selected precursor (~50%, in our hands). The result is the isolation of both species, which are consequently co-dissociated, to produce a composite MS/MS spectrum. The resulting reporter ion ratios do not accurately reflect the relative abundances of either peptide; limiting both the precision and dynamic range of quantitation, as the median peptide ratio is close to 1:1.

The increasing popularity of iTRAQ for quantitative proteomics applications has spurred increased efforts to evaluate its relevance, accuracy, and precision for biological interpretation. Recently, some researchers have begun to assess the accuracy and precision of iTRAQ quantification as well as drawbacks which hinder the applicability and attainable dynamic range of iTRAQ. Some results suggest that crosstalk between interfering factors can result in underestimations. [Ow et al., "iTRAQ Underestimation in Simple and Complex Mixtures: 'The Good, the Bad and the Ugly'", Journal of Proteome Research, web publication Sep. 16, 2009]. It is clear that there is tantalizing potential for iTRAQ and other protein labeling methods to provide accurate quantification spanning several orders of magnitude. This potential can be limited, however, by several factors. First, for example, the existence of isotopic impurities often requires correction of mass spectral data to provide accurate quantitation which currently requires the availability of accurate isotopic factors. Second, the interference of mixed MS/MS contribution occurring during precursor selection is a problem that is currently very difficult to minimize.

Protein identification technologies have rapidly matured such that constructing catalogs of the thousands of proteins comprised by a cell using mass spectrometry (MS) is now relatively straightforward [de Godoy, L. M. F. et al. Nature 455, 1251-1255 (2008); Swaney, D. L., Wenger, C. D. & Coon, J. J. J. Proteome Res. 9, 1323-1329 (2010)]. Knowing how the abundance of these molecules change under various circumstances is not [Ong, S. E. & Mann, M. Nat. Chem. Biol. 1, 252-262 (2005)]. Stable isotope labeling by amino acids in cell culture (SILAC) provides a means to make binary or ternary comparisons [Jiang, H. & English, A. M. J. Proteome Res. 1, 345-350 (2002); Ong, S. E. et al. Mol. Cell. Proteomics 1, 376-386 (2002)]. By interlacing these two- or three-way experiments, higher-order comparisons can be obtained [Olsen, J. V. et al. Sci. Signal. 3, ra3 (2010)]. Such large-scale multiplexed experiments are invaluable, as they (1) allow measurement of time-course experiments, (2) permit collection of biological replicates, and (3) enable direct comparison of transcriptomic and proteomic data.

Constructing this type of multi-faceted proteomics study, however, is an arduous undertaking and has only been accomplished in a handful of experiments by an even smaller group of researchers. The first impediment is the requirement to grow multiple groups of cells with various labels. And this step is actually less limiting than the second major obstacle: each binary or ternary set must be analyzed separately. When combined with the need for extensive pre-MS fractionation and technical replicates, a large-scale experiment via SILAC demands three to six months of constant instrument usage.

As proteomics moves away from discovery based experiments towards hypothesis driven analyses, the measure of success is no longer the absolute number of proteins identified, but the identification of specific proteins of interest. This trend is exemplified in the surge of interest in selected reaction monitoring (SRM) based protein assays—a powerful tandem mass spectrometry method that can be used to monitor target peptides within a complex protein digest. These experiments typically entail careful optimization of fragmentation parameters, tight regulation of liquid chromatography (LC) conditions, and complex method scheduling. To date, in every mass spectrometer based protein assay, the spectrometer has been a passive agent. The user instructs the instrument on how to survey the precursor ion population, which precursors to interrogate, and how to interrogate those precursors. Essentially, the instruments require careful and detailed administration by the user, requiring laborious methods to produce sensitive, specific, and reproducible results.

SUMMARY

Described herein are mass spectrometry systems and methods which utilize a dynamic a new data acquisition/instrument control methodology. These systems and methods employ novel artificial intelligence algorithms to greatly increase quantitative and/or identification accuracy during data acquisition. In an embodiment, the algorithms can adapt the instrument methods and systems during data acquisition to direct data acquisition resources to increase quantitative or identification accuracy of target analytes, such as proteins, peptides, and peptide fragments.

In an embodiment, a method of identifying or quantifying an analyte in a sample using mass spectrometry is provided, the method comprising:
(a) providing a list of target analytes and target analyte product information, wherein the list comprises from 25 to 5,000,000 target analytes, optionally between 25 to 1,000,000 target analytes, optionally between 50 to 100,000 target analytes, optionally between 50 to 10,000 target analytes, optionally greater than 50, optionally greater than 100, optionally greater than 500, optionally greater than 1000, optionally greater than 1500, optionally from 100 to 5000, optionally from 200 to 2500, optionally from 500 to 2500;
(b) providing a sample containing an analyte;
(c) generating a distribution of precursor analyte ions from the sample;
(d) fragmenting precursor analyte ions having a preselected distribution of mass-to-charge ratios, thereby generating product ions;
(e) measuring the mass-to-charge ratios of at least a portion of the product ions in a mass analyzer, wherein the mass analyzer has a mass accuracy of at least 100 ppm, optionally 1000 ppm, optionally 200 ppm, optionally 80 ppm, optionally 50 ppm, optionally 10 ppm, optionally 5 ppm, optionally from 5 to 1000 ppm, from 5 to 250 ppm, optionally from 5 to 100 ppm, optionally from 5 to 50 ppm, optionally from 5 to 25 ppm, thereby generating product ion mass spectrometry data; and
(f) optimizing analyte identification or quantitation during data acquisition by comparing the product ion mass spectrometry data to the list of target analytes and target analyte product information;
thereby identifying or quantifying an analyte in the sample using mass spectrometry.

The systems and methods provided herein are especially useful in the context of protein, peptide and peptide fragment analysis. In an embodiment, for example, the method is provided wherein:
the list of target analytes and target analyte product information comprises target peptides and target peptide product information corresponding to one or more proteins;
the analyte comprises peptides corresponding to proteins;
the step of (d) fragmenting precursor analyte ions having a preselected distribution of mass-to-charge ratios, thereby generating product ions; comprises fragmenting precursor peptide ions having a preselected distribution of mass-to-charge ratios, thereby generating product ions; and
the step of (f) optimizing analyte identification or quantitation during data acquisition by comparing the product ion mass spectrometry data to the list of target analytes and target analyte product information; comprises optimizing peptide or protein identification or quantitation during data acquisition by comparing the product ion mass spectrometry data to the list of target analytes and target analyte product information comprising target peptides and target peptide product information corresponding to one or more proteins.

In an embodiment, the method further comprises: identifying target peptide product information in the product ion mass spectrometry data corresponding to a target peptide, thereby identifying a target peptide; and removing the identified target peptide from the list of target peptides and target peptide product information corresponding to one or more proteins during data acquisition.

In an embodiment, the method further comprises: removing the identified target peptide product information from the list of target peptides and target peptide product information corresponding to one or more proteins during data acquisition.

In an embodiment, the method further comprises: identifying one or more target peptides corresponding to a single protein, thereby identifying a target protein; and
removing all the identified target peptides and peptide product information from the list of target peptides and target peptide product information corresponding to one or more proteins which correspond to the identified protein during data acquisition.

In an embodiment, the method further comprises: adding target peptides and target peptide product information to the list of target peptides and target peptide product information corresponding to one or more proteins during data acquisition.

In an embodiment, the target analyte product information comprises the masses of the target analytes or target analyte products. In another embodiment, the target peptide product information comprises the masses of the target peptides or target peptide products.

In an embodiment, the method further comprises: calculating a chromatography column elution order of the peptides in the list of target peptides and target peptide product information corresponding to one or more proteins, thereby generating an elution order list;
sorting the elution order list from first eluting peptide to last eluting peptide, thereby generating a sorted elution order list;
fractionating the sample with a chromatography column prior to generating a distribution of precursor peptide ions from the sample;
identifying target peptide product information in the product ion mass spectrometry data corresponding to a target peptide, thereby identifying a target peptide;
comparing the identified target peptide to the sorted elution order list during data acquisition; and
identifying one or more target peptides from the sorted elution order list which are within X peptides of the identified peptide, wherein X is equal to 20% of the total number of target peptides in the elution order list, thereby generating a list of next predicted eluting peptides.

In an embodiment, the method further comprises: identifying one or more peptides in the list of next predicted eluting peptides during data acquisition;

selecting a range of mass-to-charge ratios of precursor ions corresponding to the one or more peptides in the list of next predicted eluting peptides; and
measuring the mass-to-charge ratios of the range of mass-to-charge ratios corresponding to the one or more peptides in the list of next predicted eluting peptides, thereby generating precursor mass spectrometry data.

In an embodiment, the method further comprises: identifying one or more peptides in the list of next predicted eluting peptides during data acquisition;
wherein in step (d), the precursor peptide ions having a preselected distribution of mass-to-charge ratios correspond to the one or more peptides in the list of next predicted eluting peptides.

In an embodiment, the method further comprises: measuring the mass-to-charge ratios of a range of mass-to-charge ratios corresponding to the distribution of precursor peptide ions, thereby generating precursor mass spectrometry data;
determining a signal-to-noise ratio of two or more peaks in the precursor mass spectrometry data corresponding to one or more peptides in the list of target peptides and target peptide product information corresponding to one or more proteins, during data acquisition; wherein at least one of the two or more peaks in the precursor mass spectrometry data corresponding to one or more peptides corresponds to a labeled protein and at least one corresponds to an un-labeled protein; and
repeating steps (c)-(f) if the signal-to-noise ratio of the least intense of the two or more peaks in the precursor mass spectrometry data corresponding to one or more peptides in the list of target peptides and target peptide product information corresponding to one or more proteins is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the method further comprises: identifying target peptide product information in the product ion mass spectrometry data corresponding to a target protein, thereby identifying a target protein;
determining a signal-to-noise ratio of one or more peaks in the product ion mass spectrometry data corresponding to a sequence tag of the identified target protein during data acquisition; and
repeating steps (c)-(f) if the signal-to-noise ratio of one or more peaks in the product ion mass spectrometry data corresponding to a sequence tag of an identified target protein is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the method further comprises: identifying target peptide product information in the product ion mass spectrometry data corresponding to a target protein, thereby identifying a target protein;
determining a signal-to-noise ratio of one or more peaks in the product ion mass spectrometry data corresponding to a reporter tag of the identified target protein during data acquisition; and
repeating steps (c)-(f) if the signal-to-noise ratio of one or more peaks in the product ion mass spectrometry data corresponding to a reporter tag of an identified target protein is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the method further comprises: selecting a target peptide having one or more sites of post-translational modification;
comparing the product ion mass spectrometry data to the list of target peptides and target peptide product information corresponding to one or more proteins to determine if the sites of the target peptide having one or more post-translational modifications can be uniquely identified; and
adjusting a fragmentation parameter during data acquisition until sites of the target peptide having the one or more post-translational modifications can be uniquely identified;
wherein the fragmentation parameter corresponds to a fragmentation pressure, gas, electron energy, wavelength of electromagnetic radiation, power of electromagnetic radiation, illumination time of electromagnetic radiation, flux of electromagnetic radiation, total dose of electromagnetic radiation, collision energy, or reaction time.

In an embodiment, the method further comprises: selecting a target peptide having one or more sites of post-translational modification;
comparing the product ion mass spectrometry data to the list of target peptides and target peptide product information corresponding to one or more proteins to determine if the sites of the target peptide having one or more post-translational modifications can be uniquely identified; and
adjusting a fragmentation method during data acquisition until sites of the target peptide having the one or more post-translational modifications can be uniquely identified;
wherein the fragmentation method is beam-type collision activated dissociation, ion reaction dissociation, electron reaction dissociation, electron transfer dissociation, electron capture dissociation, neutral reaction dissociation, laser-induced dissociation, surface induced dissociation, or resonant excitation collision activated dissociation.

In an embodiment, the method further comprises: selecting a target peptide having one or more sites of post-translational modification;
identifying peaks in the product ion mass spectrometry data which correspond to the target peptide having one or more sites of post-translational modification;
comparing the product ion mass spectrometry data to the list of target peptides and target peptide product information corresponding to one or more proteins during data acquisition to determine if the sites of the target peptide having one or more post-translational modifications can be uniquely identified; and
repeating steps (c)-(f) until sites of the target peptide having the one or more post-translational modifications can be uniquely identified.

The systems and methods described herein are especially useful in the context of isobaric or isotopic label-based analysis. In an embodiment, for example, a method of identifying or quantifying an analyte in a sample using mass spectrometry is provided, wherein the proteins are isobarically labeled proteins. In an embodiment, a method of identifying or quantifying an analyte in a sample using mass spectrometry is provided, wherein the proteins or peptides are isotopically labeled proteins or peptides or isotopically coded proteins or peptides. In an aspect, the proteins or peptides are phosphorylated proteins or peptides. In another aspect, the proteins or peptides are co-translationally modified proteins or peptides. In a further aspect, the proteins or peptides are post-translationally modified proteins or peptides. In an aspect, the proteins are indicative of a disease state.

In an embodiment, the method further comprises: identifying target analyte product information in the product ion mass spectrometry data corresponding to a target analyte, thereby identifying a target analyte; and
removing the identified target analyte from the list of target analytes and target analyte product information during data acquisition.

In an embodiment, the method further comprises: removing the identified target analyte product information from the list of target analytes and target analyte product information during data acquisition.

In an embodiment, the method further comprises: identifying one or more target analytes corresponding to a single analyte, thereby identifying a target analyte; and
removing all the identified target analytes and analyte product information from the list of target analytes and target analyte product information which correspond to the identified analyte, during data acquisition.

In an embodiment, the method further comprises: adding target analytes and target analyte product information to the list of target analytes and target analyte product information during data acquisition.

In an embodiment, the method further comprises: calculating a chromatography column elution order of the analyte in the list of target analytes and target analyte product information, thereby generating an elution order list;
sorting the elution order list from first eluting analyte to last eluting analyte, thereby generating a sorted elution order list;
fractionating the sample with a chromatography column prior to generating a distribution of precursor analyte ions from the sample;
identifying target analyte product information in the product ion mass spectrometry data corresponding to a target analyte, thereby identifying a target analyte;
comparing the identified target analyte to the sorted elution order list during data acquisition; and
identifying one or more target analytes from the sorted elution order list which are within X analytes of the identified analyte, wherein X is equal to 20% of the total number of target analytes in the elution order list, thereby generating a list of next predicted eluting analytes.

In an embodiment, the method further comprises: identifying one or more analytes in the list of next predicted eluting analytes during data acquisition;
selecting a range of mass-to-charge ratios of precursor ions corresponding to the one or more analytes in the list of next predicted eluting analytes; and
measuring the mass-to-charge ratios of the range of mass-to-charge ratios corresponding to the one or more analytes in the list of next predicted eluting analytes, thereby generating precursor mass spectrometry data.

In an embodiment, the method further comprises: identifying one or more analytes in the list of next predicted eluting analytes during data acquisition; wherein in step (d), the precursor analyte ions having a preselected distribution of mass-to-charge ratios correspond to the one or more analytes in the list of next predicted eluting analytes.

In an embodiment, the method further comprises: identifying one or more analytes in the list of next predicted eluting analytes during data acquisition; selecting a range of mass-to-charge ratios of precursor ions corresponding to the one or more analytes in the list of next predicted eluting analytes; fragmenting precursor ions having mass-to-charge ratios within the selected range of mass-to-charge ratios; and measuring the mass-to-charge ratios of the fragmented precursor ions, thereby generating product ion mass spectrometry data.

In an embodiment, the method further comprises: measuring the mass-to-charge ratios of a range of mass-to-charge ratios corresponding to the distribution of precursor analyte ions, thereby generating precursor mass spectrometry data;
determining a signal-to-noise ratio of two or more peaks in the precursor mass spectrometry data corresponding to one or more analytes in the list of target analytes and target analyte product information, during data acquisition; wherein at least one of the two or more peaks in the precursor mass spectrometry data corresponding to one or more analytes corresponds to a labeled analyte and at least one corresponds to an unlabeled analyte; and
repeating steps (c)-(f) if the signal-to-noise ratio of the least intense of the two or more peaks in the precursor mass spectrometry data corresponding to one or more analytes in the list of target analytes and target analyte product information is less than two-to-one, optionally three-to-one, optionally five-to-one, optionally ten-to-one, optionally twenty-to-one, optionally between two-to-one and twenty-to-one, optionally between five-to-one and twenty-to-one.

In a further embodiment, the method further comprises using mass spectrometry data from the precursor analyte ions to optimize analyte detection. For example, data from a $MS^1$ scan can be used in addition to the product ion mass spectrometry data collected during a $MS^2$ scan. Mass spectrometry data measured from precursor analyte ions can be compared to the list of target analytes which can also contain target analyte precursor ion information and landmark precursor ion signal information. "Target analyte precursor ion information" refers to one or more measured attributes of the precursor analyte ions selected from the group including, but not limited to, mass, signal intensity, mass-to-charge ratio, charge state, signal to noise ratio, and combinations thereof. "Landmark precursor ion signal information" refers to desired attributes of ion mass spectrometry data which may not correspond to only one specific target analyte.

Thus, in an embodiment, the method further comprises:
measuring mass-to-charge ratios of at least a portion of the distribution of precursor analyte ions, thereby generating precursor analyte ion mass spectrometry data; and
optimizing analyte identification or quantitation during data acquisition by comparing the precursor analyte ion mass spectrometry data to the list of target analytes and target analyte product information, wherein said list further comprises target analyte precursor ion information and landmark precursor ion signal information.

Alternatively, the mass spectrometry data from the precursor analyte ions could be used instead of the product mass spectrometry data to optimize analyte detection. Thus, in an embodiment, the method comprises:
(a) providing a list of target analytes, target analyte precursor ion information and landmark precursor ion signal information, wherein the list comprises from 25 to 5,000,000 target analytes;
(b) providing a sample containing an analyte;
(c) generating a distribution of precursor analyte ions from the sample;
(d) measuring mass-to-charge ratios of at least a portion of the distribution of precursor analyte ions in a mass analyzer, wherein the mass analyzer has a mass accuracy of at least 1000 ppm, thereby generating precursor analyte ion mass spectrometry data; and
(e) optimizing analyte identification or quantitation during data acquisition by comparing the precursor analyte ion mass spectrometry data to the list of target analytes, target analyte precursor ion information and landmark precursor ion signal information;
thereby identifying or quantifying an analyte in the sample using mass spectrometry.

In an embodiment, a method of identifying or quantifying an analyte in a sample using mass spectrometry is provided, the method comprising:
(a) providing a list of target peptides, wherein the target list comprises from 25 to 5,000,000 target peptides;
(b) calculating a chromatography column elution order and elution time of the peptides in the list of target peptides, thereby generating an elution order list and predicted elution times for each target peptide;
(c) sorting the elution order list from first eluting peptide to last eluting peptide, thereby generating a sorted elution order list;
(d) providing a sample containing an analyte, wherein said analyte comprises peptides corresponding to one or more proteins;
(e) generating a distribution of precursor analyte ions from the sample at elution times corresponding to the predicted elution times for the target peptides, wherein said analyte ions comprises peptide ions;
(f) fragmenting precursor analyte ions having a preselected distribution of mass-to-charge ratios from at least a portion of the distribution of precursor analyte ions, thereby generating product ions;
(g) measuring the mass-to-charge ratios of at least a portion of the product ions collected in a mass analyzer, wherein the mass analyzer has a mass accuracy of at least 100 ppm, optionally a mass accuracy of at least 1000 ppm, thereby generating product ion mass spectrometry data; and
(h) identifying target peptides or peptide product information in the product ion mass spectrometry data corresponding to a target peptide by comparing the product ion mass spectrometry data to the list of target peptides and target peptide product information,
thereby identifying or quantifying an analyte in the sample using mass spectrometry. Optionally, the list comprises 25 to 1,000,000 target peptides, 50 to 100,000 target peptides, or optionally between 50 to 10,000 target peptides, optionally greater than 50, optionally greater than 100, optionally greater than 500, optionally greater than 1000, optionally greater than 1500, optionally from 100 to 5000, optionally from 200 to 2500, or optionally from 500 to 2500.

In an embodiment, the method further comprises comparing the elution time of the identified target peptides or peptide product information to the sorted elution order list and predicted elution times during data acquisition. In an embodiment, the method further comprises performing one or more data dependent acquisition scans to determine current elution time and comparing the determined elution time to the sorted elution order list and predicted elution times during data acquisition. In an embodiment, the method further comprises performing one or more data dependent acquisition scans comprising:
generating a second distribution of precursor analyte ions from the sample, wherein the elution times of the second distribution of precursor analyte ions do not correlate to the predicted elution times for the target peptides;
fragmenting precursor analyte ions from at least a portion of the second distribution of precursor analyte ions, thereby generating a second set of product ions; and
measuring the mass-to-charge ratios of the second set of product ions, thereby generating data dependent product ion mass spectrometry data.

In an embodiment, the method further provides that in step (f), the precursor peptide ions having a preselected distribution of mass-to-charge ratios correspond to the one or more peptides in the list of next predicted eluting peptides.

In an embodiment, the method further comprises:
(i) identifying one or more peptides in the sorted elution list as peptides predicted to elute next during data acquisition;
(j) selecting a range of mass-to-charge ratios of precursor ions corresponding to the one or more peptides predicted to elute next; and
(k) measuring the mass-to-charge ratios of the range of mass-to-charge ratios corresponding to the one or more peptides predicted to elute next, thereby generating precursor mass spectrometry data.

In an embodiment, the target peptide product information comprises the masses of the target peptides or target peptide products.

In an embodiment, a method of identifying or quantifying an analyte in a sample using mass spectrometry is provided, the method comprising:
(a) generating a sequencing queue containing a MS1 scan to be performed and one or more mass spectrometry scans to be performed, wherein said mass spectrometry scans to be performed in the sequencing queue correlate to analyte ion peaks having a predicted elution time, and said MS1 scan is not associated with an elution time;
(b) generating a real-time heap queue containing one or more target scans to be performed, wherein said target scans to be performed correlate to peptides or target peptides having a predicted elution time, wherein any time a new mass spectrometry scan or target scan is to be performed, target scans in the real-time heap queue are performed ahead of any mass spectrometry scans from the sequencing queue;
(c) providing a sample containing an analyte;
(d) performing the MS1 scan when no other scans are present in the sequencing queue or real-time heap queue, wherein performing the MS1 scan comprises generating a distribution of precursor analyte ions from the sample and measuring mass-to-charge ratios of at least a portion of the product ions in a mass analyzer, thereby generating one or more analyte ion peaks;
(e) selecting one or more analyte ion peaks, generating a new mass spectrometry scan corresponding to each of the selected analyte ion peaks, and adding the new mass spectrometry scan into the sequencing queue;
(f) performing one or more mass spectrometry scans from the sequencing queue, wherein mass spectrometry scans added more recently to the sequencing queue are performed after mass spectrometry scans added earlier to the sequencing queue, wherein performing one or more mass spectrometry scans comprises:
  (i) fragmenting precursor analyte ions having a preselected distribution of mass-to-charge ratios, thereby generating product ions;
  (ii) measuring the mass-to-charge ratios of at least a portion of the product ions in a mass analyzer, thereby generating product ion mass spectrometry data;
(g) identifying a target analyte from the product ion mass spectrometry data, calculating an elution time for the target analyte, generating a new target scan corresponding to the target analyte and calculated elution time, and adding the new target scan into the real-time heap queue;
(h) performing one or more target scans from the real-time heap queue, wherein target scans are performed at elution times corresponding to the calculated elution times for the target analytes, wherein performing one or more target scans comprises:
  (i) fragmenting precursor analyte ions having a preselected distribution of mass-to-charge ratios, thereby generating product ions;

(ii) measuring the mass-to-charge ratios of at least a portion of the product ions in the mass analyzer, thereby generating product ion mass spectrometry data; and
(i) comparing product ion mass spectrometry data to a list of target analytes and target analyte product information;
thereby identifying or quantifying an analyte in the sample using mass spectrometry. In an embodiment, the method further comprising comparing elution time of performed target scans to calculated elution times during data acquisition, thereby tracking current elution time of the experiment.

In an embodiment, the target analyte product information comprises the masses of the target analytes or target analyte products.

In the systems and methods described herein, the mass-to-charge ratios of multiple product ions are optionally measure simultaneously. Additionally, the multiple product ions are optionally generated from different precursor analyte ions.

The systems and methods described herein are especially useful in the context of isobaric or isotopic label-based analysis. In an embodiment, for example, a method of identifying or quantifying an analyte in a sample using mass spectrometry is provided, wherein the analyte is an isobarically labeled analyte. In an aspect, the analyte is an isotopically labeled analyte or isotopically coded analyte.

In a related embodiment, the analyte comprises one or more small molecules, pharmaceutical compounds, oligonucleotides, or sugars. In an embodiment, the method further comprises digesting the one or more proteins. In an embodiment, the distribution of precursor analyte ions is generated by an electrospray ionization source or a MALDI source. In another embodiment, the method is implemented in a tandem mass spectrometer instrument, a multistage mass spectrometer instrument, or a hybrid mass spectrometer instrument.

In an embodiment, a mass spectrometer system for analyzing an analyte is provided, the system comprising:
an ion source for generating ions from the analyte;
first ion separation optics in communication with the ion source for separating ions according to their mass-to-charge ratios;
ion fragmentation optics in communication with the first ion separation optics for generating product ions;
a mass analyzer in communication with the ion fragmentation optics for separating ions according to their mass-to-charge ratios; wherein the mass analyzer comprises an ion detector for detecting ions separated according to their mass-to-charge ratios;
a controller operably connected to the first and second ion separation optics, the first ion detector, and the ion fragmentation optics; wherein the controller comprises a memory module;
wherein the controller controls the memory module, ion optics, mass analyzer and detector so as to:
(a) receive a list of target analytes and target analyte product information into the memory module, wherein the list comprises from 25 to 5,000,000 target analytes, 25 to 1,000,000 target analytes; optionally between 50 to 100,000 target analytes, or optionally between 50 to 10,000 target peptides;
(b) provide a sample containing an analyte;
(c) generate a distribution of precursor analyte ions from the sample;
(d) fragment precursor analyte ions having a preselected distribution of mass-to-charge ratios, thereby generating product ions;
(e) measure the mass-to-charge ratios of at least a portion of the product ions in the mass analyzer, wherein the mass analyzer has a mass accuracy of at least 100 ppm, optionally a mass accuracy of at least 1000 ppm, thereby generating product ion mass spectrometry data; and
(f) optimize analyte identification or quantitation during data acquisition by comparing the product ion mass spectrometry data to the list of target analytes and target analyte product information.

In an embodiment, a mass spectrometer system for analyzing an analyte is provided, wherein:
the list of target analytes and target analyte product information comprises target peptides and target peptide product information corresponding to one or more proteins; the analyte comprises peptides corresponding to proteins; the controller controls the memory module, ion optics, mass analyzer and detector so as to:
(d) fragment precursor peptide ions having a preselected distribution of mass-to-charge ratios, thereby generating product ions; and
(f) optimize protein or peptide identification or quantitation during data acquisition by comparing the product ion mass spectrometry data to the list of target peptides and target peptide product information corresponding to one or more proteins.

In an embodiment, a mass spectrometer system for analyzing an analyte is provided, wherein the controller further controls the memory module, ion optics, mass analyzer and detector so as to:
identify target peptide product information in the product ion mass spectrometry data corresponding to a target peptide, thereby identifying a target peptide; and
remove the identified target peptide from the list of target peptides and target peptide product information corresponding to one or more proteins during data acquisition.

In an embodiment, a mass spectrometer system for analyzing an analyte is provided, wherein the controller further controls the memory module, ion optics, mass analyzer and detector so as to: remove the identified target peptide product information from the list of target peptides and target peptide product information corresponding to one or more proteins during data acquisition.

In an embodiment, a mass spectrometer system for analyzing an analyte is provided, wherein the controller further controls the memory module, ion optics, mass analyzer and detector so as to: identify one or more target peptides corresponding to a single protein, thereby identifying a target protein; and
remove all the identified target peptides and peptide product information from the list of target peptides and target peptide product information corresponding to one or more proteins which correspond to the identified protein during data acquisition.

In an embodiment, a mass spectrometer system for analyzing an analyte is provided, wherein the controller further controls the memory module, ion optics, mass analyzer and detector so as to: add target peptides and target peptide product information to the list of target peptides and target peptide product information corresponding to one or more proteins during data acquisition.

In an embodiment, the system further comprises a chromatography column in communication with the ion source for fractionating the sample.

In an embodiment, the system further comprises the controller further controls the memory module, ion optics, mass analyzer, chromatography column and detector so as to: calculate a chromatography column elution order of the peptides in the list of target peptides and target peptide product information corresponding to one or more proteins, thereby generating an elution order list;

sort the elution order list from first eluting peptide to last eluting peptide, thereby generating a sorted elution order list; fractionate the sample with the chromatography column prior to generating a distribution of precursor peptide ions from the sample;
identify target peptide product information in the product ion mass spectrometry data corresponding to a target peptide, thereby identifying a target peptide;
compare the identified target peptide to the sorted elution order list during data acquisition; and
identify one or more target peptides from the sorted elution order list which are within X peptides of the identified peptide, wherein X is equal to 20% of the total number of target peptides in the elution order list, thereby generating a list of next predicted eluting peptides.

In an embodiment, the target analyte product information comprises the masses of the target analytes or target analyte products. In another embodiment, the target peptide product information comprises the masses of the target peptides or target peptide products.

In an embodiment, the controller further controls the memory module, ion optics, mass analyzer, chromatography column and detector so as to: identify one or more peptides in the list of next predicted eluting peptides during data acquisition;
select a range of mass-to-charge ratios of precursor ions corresponding to the one or more peptides in the list of next predicted eluting peptides; and
measure the mass-to-charge ratios of the range of mass-to-charge ratios corresponding to the one or more peptides in the list of next predicted eluting peptides, thereby generating precursor mass spectrometry data.

In an embodiment, the controller further controls the memory module, ion optics, mass analyzer, chromatography column and detector so as to: identify one or more peptides in the list of next predicted eluting peptides during data acquisition;
wherein in step (d), the precursor peptide ions having a preselected distribution of mass-to-charge ratios correspond to the one or more peptides in the list of next predicted eluting peptides.

In an embodiment, the controller further controls the memory module, ion optics, mass analyzer and detector so as to: measure the mass-to-charge ratios of a range of mass-to-charge ratios corresponding to the distribution of precursor peptide ions, thereby generating precursor mass spectrometry data;
determine a signal-to-noise ratio of two or more peaks in the precursor mass spectrometry data corresponding to one or more peptides in the list of target peptides and target peptide product information corresponding to one or more proteins, during data acquisition; wherein at least one of the two or more peaks in the precursor mass spectrometry data corresponding to one or more peptides corresponds to a labeled protein and at least one corresponds to an un-labeled protein; and
repeat steps (c)-(f) if the signal-to-noise ratio of the least intense of the two or more peaks in the precursor mass spectrometry data corresponding to one or more peptides in the list of target peptides and target peptide product information corresponding to one or more proteins is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the controller further controls the memory module, ion optics, mass analyzer and detector so as to: identify target peptide product information in the product ion mass spectrometry data corresponding to a target protein, thereby identifying a target protein;
determine a signal-to-noise ratio of one or more peaks in the product ion mass spectrometry data corresponding to a sequence tag of the identified target protein during data acquisition; and
repeat steps (c)-(f) if the signal-to-noise ratio of one or more peaks in the product ion mass spectrometry data corresponding to a sequence tag of an identified target protein is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the controller further controls the memory module, ion optics, mass analyzer and detector so as to: identify target peptide product information in the product ion mass spectrometry data corresponding to a target protein, thereby identifying a target protein;
determine a signal-to-noise ratio of one or more peaks in the product ion mass spectrometry data corresponding to a reporter tag of the identified target protein during data acquisition; and
repeat steps (c)-(f) if the signal-to-noise ratio of one or more peaks in the product ion mass spectrometry data corresponding to a reporter tag of an identified target protein is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the controller further controls the memory module, ion optics, mass analyzer and detector so as to: select a target peptide having one or more sites of post-translational modification;
compare the product ion mass spectrometry data to the list of target peptides and target peptide product information corresponding to one or more proteins to determine if the sites of the target peptide having one or more post-translational modifications can be uniquely identified; and
adjust a fragmentation parameter during data acquisition until sites of the target peptide having the one or more post-translational modifications can be uniquely identified; wherein the fragmentation parameter corresponds to a fragmentation pressure, gas, electron energy, wavelength of electromagnetic radiation, power of electromagnetic radiation, illumination time of electromagnetic radiation, flux of electromagnetic radiation, total dose of electromagnetic radiation, collision energy, or reaction time.

In an embodiment, the controller further controls the memory module, ion optics, mass analyzer and detector so as to: select a target peptide having one or more sites of post-translational modification;
compare the product ion mass spectrometry data to the list of target peptides and target peptide product information corresponding to one or more proteins to determine if the sites of the target peptide having one or more post-translational modifications can be uniquely identified; and
adjust a fragmentation method during data acquisition until sites of the target peptide having the one or more post-translational modifications can be uniquely identified; wherein the fragmentation method is beam-type collision activated dissociation, ion reaction dissociation, electron reaction dissociation, electron transfer dissociation, electron capture dissociation, neutral reaction dissociation, laser-induced dissociation, surface induced dissociation, or resonant excitation collision activated dissociation.

In an embodiment, the controller further controls the memory module, ion optics, mass analyzer and detector so as to: select a target peptide having one or more sites of post-translational modification;
identify peaks in the product ion mass spectrometry data which correspond to the target peptide having one or more sites of post-translational modification;
compare the product ion mass spectrometry data to the list of target peptides and target peptide product information corresponding to one or more proteins during data acquisition to determine if the sites of the target peptide having one or more post-translational modifications can be uniquely identified; and
repeat steps (c)-(f) until sites of the target peptide having the one or more post-translational modifications can be uniquely identified.

The systems and methods described herein are especially useful in the context of isobaric or isotopic label-based analysis. In an embodiment, for example, a system is provided wherein the proteins or peptides are isobarically labeled proteins or peptides.

In an embodiment, the proteins or peptides are isotopically labeled proteins or peptides. In an embodiment, the proteins or peptides are phosphorylated proteins or peptides. In an embodiment, the proteins or peptides are co-translationally modified proteins or peptides. In an embodiment, the proteins or peptides are post-translationally modified proteins or peptides. In an embodiment, the proteins are indicative of a disease state.

In an embodiment, the controller further controls the memory module, ion optics, mass analyzer and detector so as to: identify target analyte product information in the product ion mass spectrometry data corresponding to a target analyte, thereby identifying a target analyte; and remove the identified target analyte from the list of target analytes and target analyte product information during data acquisition.

In an embodiment, the controller further controls the memory module, ion optics, mass analyzer and detector so as to: remove the identified target analyte product information from the list of target analytes and target analyte product information during data acquisition.

In an embodiment, the controller further controls the memory module, ion optics, mass analyzer and detector so as to: identify one or more target analytes corresponding to a single analyte, thereby identifying a target analyte; and remove all the identified target analytes and analyte product information from the list of target analytes and target analyte product information which correspond to the identified analyte, during data acquisition.

In an embodiment, the controller further controls the memory module, ion optics, mass analyzer and detector so as to: add target analytes and target analyte product information to the list of target analytes and target analyte product information during data acquisition.

In an embodiment, the system further comprises a chromatography column in communication with the ion source for fractionating the sample. In an embodiment, the controller further controls the memory module, ion optics, mass analyzer, chromatography column and detector so as to: calculate a chromatography column elution order of the analytes in the list of target analytes and target peptide analyte corresponding to one or more analytes, thereby generating an elution order list;
sort the elution order list from first eluting analyte to last eluting analyte, thereby generating a sorted elution order list;
fractionate the sample with the chromatography column prior to generating a distribution of precursor analyte ions from the sample;
identify target analyte product information in the product ion mass spectrometry data corresponding to a target analyte, thereby identifying a target analyte;
compare the identified target analyte to the sorted elution order list during data acquisition; and
identify one or more target analytes from the sorted elution order list which are within X analytes of the identified analyte, wherein X is equal to 20% of the total number of target analytes in the elution order list, thereby generating a list of next predicted eluting analytes.

In an embodiment, the controller further controls the memory module, ion optics, mass analyzer, chromatography column and detector so as to: identify one or more analytes in the list of next predicted eluting analytes during data acquisition; select a range of mass-to-charge ratios of precursor ions corresponding to the one or more analytes in the list of next predicted eluting analytes; and measure the mass-to-charge ratios of the range of mass-to-charge ratios corresponding to the one or more analytes in the list of next predicted eluting analytes, thereby generating precursor mass spectrometry data.

In an embodiment, the controller further controls the memory module, ion optics, mass analyzer, chromatography column and detector so as to: identify one or more analytes in the list of next predicted eluting analytes during data acquisition; wherein in step (d), the precursor analyte ions having a preselected distribution of mass-to-charge ratios correspond to the one or more analytes in the list of next predicted eluting analytes.

In an embodiment, the controller further controls the memory module, ion optics, mass analyzer, chromatography column and detector so as to: identify one or more analytes in the list of next predicted eluting analytes during data acquisition; select a range of mass-to-charge ratios of precursor ions corresponding to the one or more analytes in the list of next predicted eluting analytes; fragment precursor ions having mass-to-charge ratios within the selected range of mass-to-charge ratios; and measure the mass-to-charge ratios of the fragmented precursor ions, thereby generating product ion mass spectrometry data In an embodiment, the controller further controls the memory module, ion optics, mass analyzer, and detector so as to: measure the mass-to-charge ratios of a range of mass-to-charge ratios corresponding to the distribution of precursor analyte ions, thereby generating precursor mass spectrometry data;
determine a signal-to-noise ratio of two or more peaks in the precursor mass spectrometry data corresponding to one or more analytes in the list of target analytes and target analyte product information, during data acquisition; wherein at least one of the two or more peaks in the precursor mass spectrometry data corresponding to one or more analytes corresponds to a labeled analyte and at least one corresponds to an un-labeled analyte; and
repeat steps (c)-(f) if the signal-to-noise ratio of the least intense of the two or more peaks in the precursor mass spectrometry data corresponding to one or more analytes in the list of target analytes and target analyte product information is less than two-to-one, optionally three-to-one, optionally five-to-one, optionally ten-to-one, optionally twenty-to-one, optionally between two-to-one and twenty-to-one, optionally between five-to-one and twenty-to-one.

In an embodiment, the controller further controls the memory module, ion optics, mass analyzer and detector so as to: measure mass-to-charge ratios of at least a portion of the distribution of precursor analyte ions, thereby generating precursor analyte ion mass spectrometry data; and optimizing analyte identification or quantitation during data acquisition by comparing the precursor analyte ion mass spectrometry data to the list of target analytes and target analyte product information, wherein said list further comprises target analyte precursor ion information and landmark precursor ion signal information.

In an embodiment, a mass spectrometer system for analyzing an analyte is provided, the system comprising:
an ion source for generating ions from the analyte;
first ion separation optics in communication with the ion source for separating ions according to their mass-to-charge ratios;
ion fragmentation optics in communication with the first ion separation optics for generating product ions;
a mass analyzer in communication with the ion fragmentation optics for separating ions according to their mass-to-charge ratios; wherein the mass analyzer comprises an ion detector for detecting ions separated according to their mass-to-charge ratios;
a controller operably connected to the first and second ion separation optics, the first ion detector, and the ion fragmentation optics; wherein the controller comprises a memory module;
wherein the controller controls the memory module, ion optics, mass analyzer and detector so as to:
  (a) provide a list of target analytes, target analyte precursor ion information and landmark precursor ion signal information, wherein the list comprises from 25 to 5,000,000 target analytes;
  (b) provide a sample containing an analyte;
  (c) generate a distribution of precursor analyte ions from the sample;
  (d) measure mass-to-charge ratios of at least a portion of the distribution of precursor analyte ions in a mass analyzer, wherein the mass analyzer has a mass accuracy of at least 1000 ppm, thereby generating precursor analyte ion mass spectrometry data; and
  (e) optimize analyte identification or quantitation during data acquisition by comparing the precursor analyte ion mass spectrometry data to the list of target analytes, target analyte precursor ion information and landmark precursor ion signal information.

In an embodiment, a mass spectrometer system for analyzing an analyte is provided, the system comprising:
an ion source for generating ions from the analyte;
first ion separation optics in communication with the ion source for separating ions according to their mass-to-charge ratios;
ion fragmentation optics in communication with the first ion separation optics for generating product ions;
a mass analyzer in communication with the ion fragmentation optics for separating ions according to their mass-to-charge ratios; wherein the mass analyzer comprises an ion detector for detecting ions separated according to their mass-to-charge ratios;
a controller operably connected to the first and second ion separation optics, the first ion detector, and the ion fragmentation optics; wherein the controller comprises a memory module; wherein the controller controls the memory module, ion optics, mass analyzer and detector so as to:
  (a) provide a list of target peptides, wherein the target list comprises from 25 to 5,000,000 target peptides, optionally between 25 to 1,000,000 target peptides, optionally between 50 to 100,000 target peptides, or optionally between 50 to 10,000 target peptides;
  (b) calculate a chromatography column elution order and elution time of the peptides in the list of target peptides, thereby generating an elution order list and predicted elution times for each target peptide;
  (c) sort the elution order list from first eluting peptide to last eluting peptide, thereby generating a sorted elution order list;
  (d) provide a sample containing the analyte, wherein said analyte comprises peptides corresponding to one or more proteins;
  (e) generate a distribution of precursor analyte ions from the sample, wherein said analyte ions comprises peptide ions;
  (f) fragment precursor analyte ions having a preselected distribution of mass-to-charge ratios, thereby generating product ions;
  (g) measure the mass-to-charge ratios of at least a portion of the product ions collected in the mass analyzer at elution times corresponding to the predicted elution times for the target peptides, wherein the mass analyzer has a mass accuracy of at least 100 ppm, optionally a mass accuracy of at least 1000 ppm, thereby generating product ion mass spectrometry data; and
  (h) identifying target peptides or peptide product information in the product ion mass spectrometry data corresponding to a target peptide by comparing the product ion mass spectrometry data to the list of target peptides and target peptide product information.

In an embodiment, the target analyte product information comprises the masses of the target analytes or target analyte products. In another embodiment, the target peptide product information comprises the masses of the target peptides or target peptide products.

In an embodiment, a mass spectrometer system for analyzing an analyte is provided, wherein the system comprises:
an ion source for generating ions from the analyte;
first ion separation optics in communication with the ion source for separating ions according to their mass-to-charge ratios;
ion fragmentation optics in communication with the first ion separation optics for generating product ions;
a mass analyzer in communication with the ion fragmentation optics for separating ions according to their mass-to-charge ratios; wherein the mass analyzer comprises an ion detector for detecting ions separated according to their mass-to-charge ratios;
a controller operably connected to the first and second ion separation optics, the first ion detector, and the ion fragmentation optics; wherein the controller comprises a memory module, wherein the controller controls the memory module, ion optics, mass analyzer and detector so as to:
  (a) generate a sequencing queue containing a MS1 scan to be performed and one or more mass spectrometry scans to be performed, wherein said mass spectrometry scans to be performed in the sequencing queue correlate to analyte ion peaks having a predicted elution time, and said MS1 scan is not associated with an elution time;
  (b) generate a real-time heap queue containing one or more target scans to be performed, wherein said target scans to be performed correlate to peptides or target peptides having a predicted elution time, wherein any time a new mass spectrometry scan or target scan is to be performed, target scans in the real-time heap queue are performed ahead of any mass spectrometry scans from the sequencing queue;

(c) provide a sample containing an analyte;

(d) perform the MS1 scan when no other scans are present in the sequencing queue or real-time heap queue, wherein performing the MS1 scan comprises generating a distribution of precursor analyte ions from the sample and measuring mass-to-charge ratios of at least a portion of the product ions in a mass analyzer, thereby generating one or more analyte ion peaks;

(e) select one or more analyte ion peaks, generate a new mass spectrometry scan corresponding to each of the selected analyte ion peaks, and add the new mass spectrometry scan into the sequencing queue;

(f) perform one or more mass spectrometry scans from the sequencing queue, wherein mass spectrometry scans added more recently to the sequencing queue are performed after mass spectrometry scans added earlier to the sequencing queue, wherein performing one or more mass spectrometry scans comprises:

(i) fragmenting precursor analyte ions having a preselected distribution of mass-to-charge ratios, thereby generating product ions;

(ii) measuring the mass-to-charge ratios of at least a portion of the product ions in a mass analyzer, thereby generating product ion mass spectrometry data;

(g) identify a target analyte from the product ion mass spectrometry data, calculate an elution time for the target analyte, generate a new target scan corresponding to the target analyte and calculated elution time, and add the new target scan into the real-time heap queue;

(h) perform one or more target scans from the real-time heap queue, wherein target scans are performed at elution times corresponding to the calculated elution times for the target analytes, wherein performing one or more target scans comprises:

(i) fragmenting precursor analyte ions having a preselected distribution of mass-to-charge ratios, thereby generating product ions;

(ii) measuring the mass-to-charge ratios of at least a portion of the product ions in the mass analyzer, thereby generating product ion mass spectrometry data; and (i) compare product ion mass spectrometry data to a list of target analytes and target analyte product information.

The systems and methods described herein are especially useful in the context of isobaric or isotopic label-based analysis. In an embodiment, for example, a system is provided wherein the analyte is an isobarically labeled analyte. In an embodiment, the analyte is an isotopically labeled or isotopically coded analyte. In an embodiment, the analyte comprises one or more small molecules, pharmaceutical compounds, oligonucleotides, or sugars.

In an embodiment, the controller further controls the memory module, ion optics, mass analyzer, and detector so as to digest the one or more proteins. In an embodiment, the distribution of precursor analyte ions is generated by an electrospray ionization source or a MALDI source. In an embodiment, the system is implemented in a tandem mass spectrometer instrument, a multistage mass spectrometer instrument, or a hybrid mass spectrometer instrument.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE FIGURES

FIG. 1 provides a table showing the number of proteins observed in common across quintuplicate shotgun proteomic experiments (left) and microarray transcript analysis (right).

FIG. 8 provides OrbiQ "Figures of Merit", based on the known capabilities of each component and PRM performance of a Velos-Orbitrap.

FIG. 24 provides experimental results demonstrating that inSeq (Q-Exactive) was able to detect the 8 peptides of FIG. 22. inSeq was able to detect each of the 8 peptides at 2 fmol, while only 1 to 3 of these peptides were detected at 2 fmol using data-dependent acquisition (DDA).

FIGS. 25-30 provide schematic steps for instant sequence confirmation using inSeq. FIG. 25 shows first constructing a list of peptide targets from previous DDA experiments and sorting them according to elution order (CEO). FIG. 26 shows performing DDA using an inclusion list from the list of peptides. The peptides that are ID'd by inSeq are used to update the CEO window. FIG. 27 shows that when the average CEO approaches a target CEO, the PRM cycle for that target is started. FIG. 28 shows that the PRM scans are started at a regular frequency for a set time period. FIG. 29 shows that DDA scans proceed when there is a free opportunity in order to keep the CEO window updated. FIG. 30 shows continuing to perform DDA with the inclusion list until the next target enters the CEO window.

DETAILED DESCRIPTION

Figure 2:
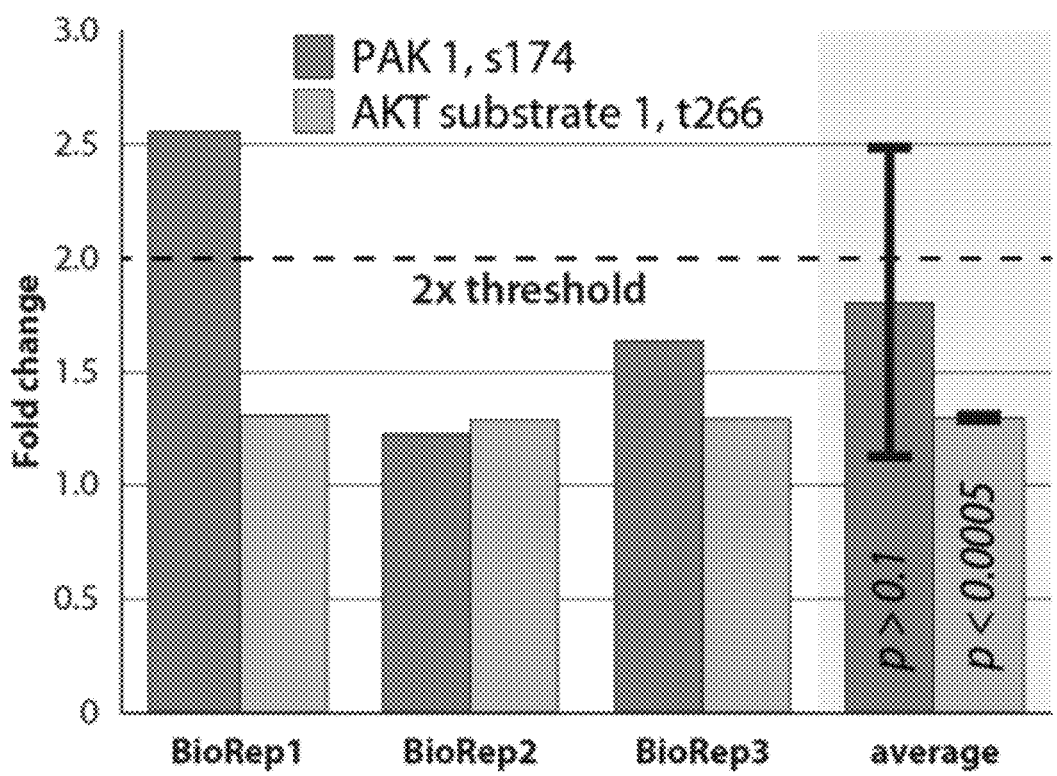
FIG. 2 provides a plot showing that application of a 2× change threshold filter can indicate changes that are not statistically significant (p>0.1, left bars, red), while missing subtle, but consistently changing proteins or phosphorylation sites (p<0.0005, right bars, gold).

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

As used herein, the terms "product ion" and "secondary ion" are used interchangeably in the present description and refer to an ion which is produced during a fragmentation process of a precursor ion. The term "secondary product ion" as used herein refers to an ion which is the product of successive fragmentations.

As used herein, the term "precursor ion" is used herein to refer to an ion which is produced during ionization stage of mass spectrometry analysis, including the $MS^1$ ionization stage of MS/MS analysis.

As used herein, the term "analyzing" refers to a process for determining a property of an analyte. Analyzing can determine, for example, physical properties of analytes, such as mass or atomic or substituent composition.

As used herein, the term "analyte" refers to a compound or composition which is the subject of an analysis. Analytes include, but are not limited to, proteins, peptides, small molecules, pharmaceutical compounds, oligonucleotides, and sugars. An "isotopically labeled analyte" refers to an analyte that has been labeled with one or more isotopic tagging reagents. Similarly, an "isobarically labeled analyte" refers to an analyte that has been labeled with one or more isobaric tagging reagents. For example, an "isobarically labeled analyte" can be a mixture containing proteins or peptides labeled with multiple isobaric tagging reagents where the isobaric tagging reagents generate different reporter ions during fragmentation As used herein, the term "target analyte product information" and "target peptide product information" refers to one or more measured attributes of the target analyte, target peptide, or ions or fragments of the target analyte or target peptide, selected from the group including, but not limited to, mass, signal intensity, mass-to-charge ratio, charge state, signal to noise ratio, and combinations thereof.

As used herein, the term "ion source" refers to a device component which produces ions from a sample. Examples of ion sources include, but are not limited to, electrospray ionization sources and matrix assisted laser desorption/ionization (MALDI) sources.

As used herein, the term "mass spectrometry" refers to an analytical technique for the determination of the elemental composition of an analyte. Mass spectrometric techniques are useful for elucidating the chemical structures of analytes, such as peptides and other chemical compounds. The mass spectrometry principle consists of ionizing analytes to generate charged species or species fragments and measurement of their mass-to-charge ratios. Conducting a mass spectrometric analysis of an analyte results in the generation of mass spectrometry data relating to the mass-to-charge ratios of the analyte and analyte fragments. Mass spectrometry data corresponding to analyte ion and analyte ion fragments is presented in mass-to-charge (m/z) units representing the mass-to-charge ratios of the analyte ions and/or analyte ion fragments.

"Quantitative analysis" is the determination of the absolute or relative abundance of one, several, or all particular substance(s) present in a sample. For biological samples, quantitative analysis performed via mass spectrometry can determine the relative abundance of peptides and proteins. The accepted methodology for performing mass spec quantitation is accomplished using a mass spectrometer capable of MS/MS fragmentation (i.e. triple quadropole or ion trap). The quantitation process typically involves isobaric tagging of peptide precursors, which when combined with post-acquisition software, provides the relative abundance of peptides.

As used herein, the term "interference" refers to a species detected in an analysis which interferes with the detection of a species or analyte of interest. Interference can refer to detection of a protein, or protein fragment, which is not a protein or protein fragment of interest and which interferes with the accurate detection or quantitation of the protein or peptide fragment of interest. Interference can be quantified as an interference ratio, such as a ratio of an amount of interference signal to an amount of analyte signal. In a mass spectral analysis, interference can be manifested as an interference peak which corresponds to detection of a species which is not an analyte of interest.

As used herein, the term "signal-to-noise ratio" refers to a measure which quantifies how much a signal has been corrupted by noise, or unwanted signal. It can also refer to the ratio of signal power to the noise power corrupting the signal. A ratio higher than 1:1 indicates more signal than noise and is desirable for some applications.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

As used herein, the term "ion optic" refers to a device component which assists in the transport and manipulation of charged particles, for example ions, by the application of electric and/or magnetic fields. The electric or magnetic field can be static, alternating, or can contain both static and alternating components. Ion optical device components include, but are not limited to, ion deflectors which deflect ions, ion lenses which focus ions, and multipoles (such as quadruples) which confine ions to a specific space or trajectory. Ion optics include multipole RF device components which comprise multiple rods having both static and alternating electric and/or magnetic fields.

As used herein, the term "mass spectrometer" refers to a device which creates ions from a sample, separates the ions according to mass, and detects the mass and abundance of the ions. Mass spectrometers include multistage mass spectrometers which fragment the mass-separated ions and separate the product ions by mass one or more times. Multistage mass spectrometers include tandem mass spectrometers which fragment the mass-separated ions and separate the product ions by mass once.

As used herein, the term "disease state" refers to condition that can cause pain, dysfunction, distress, social problems, and/or death to a patient. Methods and systems described herein can be useful for diagnosis of a disease state.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides include, for example, polypeptides comprising 1 to 100 amino acid units, optionally for some embodiments 1 to 50 amino acid units and, optionally for some embodiments 1 to 20 amino acid units.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, the term "controller" refers to a device component which can be programmed to control a device or system, as is well known in the art. Controllers can, for example, be programmed to control mass spectrometer systems as described herein. Controllers can be programmed, for example, to carry out ion manipulation and sample analysis methods as described herein on systems and devices as described herein.

As used herein, the term "fractionated" or "fractionate" refers to the physical separation of a sample, as is well known in the art. A sample can be fractionated according to physical properties such as mass, length, or affinity for another compound, among others using chromatographic techniques as are well known in the art. Fractionation can occur in a separation stage which acts to fractionate a sample of interest by one or more physical properties, as are well known in the art. Separation stages can employ, among other techniques, liquid and gas chromatographic techniques. Separation stages include, but are not limited to, liquid chromatography separation systems, gas chromatography separation systems, affinity chromatography separation systems, and capillary electrophoresis separation systems.

Example 1

A Quadrupole-Orbitrap Mass Spectrometer for High-Throughput, Reproducible Proteomics Note: numbers in brackets refer to the references listed at the end of this EXAMPLE 1.

The most widespread approach in proteomics couples shotgun identification methods with a variety of quantification strategies. These technologies have developed rapidly over the past decade and today it is routine to quantify thousands of proteins in just a few days [1-8]. Though this approach achieves high throughput, it lacks sensitivity and reproducibility. Specifically, complete coverage of specific pathways or functional groups is not typical (i.e., all 500 kinases, 1,400 transcription factors, etc.). Likewise, overlapping identifications in replicate experiments are low (35-60%) [9, 10]. This lack of completeness and reproducibility limit the quantity and quality of biological conclusions that can be drawn from a proteomic experiment. These limitations have propelled recent fervor in target-based methods, namely selected reaction monitoring (SRM) [11-16]. SRM achieves the reproducibility that the shotgun approach lacks and can determine absolute abundance, but suffers from low throughput and low resolution, as it is primarily restricted to the triple-quadrupole (QqQ) MS platform [16-19]. This embodiment of the present invention proposes the construction of a "crossover" instrument—a quadrupole-orbitrap hybrid—that combines the sensitivity and reproducibility of SRM methods with the high-throughput capacities of the shotgun technique. This new hardware platform is coupled with novel data acquisition schemes to provide the ability to rapidly and reproducibly monitor up to 1000 gene products with sensitivity equal to, or better than, state-of-the-art SRM methods. For example, this technology enables analysis of the mitochondrial proteome (1098 proteins), which is of outstanding importance to human health. The goal is to completely and precisely monitor the alterations of mitochondrial protein levels in response to cellular iron deprivation, the number one nutritional disorder worldwide [20].

Construction and Development of a Quadrupole-Orbitrap Hybrid Mass Spectrometer (OrbiQ).

A Thermo Scientific Exactive Orbitrap MS was adapted to incorporate a high resolution quadrupole mass filter. The instrument is designed to deliver unparalleled MS Figures of Merit—e.g., 10 Hz scan rate at 10,000 resolving power, fast, efficient high resolution isolation capability (±0.2 m/z), high mass accuracy (<5 ppm, external calibration), and intrascan dynamic range in excess of 15,000. These features enable real-time target confirmation (rtTC) as well as parallel reaction monitoring (PRM), among numerous other novel control features disclosed herein.

Implementation of a New Mass Spectrometer Data Acquisition Foundation—MaeStro.

The unique capabilities of the OrbiQ hardware set the stage for the next-generation of intelligent, directed data acquisition logic. The basis of the logic is to use real-time target confirmation (rtTC) to know which of the targets have been detected. This knowledge orchestrates data acquisition to deliver the desired Figures of Merit—the ability to target and quantify groups of up to 1,000's of proteins with high reproducibility (>95%) and sensitivity equivalent to, or in excess of, current SRM targeted approaches. The analysis scheme is analogous to 'feedback' in electronics, where the output of a device is used to modulate the input to further direct or change the output.

Proteomic and Transcriptomic Analyses of Mitochondrial Adaptation to Iron Deprivation.

The new capabilities of the OrbiQ-MaeStro platform can be leveraged to monitor with unprecedented precision the expression status of the 1098 mitochondrial proteins during a 48 hour time course of iron deprivation in cultured skeletal muscle cells. Additionally, matched microarray analyses can be performed on all conditions. This approach can (1) enable one to investigate the extent to which the entire mitochondrial proteome is restructured in response to an important physiological stress, and (2) provide a foundation to decipher the transcriptional and post-transcriptional mechanisms key to mitochondrial adaptation.

Proteomics.

The most widespread technique in proteomics is the shotgun method. Proteins are digested into peptides, chromatographically separated, and measured by mass spectrometry (MS) [21, 22]. Many types of mass spectrometers are used—quadrupole ion traps (QIT), QIT hybrids such as the Orbitrap or LTQ-FT-ICR, and quadrupole time-of-flight (Q-TOF)—but the experiments from MS measurements onward are basically the same. Eluting peptide cations have their mass-to-charge (m/z) values measured in the $MS^1$ scan. The most abundant precursors are then selected for a series of sequential tandem MS events ($MS^2$). The number of these events depends on the acquisition rate of the device, but generally ranges from 3 to 15. Following a second $MS^1$ scan, a new group of targets is selected. The process, called data-dependent acquisition (DDA) continues for the duration of the chromatographic separation. Because this method has not changed over the past fifteen years, advancements have come from the constant evolution of the MS hardware. Significant improvements in key Figures of Merit such as sensitivity, scan rate, mass accuracy, and resolution have evolved over this period. For example, the ion trap-orbitrap hybrid system can achieve high mass accuracy (<5 ppm) measurements for both $MS^1$ and $MS^2$, with high sensitivity at repetition rates of ~4 Hz [23]. Constant operation of such systems generates hundreds of thousands of spectra in days. These spectra are then mapped to peptide or protein sequence using highly evolved database search algorithms like SEQUEST [24], MASCOT [25], OMSSA [26], and several others. Successful results can be obtained within just a few days of instrument analysis time, and are nothing short of spectacular: tens of thousands of unique peptide spectral matches mapping to several thousand unique protein isoforms have become the norm. And, coupling these methods with isotopic-based labeling enables the dynamic comparison of the abundances of these proteins and peptides across perturbed cells or tissues [27, 28].

Limitations of Current Technology.

Irreproducibility—Identifying statistically significant differences in protein or PTM abundance requires reproducibility. Low reproducibility is a widely known problem in proteomics and stems from the stochastic nature of the data-dependent acquisition paradigm [9, 29-31]. It is, however, rarely discussed as the field has mostly focused on documenting larger and larger protein and PTM lists. A recent inter-laboratory study determined that peptide lists from pairs of technical replicates overlapped by only 35-60% [10]. These results agree with a recent analysis performed in quintuplicate (FIG. 1) where 3,061 proteins were identified in at least one of the five shotgun experiments, but observed only 954 of those proteins in all replicates. FIG. 1 contrasts these results with those from the paired transcriptomic measurements—which saw a 95% overlap between all five microarray assays (note only transcripts corresponding to the detected proteins are shown). Thus, for the proteomics work, the statistical power that should have been achieved by performing the analysis five times was obtained for only one-third of the proteins. Further, the proteins identified each time were the less interesting, more abundant species.

FIG. 2 relays the necessity of replicate measurements. In the first experiment, a phosphorylation site on PAK1 was detected to be up-regulated almost 2.5-fold. Another site on AKT substrate 1 shows only a ~1.3-fold change. Almost all comparative proteomic experiments—even those published in the highest tier—would conclude from a greater than 2-fold up-regulation that the PAK 1 site has significance and recommend it for biological follow-up. Yet the experiment was performed on two additional biological replicates and discovered that the significance of the PAK1 site was low ($p \leq 0.1$) while the AKT substrate 1 site was consistently, albeit slightly, different ($p<0.0005$). It is believed that proteomic technology will not fully realize significant biological and medical impact until it can routinely achieve detection and quantification of the same protein subsets across multiple measurements.

Inability to Select Protein Targets and Low Sensitivity.

Figure 3:
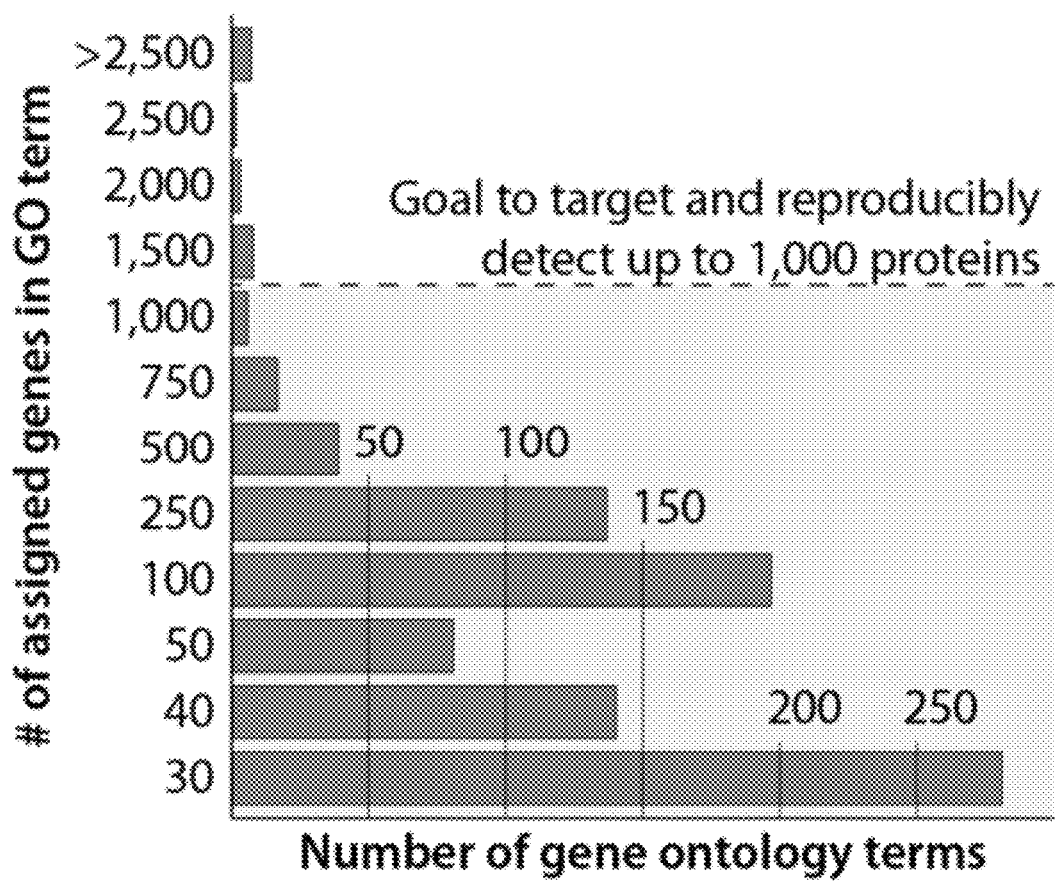
FIG. 3 provides a histogram of gene ontology (GO) term groupings, by the number of proteins in each. Only 20 GO groupings contain more than 1000 members.

Another weakness of the shotgun paradigm is the inability to select specific protein targets, which leads to results with spotty coverage and lower sensitivity than target-driven methods. For instance, the most expansive studies to date only report the detection of about half of the 500 kinases in human cells [32-35]. Kinases regulate cell function and play a particularly important role in signal transduction and complex functions like the cell cycle [36]. Yet shotgun proteomics presents data on several thousand other proteins, casting a large but non-directed net. In many, if not most experiments, complete coverage of selected pathway members or functional protein groups would be much more valuable than a list ten-times as large with broad, diffuse coverage. It was then asked how many proteins must be targeted to obtain complete coverage of most biological pathways. To answer this question, the 918 Gene Ontology (GO) categories [37] were analyzed. By annotating gene products according to three domains—cellular component, molecular function, and biological process—the ontology tabulates the magnitude of known protein groups and pathway members. From FIG. 3 it was concluded that nearly all GO groupings contain fewer than 1,000 members (only 20 are larger). Thus, an essential Figure of Merit was set for this technology: the ability to target and quantify groups of up to 1,000 proteins with high reproducibility (>95%) and sensitivity equivalent to, or in excess of, current state-of-the-art SRM targeted approaches.

Selected-Reaction Monitoring (SRM): An Imperfect Solution.

Figure 5:
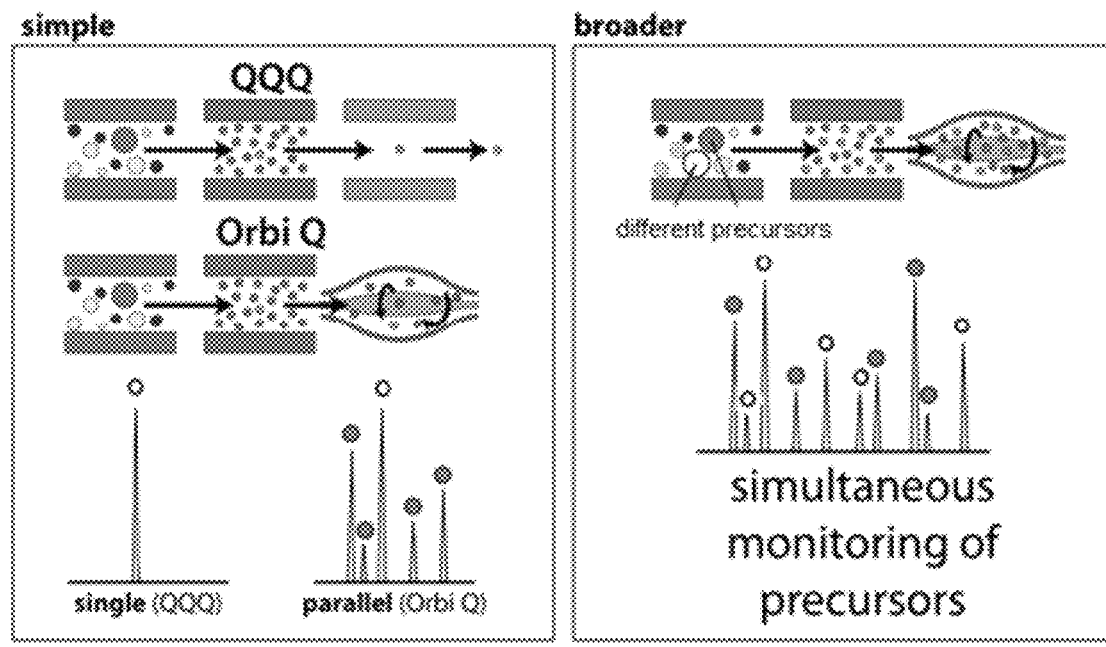
FIG. 5 provides schematic of a QqQ system able to select pre-defined precursors and detect their product ions one at a time. Also shown is a simple OrbiQ system able to detect all of the product ions generated from one precursor, and a broader OrbiQ system able to detect multiple product ions from multiple precursors.

The limitations of shotgun proteomics have propelled recent fervor in target-based methods in which prior system knowledge pre-selects candidate proteins for detection and abundance measurement. The fastest growing biological MS technique, SRM achieves the reproducibility that the shotgun approach lacks. It can also determine absolute abundance. Exploiting the unique capabilities of triple quadrupole MS systems (QqQ), SRM selects pre-defined precursors and detects their product ions one at a time (FIG. 5). In this way, the method can boost sensitivity for targeted peptides by orders of magnitude compared to the discovery-driven scanning techniques. Interest in QqQ SRM methods for targeted proteomics has soared in recent years. This trend illustrates the increased importance of reproducibility and sensitivity in proteomic experiments.

That said, obstacles hindering pervasive use of SRM technologies are many. The experiment requires (1) a QqQ system, a very different hardware platform than the more widespread discovery devices, and (2) specialists, even within expert laboratories. The method is also laborious. Because one channel is monitored at a time, parallel detection is not possible. Further, the low-resolution inherent in the QqQ system detection can cause interference, especially at low signal-to-noise ratios (S/N) [18, 19]. Finally, the method is markedly low throughput: quantifying only a handful of proteins (less than 20) often requires several months of effort. The ideal solution combines an at least 50-fold increase in throughput with the current ability to target selected pathways with high reproducibility.

The OrbiQ Hybrid.

Figure 4:
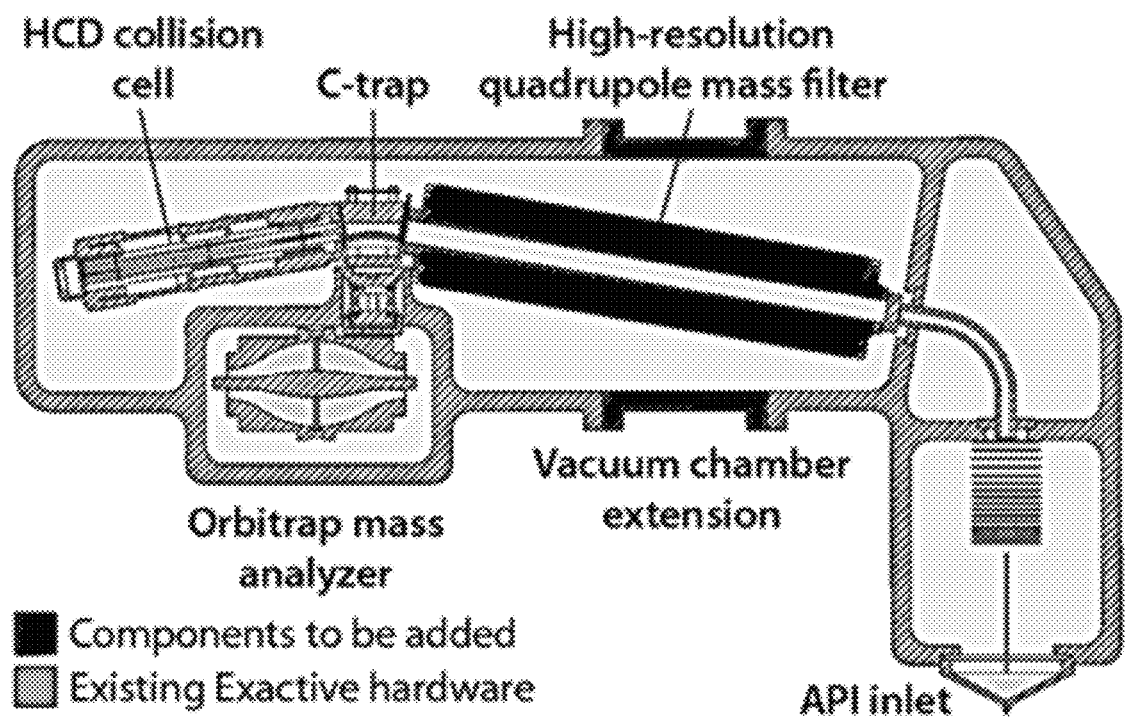
FIG. 4 provides a schematic of the OrbiQ mass spectrometer.

Shown in FIG. 4 is a schematic of the quadrupole-Orbitrap hardware (OrbiQ). The OrbiQ configuration is a cross between the powerful LTQ-Orbitrap discovery platform and the QqQ. Below it is detailed how this hardware arrangement can perform superior to either of its predecessors. And while the physical arrangement of the device is a critical component in achieving this performance, a new, highly innovative instrument control logic and data acquisition strategy (Mae-Stro) will drive this technology.

Strengths of the OrbiQ Geometry.

The OrbiQ has geometry similar to the current commercial LTQ-Orbitrap; however, a high resolution quadrupole mass filter replaces the linear ion trap. Several benefits follow from such an arrangement. First, one can increase the magnitude of a precursor ion population at least 10-fold, as the ion trap is adversely affected by space charge with large ion populations [38-42]. Though the linear ion trap efficiently isolates targets for small ion populations (e.g., <100,000 charges), it cannot isolate larger populations. With a quadrupole mass filter isolation occurs in a transmission rather than trapping mode, so that one can easily accumulate 1,000,000 charges of any selected precursor. Second, charges of a selected precursor can be accumulated even in the presence of much more abundant contaminants because the mass filter performs extremely high resolution isolations: ~0.2 m/z, about 10× better than routinely achieved with the linear ion trap system. With ion traps, if one species is more abundant during isolation, purifying a relatively low-level component also present—i.e. achieving high sensitivity—is problematic.

The OrbiQ, essentially a QqQ with replacement of Q3 by an Orbitrap, also improves resolution compared to the standard QqQ. From this perspective, one can see how the device stands to capitalize on the selected-reaction monitoring (SRM) capability of the QqQ while boosting throughput, mass accuracy, and resolving power. Because of the inherent low resolution of the QqQ, each precursor-to-product transition must be monitored independently. Furthermore, increasing the number of monitored transitions incurs costs in sensitivity, as the experimenter spends less time per transition. With the high resolution provided by the OrbiQ each product ion is readily resolved, so that one can simultaneously monitor all the product ions generated from one precursor (FIG. 5). It is also possible to monitor the product ions generated from multiple precursors (FIG. 5).

Figure 6:
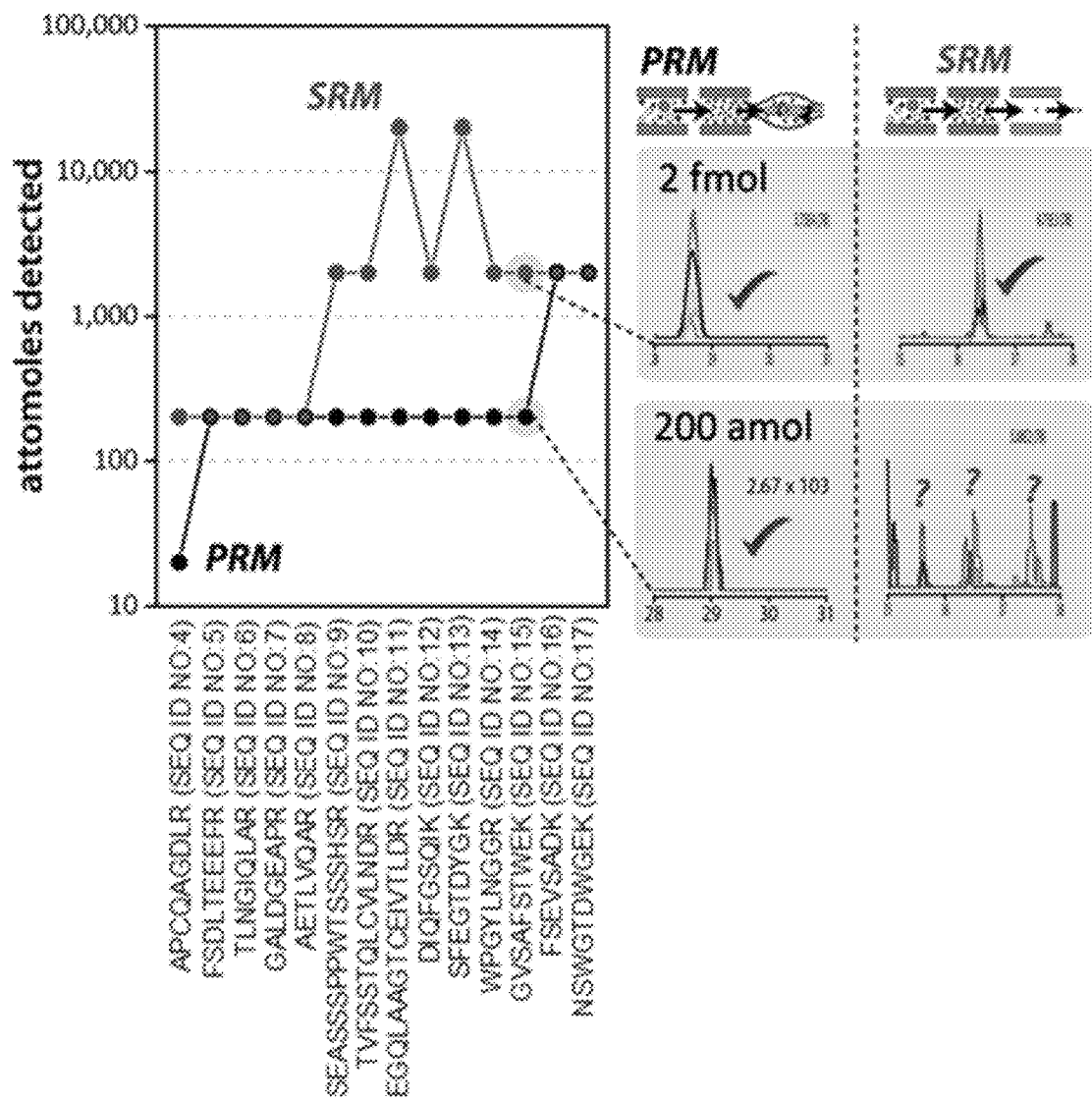
FIG. 6 provides a sensitivity assessment of SRM (QqQ) and parallel reaction monitoring (PRM) (OrbiQ). Several synthetic peptides were spiked into a complex mixture of yeast peptides ranging from 20 to 20,000 amol. Each peptide sequence (x-axis) indicates the lowest detectable amount for each method. The insets on the right display how accurate mass measurements can permit detection of low-level targets in complex backgrounds.

Additionally, parallel reaction monitoring (PRM) using the OrbiQ provides improved sensitivity over SRM using QqQ. FIG. 6 provides sensitivity assessment of SRM (QqQ) and PRM (OrbiQ). Several synthetic peptides were spiked into a complex mixture of yeast peptides ranging from 20 to 20,000 attomoles (amol). The lowest detectable amount of each peptide sequence is indicated. The PRM was able to detect peptides at amounts as low as 200 amol. The lowest peptide amount detected by SRM was 2 femtomoles (fmol). This represents an order of magnitude difference. In other words, the OrbiQ platform makes parallel reaction monitoring (PRM) a reality, virtually eliminating the low throughput drawbacks of SRM.

Instrument Control and Data Acquisition.

The stochastic nature of data-dependent acquisition (DDA) is a central cause of irreproducibility in shotgun experiments [43]. Consequently, a major consideration in the design of the OrbiQ geometry is compatibility with new, innovative data acquisition methodologies. Over the past several years, numerous groups have investigated DDA alternatives [11, 13, 14, 44-54]. These works can be grouped into two categories: (1) data-independent and (2) targeted. In the data-independent methods, $MS^2$ scans are not triggered from the $MS^1$ spectra; rather, fixed isolation widths, activation parameters, and scan ranges are used and cycled over an LC gradient. This strategy improves dynamic range due to gas-phase fractionation [55-57]. In addition, it resolves the stochastic nature of the DDA method. Finally, though reproducibility has not been extensively compared, these early results indicate strong improvements over DDA. The major disadvantage of the current data-independent implementation is a 10-20× loss in throughput, as the sample must be analyzed numerous times to cover the entire precursor mass range. Targeted approaches include both SRM and inclusion/exclusion listing. Both inclusion and exclusion employ the basic framework of the DDA method. With inclusion, only $MS^1$ signals falling in specific, pre-selected m/z ranges are interrogated; with exclusion, features falling in specific, pre-selected m/z ranges are not interrogated. The inclusion list approach yields slightly improved reproducibility (~60%) of these pre-selected peptides and can boost sensitivity. The number of overall identifications, however, drops substantially from the DDA method because unlisted features are ignored. Further, without gas-phase enrichment, sensitivity for list methods is lower than the data-independent strategy.

A new data acquisition/instrument control code (MaeStro) is disclosed herein that builds upon these themes (i.e., SRM, inclusion/exclusion list, and data-independent). The unique capabilities of the new OrbiQ hardware arrangement allow for significant creativity in the sampling process. This hardware, combined with the innovative MaeStro control code, represents a "crossover" mass spectrometer system that bridges the gap between the large-scale discovery and low-throughput targeted regimes. Such a device can deliver true hypothesis-driven proteomics to expert and non-expert laboratories alike.

Mitochondria.

The devices and methods described herein can be utilized, for example, to study several outstanding questions in mammalian mitochondrial biology. Mitochondria are ubiquitous organelles essential to the survival of nearly every eukaryotic cell. Although they are best known for ATP production via oxidative phosphorylation (OXPHOS), they house myriad other biochemical pathways and are centers for apoptosis and ion homeostasis. Mitochondrial dysfunction causes over 50 diseases ranging from neonatal fatalities to adult onset neurodegeneration, and is a likely contributor to cancer and type II diabetes [58-60]. A recent study led by Co-Investigator Pagliarini established a compendium of 1098 mammalian mitochondrial proteins across a wide range of tissues from healthy mice [61]. This work provides a robust, yet static view of the mitochondrial proteome. An important next step is to capture the alterations in the mitochondrial proteome that occur during acute cellular stresses, as well as in chronic diseases involving mitochondrial dysfunction.

The cellular process of producing and altering these organelles—termed mitochondrial biogenesis—is highly complicated, and involves the orchestrated transcription, translation, and assembly of more than 1000 proteins encoded by two genomes [61]. Eukaryotic cells have the ability to customize the mitochondrial biogenesis program to meet their metabolic needs, and mounting evidence suggests that post-transcriptional mechanisms are key to regulating the extent and specificity of this process. For example, translational control by upstream open reading frames (uORFs) and sub-mitochondrial targeting by mRNA binding proteins, are important for some mitochondrial genes [62-65]. Moreover, the global correlation between protein and mRNA levels is quite poor for mitochondrial proteins, indicating that many other post-transcriptional mechanisms are awaiting discovery [66].

The technology described here has revolutionary potential for advancing understanding of mitochondrial biogenesis and regulation by allowing complete and precise monitoring of the alterations of mitochondrial protein levels in response to physiological stresses. In particular, focus can be put on monitoring these changes during iron deprivation in skeletal muscle cells. This physiological stress was chosen for three key reasons: 1) iron deprivation is the top nutritional disorder worldwide [20], 2) this stress is particularly damaging to mitochondrial function where iron is an essential cofactor for a range of metabolic pathways, and 3) change in iron levels is well-known to induce post-transcriptional regulation of cellular gene expression [67, 68]. The quintessential mechanism involves the use of mRNA binding proteins that become active during low-iron conditions. Once activated, these proteins then bind to specific mRNA motifs leading to changes in mRNA stability or translation rate [67].

Figure 7:
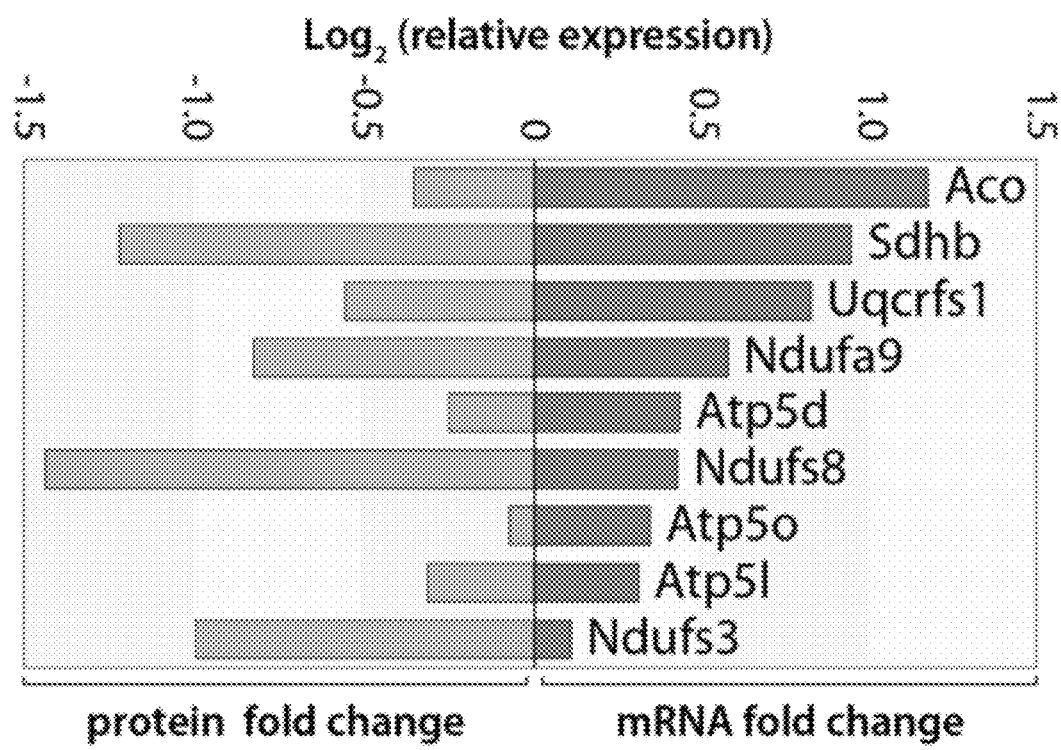
FIG. 7 provides a plot of several mitochondrial transcript expression levels and their corresponding protein abundances in response to acute iron stress.

Data suggest that a number of selected mitochondrial proteins are regulated post-transcriptionally following acute iron stress by what may be a similar iron-regulated mechanism (FIG. 7). It is hypothesized that much of the rest of the mitochondrial proteome will be similarly affected; however this has never been tested on a large-scale. By application of the OrbiQ-MaeStro platform and matched microarray analyses, the changes in proteins and pathways that underlie mitochondrial adaptation to iron deprivation can be elucidated and, more broadly, a framework for identifying post-transcriptional mechanisms driving the mitochondrial biogenesis program can be provided.

A Quadrupole-Orbitrap Hybrid MS System (OrbiQ).

This unique "crossover" mass spectrometer can deliver the high selectivity that is currently only achieved by use of QqQ instrumentation in SRM mode. The OrbiQ; however, can deliver high scan speed (10 Hz), high resolution (>10,000), and high mass accuracy (<5 ppm, external calibration, $MS^1$ and $MS^2$). These extraordinary Figures of Merit enable high-throughput targeted experiments by enabling numerous new acquisition strategies.

Parallel Reaction Monitoring (PRM).

This concept is enabled by the high-resolution Orbitrap analyzer and can remedy the extremely low throughput problem of SRM. The high resolving power of the orbitrap analyzer makes distinguishing target product ions from contaminants straightforward. Data presented herein demonstrates this concept. The key question is how the sensitivity of OrbiQ PRM compares to QqQ SRM. The present calculations and data indicate it can be superior.

Real-Time Target Confirmation (rtTC).

By confirming the detection of a target during the analysis, the stage is set for next-generation of MS data acquisition—this is a highly enabling and exciting innovation. The rtTC method has been implemented on an existing Velos-Orbitrap MS (further described herein).

MaeStro Control Logic.

These data acquisition approaches can reshape the proteomic landscape by offering a direct and straightforward means to reproducibly monitor large protein networks and pathways (e.g., up to 1000) with unprecedented sensitivity. Versions of both MaeStro algorithms have been implemented on an existing Velos-Orbitrap MS (further described herein). The scan rate of the OrbiQ results in an approximate 3× increase in throughput. Additional methods include use of retention order grouping, fractionation, and peptide spectral libraries for target prediction (e.g., PeptideAtlas). This can result in an approximate 10× boost in target capacity to readily detect several peptides from each of 1000 protein targets in a single experiment.

A Dynamic Map of Mitochondrial Adaptation to a Key Physiological Stress.

For the first time, alterations in the entire mitochondrial proteome over time from iron-deprived cells can be detected. Integrating this data with matching microarray data can provide a robust foundation for elucidating both the metabolic changes that occur in this organelle during iron chelation, and the mechanisms driving these changes. A dataset of this depth and clarity is unprecedented for mitochondria or for any system of comparable size and complexity.

a Quadrupole-Orbitrap Hybrid MS (OrbiQ).

In an embodiment, the OrbiQ hybrid system can be constructed on the newly introduced Thermo Scientific Exactive benchtop Orbitrap system. The Exactive comprises an ion funnel AP inlet, a transfer multipole, a c-trap, a collision cell, and an Orbitrap analyzer. The system is nominally designed for LC/MS small molecule screening and offers the ideal platform for the OrbiQ. First, it achieves the desired resolution and mass accuracy (see FIG. 8) to permit the innovative instrument control technologies described herein. Second, it can achieve a scan rate of 10 Hz~3 times that of the Velos Orbitrap. Third, modification of the system to replace the transfer multipole with a resolving quadrupole is straightforward. FIG. 4 presents a schematic diagram of the Exactive instrument and the modifications.

The primary modification is the addition of a high resolution mass filter, providing the precursor isolation capabilities of a modern QqQ MS. Using a mass filter rather than a linear ion trap increases ion throughput and isolation fidelity. The former translates to higher duty cycle and the latter enables the isolation of precursors independent of ion count or neighboring interference. As described herein, isolation fidelity issues often arise with ion traps due to their limited space charge capacity [38-42]. A quadrupole rod set from the Thermo Scientific TSQ Quantum MS system can be used. The mass filter has true hyperbolic rods with $r_0$=6 mm and is 250 mm long. The length and overall design provides excellent resolution (~±0.2 m/z isolation widths); however, to accommodate them the existing vacuum chamber must be extended.

The Exactive platform does not contain the electronic circuitry to drive a mass filter. The system does, however, have 4 spare digital-to-analog converters (DACs). A power supply can provide the RF waveforms, resolving DC, and offset DC needed to drive the quadrupole. This power supply enables all the voltages to scan a mass range from 50 to 2000 m/z with better than unit resolution. Three analog inputs along with one digital input can control of the power supply (and hence mass filter). These inputs can be interfaced with the spare DACs of the Exactive to provide complete and integrated control of the mass filter. Through the instrument control code (ITCL) the DACs can be set to regulate the mass selection, resolving power, and DC offset. The fourth DAC can enable operation of the mass filter in RF-only or mass resolving mode. Operation in RF-only mode allows for collection of $MS^1$ scans in the Orbitrap. ITCL control can render the instrument versatile and capable of automated experiments.

Obtaining the Highest Performance from the OrbiQ, However, Requires New Data Acquisition Strategies.

FIG. 8 outlines Figures of Merit based on the known capabilities of each component and operation in a targeted SRM mode. Performance in SRM mode can rival or surpass that of state-of-the-art QqQ experiments. This conclusion may not be readily apparent, as electron multiplier-based detection (used in the QqQ) is inherently more sensitive than image current schemes (Orbitraps). In fact, an approximately 5 to 10× difference in sensitivity between the electron multiplier-based detection and the Orbitrap is possible.

Greatly Improved Mass Resolution and Accuracy is the Answer.

Such resolution confers the ability to monitor all fragments produced by a given precursor in parallel (parallel reaction monitoring, PRM), which in turn significantly boosts signal intensity. Take, for example, an assay targeting 6 transitions in an SRM-QqQ experiment. If 50 ms is spent on each transition, the total monitoring time is 300 ms. OrbiQ PRM can monitor all 6, plus any other fragment produced, at once. In the same 300 ms, then, the OrbiQ has an injection time 6× longer: each individual fragment will have a raw signal intensity 6× greater than those provided by the QqQ. Furthermore, on average, each precursor generates 12.8 fragments (trypsin, n=9437): the OrbiQ approach will detect at least twice the number of fragments possible, per precursor, than the typical SRM approach. In this way, the mass resolution and accuracy afforded by the OrbiQ translates to much larger gains when detecting and quantifying precursors existing at low abundance levels in complex matrices.

OrbiQ Testing/Validation.

First, standards (no chromatography) can be employed to carefully evaluate ion transmission and the effect of RF amplitude and DC offsets of the various ion optics. Once this is understood, the next step is careful characterization and calibration of ion stability in the high resolving quadrupole mass filter. Careful attention should be paid to understanding the tradeoff between isolation resolution and efficiency. After these fundamental performance metrics have been established, higher level functionality—e.g., predictive automatic gain control (pAGC), standard data-dependent acquisition, standard SRM methods, etc, can be added. Establishment of these basic features enables directly comparing the new OrbiQ to (1) the Velos Orbitrap for shotgun proteomics and (2) the QqQ for targeted SRM experiments. Benchmark performance can be based on fractionated yeast whole cell lysate in the standard shotgun assay [3, 69, 75-86]. Dozens of yeast proteins across the dynamic range can be quantified with isotopically labeled standards by SRM on a QqQ [45].

Implementation of a New Mass Spectrometer Data Acquisition Foundation—MaeStro.

Though a hardware advance in its own right, coupling the original OrbiQ technology with the conventional DDA or targeted SRM acquisition modes offers only modest improvements above current state-of-the-art platforms. Performance under those conditions can fall short of our essential Figure of Merit: the ability to target and quantify groups of up to 1,000 proteins with high reproducibility (>95%) and sensitivity equivalent to, or in excess of, current SRM targeted approaches. The unique capabilities of the hardware—high mass accuracy and resolution, sensitivity, and rapid scan rate (10 Hz)—sets the stage for the next-generation of intelligent, directed data acquisition logic.

Instrument Control.

To move away from the DDA approach toward a SRM-like targeted regime, both inclusion listing and SRM strategies are used to build upon. The first step is to confirm the validity of real-time Target Confirmation (rtTC). By knowing which of the 1000 targets have been detected, data acquisition can be orchestrated to deliver the desired Figures of Merit. This analysis scheme is analogous to 'feedback' in electronics, where the output of a device is used to modulate the input to further direct or change the output.

The rtTC method is possible due to the high mass accuracy and resolution afforded by the Orbitrap analyzer. Consider an isolation range of 400.0-403.0 m/z, for example. Following in silico tryptic digestion of the 1098 mitochondrial proteins ~17,000 peptide candidate sequences fall within this range. First, most of these candidates are eliminated because only three or four peptides from each protein are of interest. If only three peptides per protein are searched for, then only 45 candidate target sequences need be considered for this precursor m/z range. It is here where accurate mass measurement of the Orbitrap is truly enabling. The rtTC method incorporates a simple peptide-spectrum match (PSM) scoring model based on the number of theoretical fragment peaks matched to within a very narrow product m/z tolerance (e.g., <0.01 Th). The effect of mass tolerance on peptide spectral matches (PSMs) was examined using a simple scoring model on a data set collected on a Velos Orbitrap. These data demonstrate that as the m/z tolerance is narrowed the average number of peptide fragment matches required to maintain a 1% FDR (via reversed-decoy strategy [87]) is greatly reduced. It is believed that rtTC is (1) possible, if one has sufficient mass accuracy, and (2) expedient, as only a few candidates sequences need be considered following each $MS^2$ event.

Figure 9:
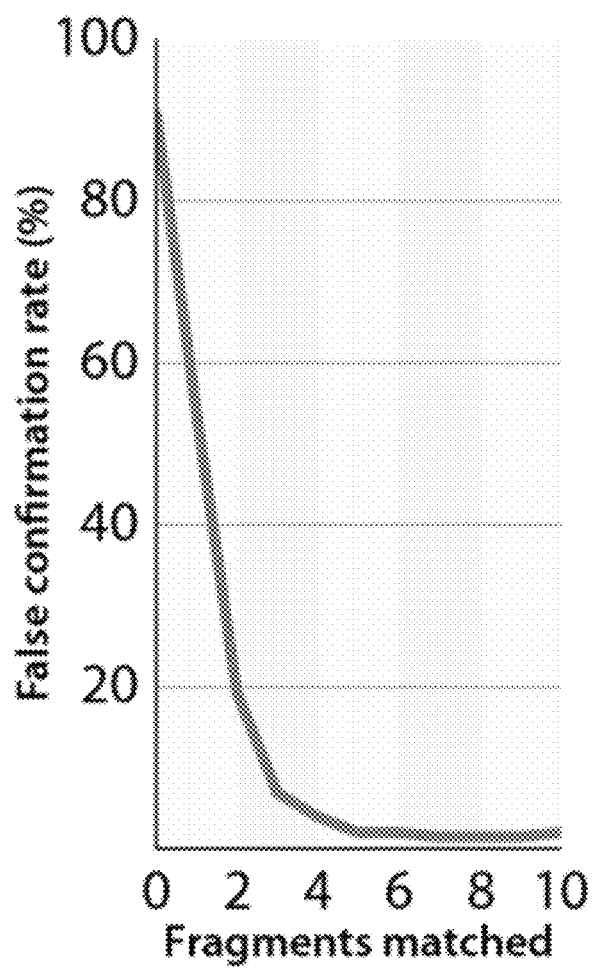
FIG. 9 provides a plot showing the rate of disagreement between OMSSA identifications (1% FDR) and rtTC as a function of the number of products matched by rtTC.

Next, rtTC was implanted into the ITCL control software of a Velos Orbitrap MS. Prior to analysis, a list of ~1300 targeted peptide sequences and their corresponding precursor and product ion m/z values were loaded onto the instrument control firmware. Any targeted precursor m/z peaks detected in the high resolution $MS^1$ scan were selected for high resolution $MS^2$ (standard inclusion list operation). Immediately following the $MS^2$ scan, the instrument firmware compares the m/z peaks to the theoretical product ion list (~1 ms per scan). In these control experiments, the instrument simply tabulated the number of matched fragments rather than make decisions based on matched product ions. For a given target, the predicted sequence was compared to the sequence determined via traditional, post-acquisition whole-proteome database searching. FIG. 9 plots the rate of agreement between these two sequences as a function of the fragments matched during rtTC. Approximately 99% of rtTC target detections (≥5 matched products) agree with post-acquisition searching.

MaeStro1: Directed Data Acquisition Through $MS^1$ Detection.

MaeStro1 is a directed data-acquisition approach that relies on detection of targeted peptide precursors following $MS^1$ analysis. To start, the established, but not widely employed, inclusion list concept is built upon. This method accepts a static list of precursor m/z targets which, when detected, are targeted for $MS^2$. Targets, which are never removed from the list in this embodiment, undergo analysis as many times as there exists a matching precursor peak. To explore this method, a standard DDA approach was used to analyze a yeast protein lysate digested with trypsin in triplicate. Of the 7,907 unique peptides identified in total, only 3,684 peptides were observed in all three experiments.

1,328 of the 2,400 peptides that were only detected in one of the three replicates were then selected by removing peptides identified with variable modifications, I/L homologous sequences, etc. These single replicate peptides (SRPs) were used to determine the duty cycle and success rate of the standard inclusion list approach. Over a two hour LC gradient, the inclusion list made 7,512 $MS^2$ attempts, of which only 600 of the 1,328 unique peptide targets were successfully mapped to sequence (VA FDR). Because each target resulted in ~7 $MS^2$ attempts, the number of targets that can be included is limited. Some of the targets were selected over 200 times. These weaknesses preclude the goal to identify up to 1,000 pre-selected proteins. To do this, at least 3,000 unique peptides (3 peptides per protein) need to be detected. Without an iterative analysis scheme, in which the detected targets of one run are removed and new ones added, the standard inclusion list approach does not have the necessary throughput.

MaeStro1 was designed to solve this problem. The control logic is engineered so that a large number of targets are hunted in a single experiment. The key is to reduce the number of failed $MS^2$ attempts. Here implementing rtTC allows the removal of confirmed targets from the list immediately. Implementation of this approach on the same sample resulted in the generation of only 3,121 $MS^2$ events and 800 detected targets: only ~3 $MS^2$ attempts were made per target, yet the number of detected targets increased by 33%. This gain results from the detection of lower signal targets identified as the run proceeds, after the rtTC algorithm removed positively detected targets of greater abundance.

Figure 10:
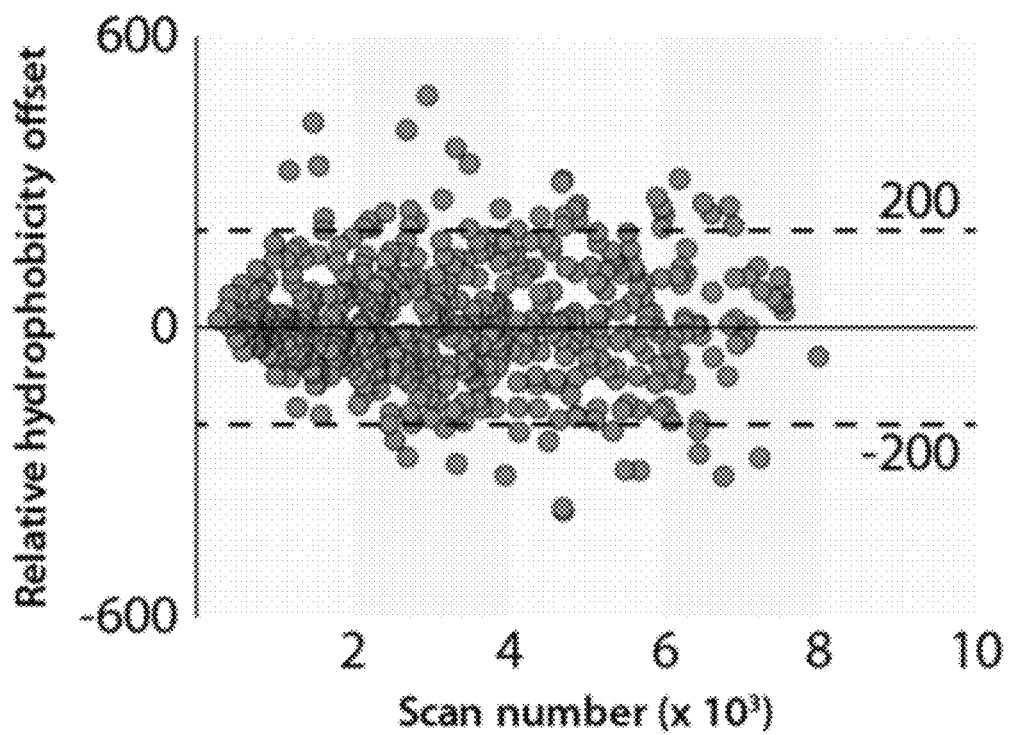
FIG. 10 provides a plot showing the difference between the relative hydrophobicity offset of a given identification and the average of the previous five relative hydrophobicity offsets. 95% of the time this difference is within +/−200 of the predicted value.

Knowing when to look for a target in an LC gradient adds another significant boost to success rate, sensitivity, and duty cycle [88]. Retention time correlates linearly with the hydrophobicity factor (calculated offline with SSRCalc [89]), but the exact relationship can easily vary from run-to-run. Here a novel method is disclosed for scheduling targets by use of rtTC. Specifically, the relative hydrophobicity order (RHO) of real-time detected peptide targets is used to determine which targets are likely to appear next. In place of retention time, commonly used in SRM methods, RHO is used. By scheduling relative to the previously detected peptides, absolute calibration of retention time is not required and run-torun variation is easily accounted for. The scan number is compared to the hydrophobicity factor index (HFI) for the 800 MaeStro1 detected targets from the SRPs described herein. There is a strong correlation between scan number and HFI. The next question is the validity of using the RHO of previously rtTC-detected targets as a predictive measure. FIG. 10 plots the difference between a detected peptide target's RHO and the average RHO of the five previously rtTC-detected targets. Even with this rudimentary approach, predictions within +/−200 RHO units can be made, meaning that without further optimization the number of targets can be reduced to about a third of the overall number (i.e., a target list of 1300 can be truncated to ~400 at any given time). Use of more complex algorithms for real-time RHO calculation can increase the prediction power to +/−100 RHO units.

The overarching goal of the MaeStro1 logic is to reduce the number of failed $MS^2$ events so that the size of the inclusion list can accommodate protein groups up to 1000 or more. It has been demonstrated that by incorporating rtTC throughput can be increased by 2×. Real-time RHO scheduling can deliver another 3× or more. Finally, the OrbiQ hardware itself provides another 3× in duty cycle improvement (i.e., 10 Hz acquisition rate) over the preliminary data acquired on a Velos Orbitrap operating at ~3 Hz.

MaeStro2: Directed Data Acquisition Through $MS^2$ Detection.

While MaeStro1 increases the reproducibility of a proteomic experiment, it does so with similar sensitivity to the current shotgun approach. This is because a signal in $MS^1$ must be observed to trigger the $MS^2$. Peptides generated from proteins of low abundance are often masked by the thousands of other peptides present at much higher abundances [9, 29-31]. The ultimate protein detection sensitivity is achieved by use of SRM strategies where $MS^2$ scans are performed regardless of whether a precursor $MS^1$ signal exists. By allowing only the narrow m/z range the precursor of interest occupies, the resulting spectrum becomes greatly enriched for those species. Gains in sensitivity of 100× are typical of SRM-type approaches; however, the methods suffer from extremely low duty cycle—precluding application to high throughput experiments. It is noted that many of the proteins in a given Gene Ontology group or network are likely to exist at low levels. To achieve the goal of reproducibly detecting such groups the pace and throughput of SRM-type experiments must be advanced. Such an acquisition method—MaeStro2—is disclosed herein to be used in concert with, or independent from, MaeStro1.

MaeStro2 utilizes the rapid scan rate and mass accuracy of the OrbiQ hardware to expand on conventional SRM in grand style. The high resolving power of the OrbiQ allows for the simultaneous collection of all product ion transitions from one or multiple target precursors in an approach called parallel reaction monitoring (PRM). Consider again the 1098 mitochondrial protein targets discussed previously. Tryptic digestion produces 65,033 theoretical peptides. The goal is to detect at least three unique peptides from each of these proteins. Assuming these peptides occupy a precursor m/z range of 1500 Th—one would need to scan 500 3 Th bins to have a chance to see all of them. Several groups have described this type of approach, called data-independent analysis (DIA) [48, 49, 57]. Even with the 10 Hz scan rate of the OrbiQ, one would need to perform each experiment 10-20 times to cover the m/z range just once, assuming each range is sampled every 3 to 5 seconds so as not to miss chromatographic elution profiles. MacCoss, Goodlett, and others have demonstrated that DIA does improve both sensitivity and reproducibility; however, it requires an enormous amount of instrument analysis and, even worse, enormous amounts of sample, which is often not available [48, 49].

MaeStro2 Melds the SRM and DIA Methodologies.

Figure 11:
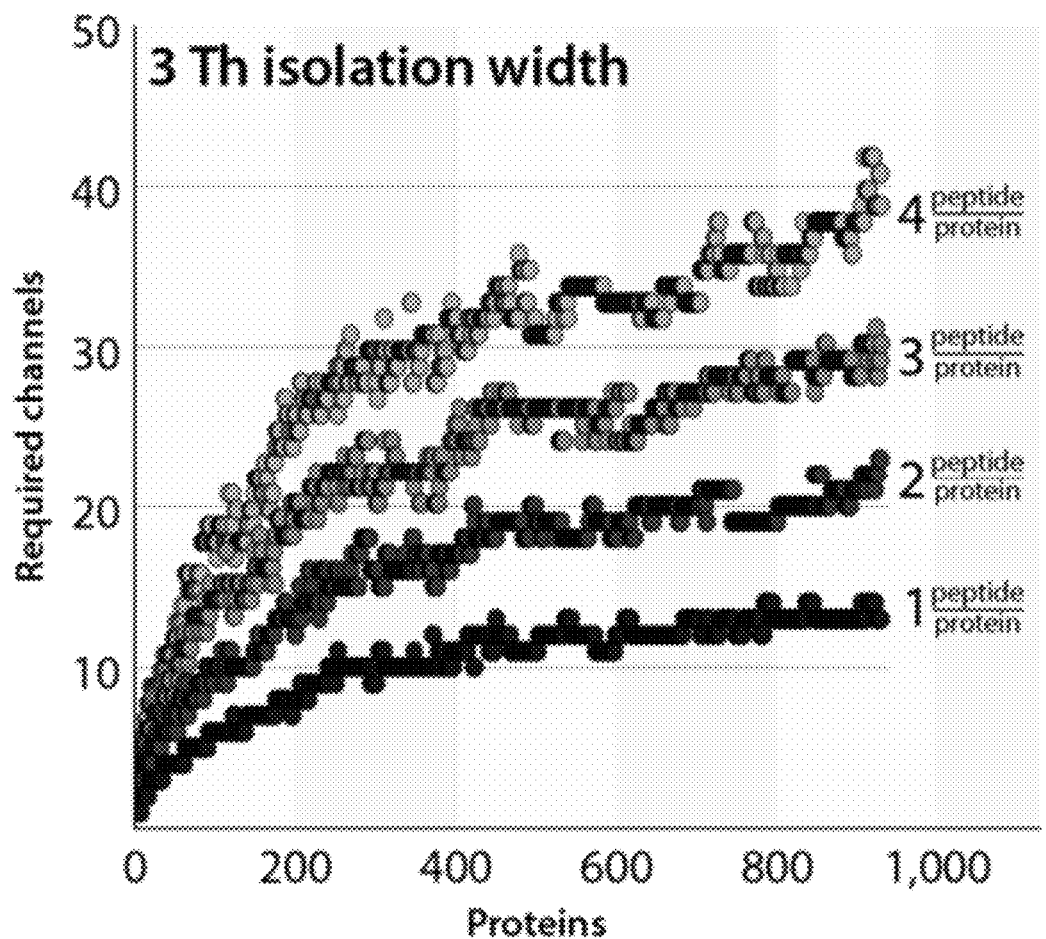
FIG. 11 provides a plot showing the number of channels needed to detect various numbers of the ~1000 mitochondrial proteins using MaeStro2.

First, all 65,003 candidate peptide targets are grouped into defined m/z bins (channels). The channels are then examined to determine the fewest number that can be selected to contain at one, two, three, or four representative peptides per protein. The idea is to select only the minimum number of isolation ranges that contain representative peptide targets of all selected proteins. FIG. 11 presents a calculation of the number of channels needed to represent various numbers of target proteins for a channel width of 3 m/z. From these data it was observed that highly sensitive SRM-type analyses can be performed on at least 4 unique peptides from each of the ~1000 mitochondrial proteins by monitoring just 40 discrete channels. This type of high-throughput SRM experiment is uniquely enabled by the OrbiQ hardware described herein. With a static dwell time of 100 ms, 10 channels can be monitored per second at a resolving power of 10,000. This means that every 4 seconds the cycle is complete and that peaks will be selected multiple times across their elution profile. It should be noted that similar calculations have been performed with various other protein groups and achieved similar numbers of required channels.

Making these calculations with all candidate peptides leads to a potential problem: the need for more channels than the above model predicts. This issue could reduce the number of proteins MaeStro2 can target. Extensive prior research in SRM indicates that success depends on peptide target selection; certain peptides are frequently detected while others from the same protein may never have been observed. In response to this potential problem, it was examined how many of the 1098 mitochondrial proteins have already been mapped by MS. Combining multiple peptide databases, 17,491 peptides from 959 of these targets have been observed for an average of 16.85 peptides/protein. This means that over 90% of the desired proteins to be targeted have been observed before. For the remaining 118, candidate peptide targets are ranked by suitability score (PeptideAtlas, details described herein). The rtTC detection algorithm and the hydrophobicity calculations detailed above (RHO) are also incorporated. As rtTC confirms target peptides, new channels can be included and those that have been drawn down can be removed. Channels can also be grouped by an RHO composite score, such that the channels most likely to produce detected targets are always dynamically in play. All calculations were performed using a 3 m/z bin. Increasing bin width, allowing for increased bandwidth, can cost sensitivity.

Streamlining Proteotypic Peptide Selection for MaeStro1 and MaeStro2.

The Aebersold group curates a database called PeptideAtlas to organize peptides from a given protein that are most likely to be observed [16, 90]. Data can be put into a form compliant with PeptideAtlas [91]. For designing MaeStro directed studies, a target protein list is imported and given each predicted peptide a suitability score. For peptides not contained in the database, scores are predicted using algorithms already in existence in PeptideAtlas and others [92-96]. For MeaStro1, the direct rank order is used to choose targets. For MeaStro2, the direct rank order is used as an additional factor during m/z bin selection.

Reproducibility.

A key motivation for the instrumentation is to deliver proteomic reproducibility that is commensurate with transcriptomics (FIG. 1). This irreproducibility stems from DDA. Recent multiple laboratory proteomic data (DDA) was analyzed for reproducibility and revealed overlap in peptide identifications from replicate pairs ranged from 35-60% [10]. The data acquisition methods disclosed herein draw from SRM, inclusion list, and data independent themes—all of which deliver higher reproducibility by eliminating the stochastic nature of DDA. Preliminary data with basic implementations of MaeStro1 and MaeStro2 on a Velos Orbitrap system indicate excellent reproducibility metrics (~75-87%). The hardware and software concepts disclosed herein can easily boost these numbers to the desired 95% or better range.

Quantification/Fractionation.

Paramount to any new MS method is the ability to obtain quantitative information. Below it is shown how to implement an isobaric tagging strategy; however, the MaeStro control logic can permit creative and useful new opportunities for any type of current quantification approach. rtTC target detection is used to boost quantitative signals. For example, once a peptide target is confirmed MaeStro can trigger a selected ion mass range (SIM) scan to precisely monitor an isotopically labeled pair (e.g., SILAC). This approach can greatly increase the dynamic range and precision over current practice. For isobaric tag-based experiments MaeStro simply triggers a second $MS^2$ scan with a very narrow m/z range so that interfering species do not perturb the quantitative signals. This type of scanning is only done following a confirmation so that the overall cost to duty cycle is low. No change is needed to deliver non isotope-based quantification approaches.

A proteomic trend is the extensive use of fractionation prior to LC-MS/MS. Fractionation can simplify complex peptide mixtures and allow for greater coverage and dynamic range. Ideally, the target list can be updated so that predicted characteristics of each peptide target are mapped to specific fractions. Operation in this manner can deliver significant benefits—mainly that target lists can be tailored to specific fractions. The key here is the ability to predict which candidate targets will be in a given strong cation exchange (SCX) or isoelectric focusing fraction, for instance. Several reports on this topic have appeared recently and these algorithms and their ability to predict target location can be used [97]. Absolute predictive power is needed. For example, if just 50% of targets can be assigned the correct fraction out of 10, a 5× gain is gained in target capacity.

Directed Systems Analysis of Mitochondrial Adaptation to Iron Deprivation.

The OrbiQ platform can be leveraged to monitor the mitochondrial proteomic changes that occur in skeletal muscle cells in response to nutrient stress. This is an ideal experimental subject to investigate with this new technology for a variety of reasons. First, mitochondria are of outstanding importance to human health, with more than 50 diseases now associated with mitochondrial dysfunction. Second, cells adapt to external stresses by altering their mitochondrial infrastructure, but the extent of this restructuring, and the mechanisms that drive this process, are poorly understood. Third, the mitochondrial protein complement is 1098 in number—reproducibly detecting all these proteins across multiple biological replicates is currently not possible with conventional instruments and techniques. In fact, Pagliarini recently led a study that integrated in-depth protein mass spectrometry, microscopy, and machine learning to construct the 1098 protein compendium of the mitochondrion from which this targeted experiment was based [61]. This resource represents the most comprehensive and accurate molecular characterization of the organelle to date.

Figure 12:
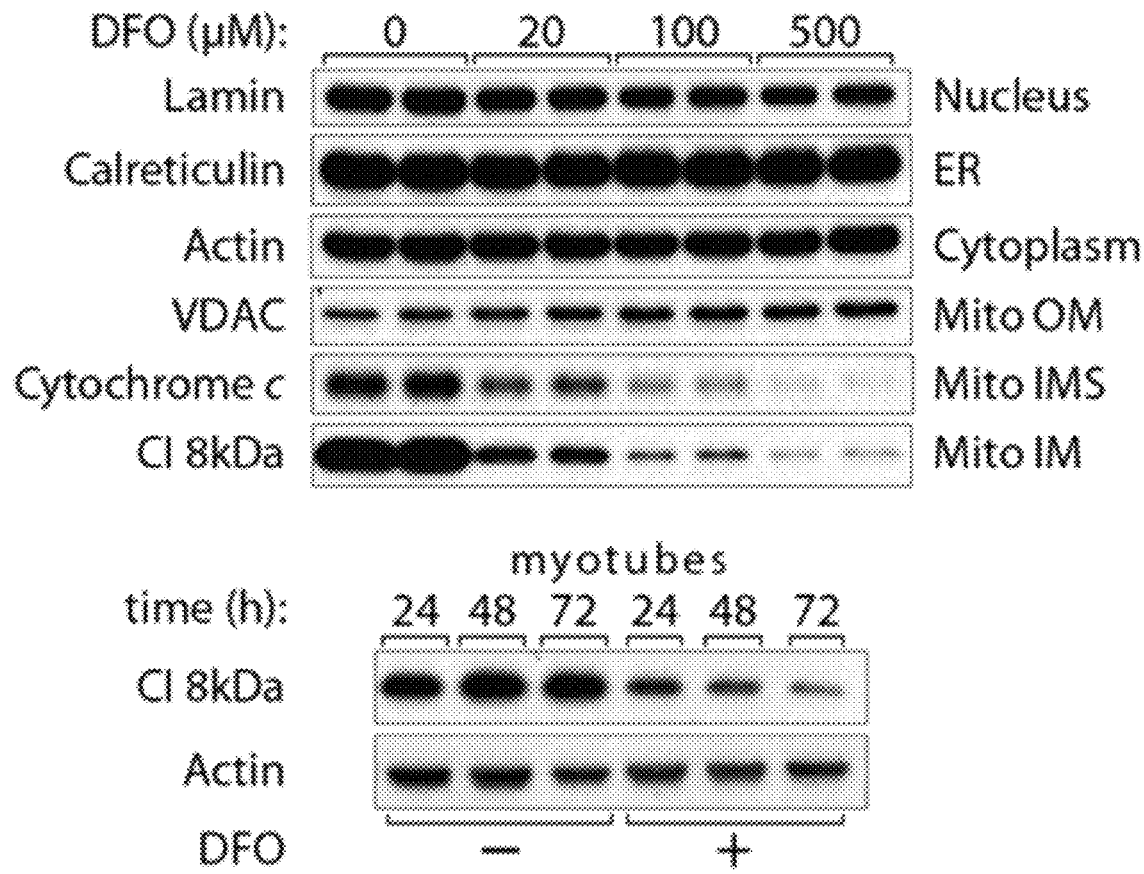
FIG. 12 provides immunoblots revealing the dose-dependent (top) and time-dependent (bottom) loss of mitochondrial proteins following iron chelation.

The mitochondrial proteome alterations that occur in skeletal muscle cells following iron deprivation can be monitored. This experiment is motivated both by the profound importance of iron to mitochondrial function and human health, and by the recent observation that this stress causes a rapid loss of mitochondrial metabolic proteins (FIG. 12). Treatment of mouse skeletal muscle myotubes with the clinically used iron chelator desferrioxamine (DFO) induces loss of proteins involved in mitochondrial oxidative phosphorylation (OXPHOS) in both a dose-dependent and time-dependent manner. However, not all mitochondrial proteins are affected by this stress, as evidenced by the unchanging levels of the mitochondrial voltage dependent anion channel (VDAC) in FIG. 12. And, for a subset of genes analyzed, changes in mRNA levels are not concordant with changes in protein levels, indicating that genomic technologies alone cannot capture these phenomena (FIG. 7). The present data suggest that remodeling of the mitochondrial proteome is a key process in cellular adaptation to iron deprivation, and, that this adaptation involves undefined post-transcriptional processes.

Cell Culture/Treatment.

Figure 13:
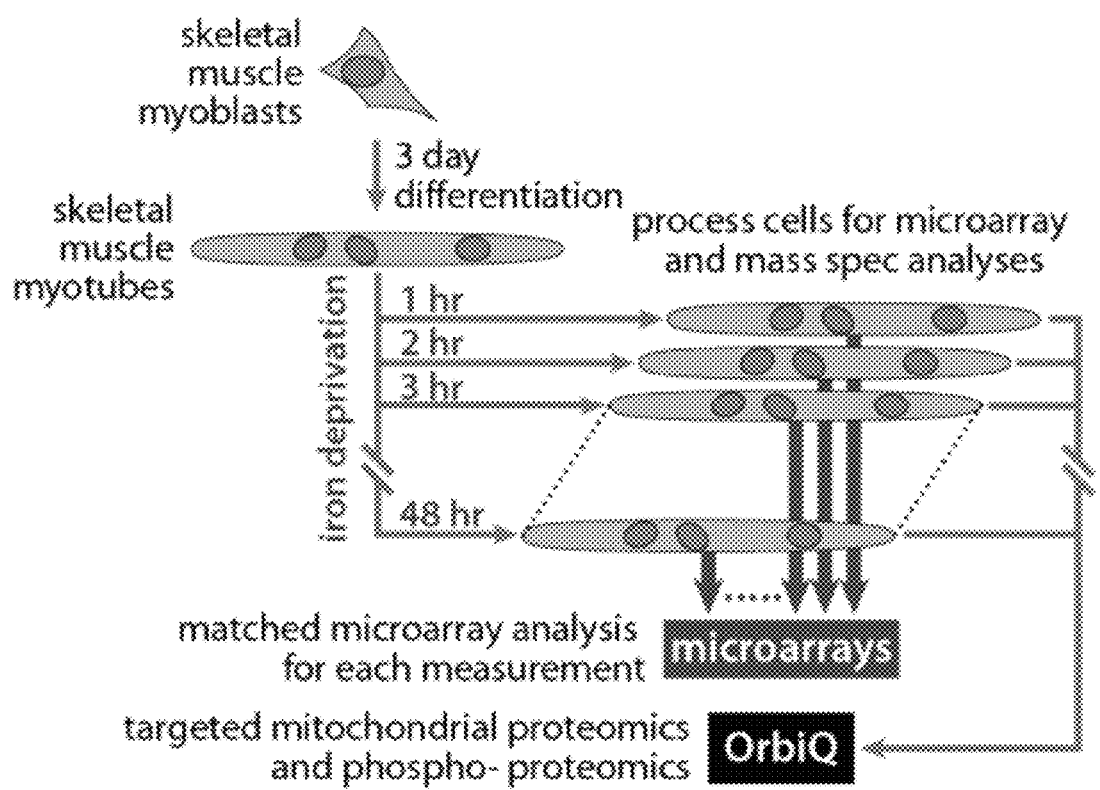
FIG. 13 provides a flow diagram showing the experimental design for mitochondrial protein analysis as described herein.

To elucidate the extent of mitochondrial proteome adaptation to iron deprivation, matched proteomic and microarray analyses of iron deprived mouse myotube C2C12 cells were performed. First, myoblasts were differentiated into myotubes via growth in low serum media for three days (FIG. 13). These mature myotubes serve as models for post-mitotic skeletal muscle, whose function is particularly affected by low iron levels. Following differentiation, the cells were treated with 100 µM DFO—a sufficient amount to cause a marked decrease in mitochondrial proteins at 24 hrs (FIG. 12) without causing cell death. Using these cells, transcript and protein dynamics were compared at 8 treatment time points: 0, 1, 2, 4, 8, 12, 24, and 48 hours. Iron depletion causes rapid down-regulation of cytosolic proteins via mRNA binding proteins [67, 68] and is also linked to a number of more extensive transcriptional responses [98]. Observation of this time range allows iron deprivation-induced transcriptional events from post-transcriptional events to be distinguished. The experiments can also reveal the mitochondrial modifications that occur during both acute and chronic stress.

Analysis.

The mRNA and protein abundances for each of the 1098 genes specific to the mitochondria were measured from five biological replicates per time point. mRNA can be measured by microarray. Protein measurements can be accomplished by use of 8-plex isobaric tags (iTRAQ). This methodology is entirely compatible with the OrbiQ platform. Using MaeStro, the 1098 mitochondrial proteins were targeted with high precision and reproducibility. All targeted MS data can be subject to standard post-acquisition database searching using a decoy database to establish a 1% FDR cutoff.

Data Analysis.

Figure 14:
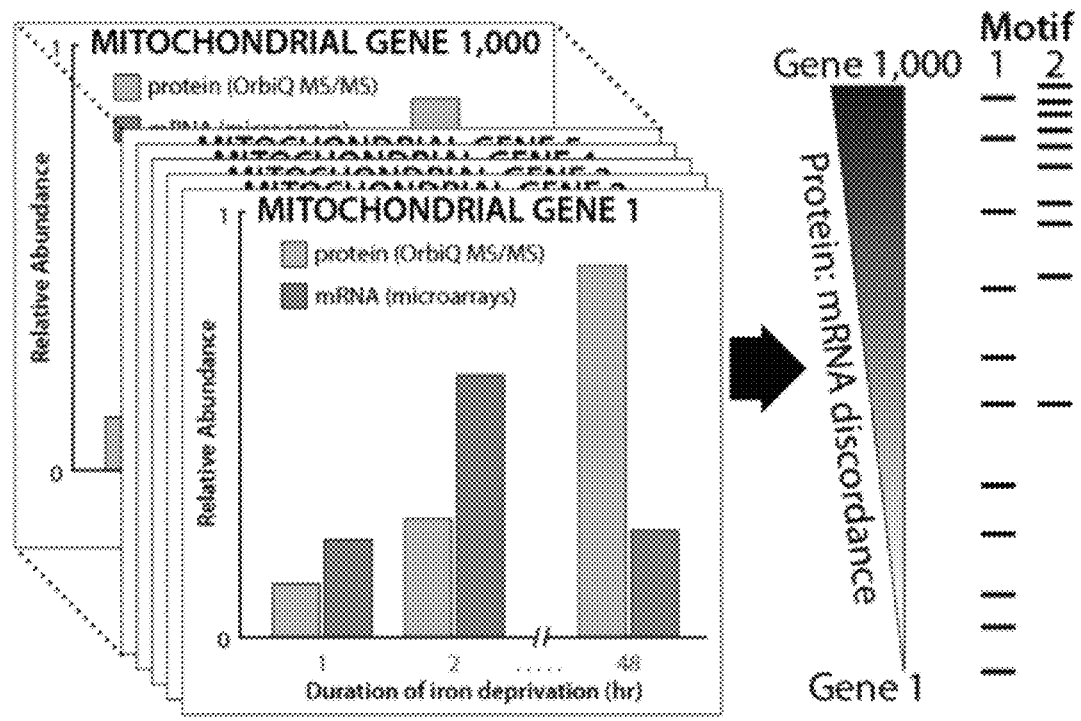
FIG. 14 provides a depiction of the computational approach for identifying mRNA motifs involved in post-transcriptional regulatory mechanisms FIG. 15 provides a flow diagram showing: a Full MS1 scan having a SILAC pair in which the heavy ion is on a target acquisition list in panel A; the step of examining the signal-to-noise ratio of the least intense SILAC peak pair in panel B; narrowing the MS1 scan window to increase the signal-to-noise ratio of the SILAC pair peaks in panel C; and re-examining the signal-to-noise of the SILAC pair peaks in panel D.

With these data, direct comparisons can be made between transcript and protein across all conditions. Using this strategy, it is possible to: (1) elucidate the specific mitochondrial proteins and pathways that are affected by iron deficiency and (2) directly assess the relationship between mRNA and protein levels. Concordance in the magnitude and direction of changes for mRNA and protein suggests that changes in gene expression due to iron loss are driven primarily by transcription. Discordance, on the other hand, indicates the involvement of post-transcriptional regulation. In these cases the regulatory mRNA elements responsible can be identified (FIG. 14). To do this, both novel short motifs and well-characterized, longer motifs were searched. First, all mitochondrial genes are ranked based on level of concordance and search for the presence of short (6-10 bp) conserved motifs in mRNA UTRs of these genes using a computational algorithm [99] (FIG. 14). Motifs that preferentially associate with the discordant genes can be considered candidate mRNA regulatory motifs. Longer mRNA regulatory elements, such as uORFs, iron response elements (IREs), and internal ribosomal entry sites (IRESs), as well as the ~50 well-characterized short UTR motifs, can also be examined using computational tools freely available online [100]. Based on the past performance of this computation approach, and the mounting implications of post-transcriptional control of gene expression, these approaches can lead to the identification of mRNA regulatory motifs important for the expression of mitochondrial proteins in response to iron deprivation. The functionality of high-scoring motifs can be validated using quantitative PCR and luminometry, as has been performed previously [101].

Rationale for Quintuplicate Measurement.

Sensitive detection of regulated genes and proteins requires multiple biological replicate measurements—the whole basis for the growing directed MS field. Conducting experiments in biological quintuplicate ensures a detection of a 50% change between any two gene products with 95% probability at standard deviation of 20% or less. Experiments performed in quintuplicate, using iTRAQ, revealed that 75 to 90% of transcripts and proteins changing by 1.5 fold or more meet these criteria and represent statistically significant events. The key value of the replicate measurement is to provide an assessment of significance for nearly all monitored genes. To correct for multiple hypothesis testing and to further improve statistical power, FDR is computed by conducting a combined analysis of the mRNA and protein levels using SAM [102, 103]. This analysis allows comparison between protein and mRNA levels at one given time point and allows testing for changes in trends over time.

REFERENCES FOR EXAMPLE 1

1. C. E. Parker, T. W. Pearson, N. L. Anderson, and C. H. Borchers, *Mass-spectrometry-based clinical proteomics—a review and prospective*. Analyst, 2010. 135 (8): p. 1830-1838.
2. D. S. Kirkpatrick, S. A. Gerber, and S. P. Gygi, *The absolute quantification strategy: a general procedure for the quantification of proteins and post-translational modifications*. Methods, 2005. 35 (3): p. 265-273.
3. D. Phanstiel, R. Unwin, G. C. McAlister, and J. J. Coon, *Peptide Quantification Using 8-Plex Isobaric Tags and Electron Transfer Dissociation Tandem Mass Spectrometry*. Analytical Chemistry, 2009. 81 (4): p. 1693-1698.
4. C. C. Wu, M. J. MacCoss, K. E. Howell, D. E. Matthews, and J. R. Yates, *Metabolic labeling of mammalian organisms with stable isotopes for quantitative proteomic analysis*. Analytical Chemistry, 2004. 76 (17): p. 4951-4959.
5. S. E. Ong, B. Blagoev, I. Kratchmarova, D. B. Kristensen, H. Steen, A. Pandey, and M. Mann, *Stable isotope labeling by amino acids in cell culture, SILAC, as a simple and accurate approach to expression proteomics*. Molecular & Cellular Proteomics, 2002. 1 (5): p. 376-386.
6. H. N. Zhu, S. Q. Pan, S. Gu, E. M. Bradbury, and X. Chen, *Amino acid residue specific stable isotope labeling for quantitative proteomics*. Rapid Communications in Mass Spectrometry, 2002. 16 (22): p. 2115-2123.
7. P. Mallick and B. Kuster, *Proteomics: a pragmatic perspective*. Nature Biotechnology, 2010. 28 (7): p. 695-709.
8. J. Grossmann, B. Roschitzki, C. Panse, C. Fortes, S. Barkow-Oesterreicher, D. Rutishauser, and R. Schlapbach, *Implementation and evaluation of relative and absolute quantification in shotgun proteomics with label-free methods*. Journal of Proteomics, 2010. 73 (9): p. 1740-1746.
9. H. B. Liu, R. G. Sadygov, and J. R. Yates, *A model for random sampling and estimation of relative protein abundance in shotgun proteomics*. Analytical Chemistry, 2004. 76 (14): p. 4193-4201.
10. D. L. Tabb, L. Vega-Montoto, P. A. Rudnick, A. M. Variyath, A. J. L. Ham, D. M. Bunk, L. E. Kilpatrick, D. D. Billheimer, R. K. Blackman, H. L. Cardasis, S. A. Carr, K. R. Clauser, J. D. Jaffe, K. A. Kowalski, T. A. Neubert, F. E. Regnier, B. Schilling, T. J. Tegeler, M. Wang, P. Wang, J. R. Whiteaker, L. J. Zimmerman, S. J. Fisher, B. W. Gibson, C. R. Kinsinger, M. Mesri, H. Rodriguez, S. E. Stein, P. Tempst, A. G. Paulovich, D.C. Liebler, and C. Spiegelman, *Repeatability and Reproducibility in Proteomic Identifications by Liquid Chromatography-Tandem Mass Spectrometry*. Journal of Proteome Research, 2010. 9 (2): p. 761-776.
11. M. K. Gupta, J. W. Jung, S. J. Uhm, H. Lee, H. T. Lee, and K. P. Kim, *Combining selected reaction monitoring with discovery proteomics in limited biological samples*. Proteomics, 2009. 9 (21): p. 4834-4836.
12. X. Yang and I. M. Lazar, *MRM screening/biomarker discovery with linear ion trap MS: a library of human cancer-specific peptides*. Bmc Cancer, 2009. 9.
13. A. Schmidt, N. Gehlenborg, B. Bodenmiller, L. N. Mueller, D. Campbell, M. Mueller, R. Aebersold, and B. Domon, *An Integrated, Directed Mass Spectrometric Approach for In-depth Characterization of Complex Peptide Mixtures*. Molecular & Cellular Proteomics, 2008. 7 (11): p. 2138-2150.
14. A. Schmidt, M. Claassen, and R. Aebersold, *Directed mass spectrometry: towards hypothesis-driven proteomics*. Current Opinion in Chemical Biology, 2009. 13 (5-6): p. 510-517.
15. T. A. Addona, S. E. Abbatiello, B. Schilling, S. J. Skates, D. R. Mani, D. M. Bunk, C. H. Spiegelman, L. J. Zimmerman, A. J. L. Ham, H. Keshishian, S. C. Hall, S. Allen, R. K. Blackman, C. H. Borchers, C. Buck, H. L. Cardasis, M. P. Cusack, N. G. Dodder, B. W. Gibson, J. M. Held, T. Hiltke, A. Jackson, E. B. Johansen, C. R. Kinsinger, J. Li, M. Mesri, T. A. Neubert, R. K. Niles, T. C. Pulsipher, D. Ransohoff, H. Rodriguez, P. A. Rudnick, D. Smith, D. L. Tabb, T. J. Tegeler, A. M. Variyath, L. J. Vega-Montoto, A. Wahlander, S. Waldemarson, M. Wang, J. R. Whiteaker, L. Zhao, N. L. Anderson, S. J. Fisher, D. C. Liebler, A. G. Paulovich, F. E. Regnier, P. Tempst, and S. A. Carr, *Multi-site assessment of the precision and reproducibility of multiple reaction monitoring-based measurements of proteins in plasma*. Nature Biotechnology, 2009. 27 (7): p. 633-U85.
16. V. Lange, P. Picotti, B. Domon, and R. Aebersold, *Selected reaction monitoring for quantitative proteomics: a tutorial*. Molecular Systems Biology, 2008. 4.
17. P. Picotti, O. Rinner, R. Stallmach, F. Dautel, T. Farrah, B. Domon, H. Wenschuh, and R. Aebersold, *High-throughput generation of selected reaction-monitoring assays for proteins and proteomes*. Nature Methods, 2010. 7 (1): p. 43-U5.
18. J. Sherman, M. J. McKay, K. Ashman, and M. P. Molloy, *How specific is my SRM?: The issue of precursor and product ion redundancy*. Proteomics, 2009. 9 (5): p. 1120-1123.
19. M. W. Duncan, A. L. Yergey, and S. D. Patterson, *Quantifying proteins by mass spectrometry: The selectivity of SRM is only part of the problem*. Proteomics, 2009. 9 (5): p. 1124-1127.
20. R. D. Baynes and T. H. Bothwell, *Iron deficiency*. Annu Rev Nutr, 1990. 10: p. 133-48.

21. S. Matallana-Surget, B. Leroy, and R. Wattiez, *Shotgun proteomics: concept, key points and data mining.* Expert Review of Proteomics, 2010. 7 (1): p. 5-7.
22. C. C. Wu and M. J. MacCoss, *Shotgun proteomics: Tools for the analysis of complex biological systems.* Current Opinion in Molecular Therapeutics, 2002. 4 (3): p. 242-250.
23. G. C. McAlister, D. Phanstiel, C. D. Wenger, M. V. Lee, and J. J. Coon, *Analysis of Tandem Mass Spectra by FTMS for Improved Large-Scale Proteomics with Superior Protein Quantification.* Analytical Chemistry, 2010. 82 (1): p. 316-322.
24. J. K. Eng, A. L. McCormack, and J. R. Yates, *AN APPROACH TO CORRELATE TANDEM MASS-SPECTRAL DATA OF PEPTIDES WITH AMINO-ACID-SEQUENCES IN A PROTEIN DATABASE.* Journal of the American Society for Mass Spectrometry, 1994. 5 (11): p. 976-989.
25. D. N. Perkins, D. J. C. Pappin, D. M. Creasy, and J. S. Cottrell, *Probability-based protein identification by searching sequence databases using mass spectrometry data.* Electrophoresis, 1999. 20 (18): p. 3551-3567.
26. L. Y. Geer, S. P. Markey, J. A. Kowalak, L. Wagner, M. Xu, D. M. Maynard, X. Y. Yang, W. Y. Shi, and S. H. Bryant, *Open mass spectrometry search algorithm.* Journal of Proteome Research, 2004. 3 (5): p. 958-964.
27. A. Thompson, J. Schafer, K. Kuhn, S. Kienle, J. Schwarz, G. Schmidt, T. Neumann, and C. Hamon, *Tandem mass tags: A novel quantification strategy for comparative analysis of complex protein mixtures by MS/MS.* Analytical Chemistry, 2003. 75 (8): p. 1895-1904.
28. P. L. Ross, Y. L. N. Huang, J. N. Marchese, B. Williamson, K. Parker, S. Hattan, N. Khainovski, S. Pillai, S. Dey, S. Daniels, S. Purkayastha, P. Juhasz, S. Martin, M. Bartlet-Jones, F. He, A. Jacobson, and D. J. Pappin, *Multiplexed protein quantitation in Saccharomyces cerevisiae using amine-reactive isobaric tagging reagents.* Molecular & Cellular Proteomics, 2004. 3 (12): p. 1154-1169.
29. A. Ducret, I. Van Oostveen, J. K. Eng, J. R. Yates, and R. Aebersold, *High throughput protein characterization by automated reverse-phase chromatography electrospray tandem mass spectrometry.* Protein Science, 1998. 7 (3): p. 706-719.
30. A. J. Link, J. Eng, D. M. Schieltz, E. Carmack, G. J. Mize, D. R. Morris, B. M. Garvik, and J. R. Yates, *Direct analysis of protein complexes using mass spectrometry.* Nature Biotechnology, 1999. 17 (7): p. 676-682.
31. C. C. Wu, M. J. MacCoss, K. E. Howell, and J. R. Yates, *A method for the comprehensive proteomic analysis of membrane proteins.* Nature Biotechnology, 2003. 21 (5): p. 532-538.
32. J. V. Olsen, M. Vermeulen, A. Santamaria, C. Kumar, M. L. Miller, L. J. Jensen, F. Gnad, J. Cox, T. S. Jensen, E. A. Nigg, S. Brunak, and M. Mann, *Quantitative Phosphoproteomics Reveals Widespread Full Phosphorylation Site Occupancy During Mitosis.* Science Signaling, 2010. 3 (104).
33. A. Moritz, Y. Li, A. L. Guo, J. Villen, Y. Wang, J. MacNeill, J. Kornhauser, K. Sprott, J. Zhou, A. Possemato, J. M. Ren, P. Hornbeck, L. C. Cantley, S. P. Gygi, J. Rush, and M. J. Comb, *Akt-RSK-S6 Kinase Signaling Networks Activated by Oncogenic Receptor Tyrosine Kinases.* Science Signaling, 2010. 3 (136).
34. F. S. Oppermann, F. Gnad, J. V. Olsen, R. Hornberger, Z. Greff, G. Keri, M. Mann, and H. Daub, *Large-scale Proteomics Analysis of the Human Kinome.* Molecular & Cellular Proteomics, 2009. 8 (7): p. 1751-1764.
35. J. R. Wisniewski, A. Zougman, N. Nagaraj, and M. Mann, *Universal sample preparation method for proteome analysis.* Nature Methods, 2009. 6 (5): p. 359-U60.
36. G. Manning, D. B. Whyte, R. Martinez, T. Hunter, and S. Sudarsanam, *The protein kinase complement of the human genome.* Science, 2002. 298 (5600): p. 1912-+.
37. M. Ashburner, C. A. Ball, J. A. Blake, D. Botstein, H. Butler, J. M. Chemy, A. P. Davis, K. Dolinski, S. S. Dwight, J. T. Eppig, M. A. Harris, D. P. Hill, L. Issel-Tarver, A. Kasarskis, S. Lewis, J. C. Matese, J. E. Richardson, M. Ringwald, G. M. Rubin, G. Sherlock, and C. Gene Ontology, *Gene Ontology: tool for the unification of biology.* Nature Genetics, 2000. 25 (1): p. 25-29.
38. K. Busch, *Mass spectrometry forum—Space charge in mass spectrometry.* Spectroscopy, 2004. 19 (6): p. 35-38.
39. F. Rocher, A. Favre, F. Gonnet, and J. C. Tabet, *Study of ghost peaks resulting from space charge and non-linear fields in an ion trap mass spectrometer.* Journal of Mass Spectrometry, 1998. 33 (10): p. 921-935.
40. M. E. Belov, E. N. Nikolaev, R. Harkewicz, C. D. Masselon, K. Alving, and R. D. Smith, *Ion discrimination during ion accumulation in a quadrupole interface external to a Fourier transform ion cyclotron resonance mass spectrometer.* International Journal of Mass Spectrometry, 2001. 208 (1-3): p. 205-225.
41. J. P. Murphy and R. A. Yost, *Origin of mass shifts in the quadrupole ion trap: dissociation of fragile ions observed with a hybrid ion trap/mass filter instrument.* Rapid Communications in Mass Spectrometry, 2000. 14 (4): p. 270-273.
42. K. A. Cox, C. D. Cleven, and R. G. Cooks, *MASS SHIFTS AND LOCAL SPACE-CHARGE EFFECTS OBSERVED IN THE QUADRUPOLE ION-TRAP AT HIGHER RESOLUTION.* International Journal of Mass Spectrometry and Ion Processes, 1995. 144 (1-2): p. 47-65.
43. H. Wang, T. Chang-Wong, H. Y. Tang, and D. W. Speicher, *Comparison of Extensive Protein Fractionation and Repetitive LC-MS/MS Analyses on Depth of Analysis for Complex Proteomes.* Journal of Proteome Research, 2010. 9 (2): p. 1032-1040.
44. A. Izrael-Tomasevic, L. Phu, Q. T. Phung, J. R. Lill, and D. Arnott, *Targeting Interferon Alpha Subtypes in Serum: A Comparison of Analytical Approaches to the Detection and Quantitation of Proteins in Complex Biological Matrices.* Journal of Proteome Research, 2009. 8 (6): p. 3132-3140.
45. P. Picotti, B. Bodenmiller, L. N. Mueller, B. Domon, and R. Aebersold, *Full Dynamic Range Proteome Analysis of S. cerevisiae by Targeted Proteomics.* Cell, 2009. 138 (4): p. 795-806.
46. S. Wienkoop and W. Weckwerth, *Relative and absolute quantitative shotgun proteomics: targeting low-abundance proteins in Arabidopsis thaliana.* Journal of Experimental Botany, 2006. 57 (7): p. 1529-1535.
47. A. Zerck, E. Nordhoff, A. Resemann, E. Mirgorodskaya, D. Suckau, K. Reinert, H. Lehrach, and J. Gobom, *An Iterative Strategy for Precursor Ion Selection for LC-MS/MS Based Shotgun Proteomics.* Journal of Proteome Research, 2009. 8 (7): p. 3239-3251.
48. M. Bern, G. Finney, M. R. Hoopmann, G. Merrihew, M. J. Toth, and M. J. MacCoss, *Deconvolution of Mixture Spectra from Ion-Trap Data-Independent-Acquisition Tandem Mass Spectrometry.* Analytical Chemistry, 2010. 82 (3): p. 833-841.
49. A. Panchaud, A. Scherl, S. A. Shaffer, P. D. von Haller, H. D. Kulasekara, S. I. Miller, and D. R. Goodlett, *Precursor Acquisition Independent From Ion Count: How to Dive*

50. K. Blackburn, F. Mbeunkui, S. K. Mitra, T. Mentzel, and M. B. Goshe, *Improving Protein and Proteome Coverage through Data-Independent Multiplexed Peptide Fragmentation.* Journal of Proteome Research, 2010. 9 (7): p. 3621-3637.

51. E. L. Rudomin, S. A. Carr, and J. D. Jaffe, *Directed Sample Interrogation Utilizing an Accurate Mass Exclusion-Based Data-Dependent Acquisition Strategy (AMEx).* Journal of Proteome Research, 2009. 8 (6): p. 3154-3160.

52. J. D. Jaffe, H. Keshishian, B. Chang, T. A. Addona, M. A. Gillette, and S. A. Carr, *Accurate Inclusion Mass Screening A BRIDGE FROM UNBIASED DISCOVERY TO TARGETED ASSAY DEVELOPMENT FOR BIOMARKER VERIFICATION.* Molecular & Cellular Proteomics, 2008. 7 (10): p. 1952-1962.

53. P. Picotti, R. Aebersold, and B. Domon, *The implications of proteolytic background for shotgun proteomics.* Molecular & Cellular Proteomics, 2007. 6 (9): p. 1589-1598.

54. C. Sandhu, J. A. Newel, G. Badis, S. Talukder, J. Liu, T. R. Hughes, and A. Emili, *Evaluation of data-dependent versus targeted shotgun proteomic approaches for monitoring transcription factor expression in breast cancer.* Journal of Proteome Research, 2008. 7 (4): p. 1529-1541.

55. A. Scherl, S. A. Shaffer, G. K. Taylor, H. D. Kulasekara, S. I. Miller, and D. R. Goodlett, *Genome-specific gas-phase fractionation strategy for improved shotgun proteomic profiling of proteotypic peptides.* Analytical Chemistry, 2008. 80 (4): p. 1182-1191.

56. J. Kennedy and E. G. Yi, *Use of gas-phase fractionation to increase protein identifications: application to the peroxisome.* Methods Mol Biol, 2008. 432: p. 217-28.

57. J. D. Venable, M. Q. Dong, J. Wohlschlegel, A. Dillin, and J. R. Yates, *Automated approach for quantitative analysis of complex peptide mixtures from tandem mass spectra.* Nature Methods, 2004. 1 (1): p. 39-45.

58. S. DiMauro and E. A. Schon, *Mitochondrial respiratory-chain diseases.* N Engl J Med, 2003. 348 (26): p. 2656-68.

59. B. B. Lowell and G. I. Shulman, *Mitochondrial dysfunction and type 2 diabetes.* Science, 2005. 307 (5708): p. 384-7.

60. D. C. Wallace, *A mitochondrial paradigm of metabolic and degenerative diseases, aging, and cancer: a dawn for evolutionary medicine.* Annu Rev Genet, 2005. 39: p. 359-407.

61. D. J. Pagliarini, S. E. Calvo, B. Chang, S. A. Sheth, S. B. Vafai, S. E. Ong, G. A. Walford, C. Sugiana, A. Boneh, W. K. Chen, D. E. Hill, M. Vidal, J. G. Evans, D. R. Thorburn, S. A. Carr, and V. K. Mootha, *A mitochondrial protein compendium elucidates complex I disease biology.* Cell, 2008. 134 (1): p. 112-23.

62. P. Puigserver, Z. Wu, C. W. Park, R. Graves, M. Wright, and B. M. Spiegelman, *A cold-inducible coactivator of nuclear receptors linked to adaptive thermogenesis.* Cell, 1998. 92 (6): p. 829-39.

63. C. Pecqueur, M. G. Alves-Guerra, C. Gelly, C. Levi-Meyrueis, E. Couplan, S. Collins, D. Ricquier, F. Bouillaud, and B. Miroux, *Uncoupling protein 2, in vivo distribution, induction upon oxidative stress, and evidence for translational regulation.* J Biol Chem, 2001. 276 (12): p. 8705-12.

64. X. Perez-Martinez, S. A. Broadley, and T. D. Fox, *Mss51p promotes mitochondrial Cox1p synthesis and interacts with newly synthesized Cox1p.* Embo J, 2003. 22 (21): p. 5951-61.

65. J. I. Piruat and J. Lopez-Barneo, *Oxygen tension regulates mitochondrial DNA-encoded complex I gene expression.* J Biol Chem, 2005. 280 (52): p. 42676-84.

66. F. Mignone, C. Gissi, S. Liuni, and G. Pesole, *Untranslated regions of mRNAs.* Genome Biol, 2002. 3 (3): p. REVIEWS0004.

67. J. L. Casey, M. W. Hentze, D. M. Koeller, S. W. Caughman, T. A. Rouault, R. D. Klausner, and J. B. Harford, *Iron-responsive elements: regulatory RNA sequences that control mRNA levels and translation.* Science, 1988. 240 (4854): p. 924-8.

68. S. Puig, E. Askeland, and D. J. Thiele, *Coordinated remodeling of cellular metabolism during iron deficiency through targeted mRNA degradation.* Cell, 2005. 120 (1): p. 99-110.

69. T. P. Second, J. D. Blethrow, J. C. Schwartz, G. E. Merrihew, M. J. MacCoss, D. L. Swaney, J. D. Russell, J. J. Coon, and V. Zabrouskov, *Dual-Pressure Linear Ion Trap Mass Spectrometer Improving the Analysis of Complex Protein Mixtures.* Analytical Chemistry, 2009. 81 (18): p. 7757-7765.

70. G. C. McAlister, W. T. Berggren, J. Griep-Raming, S. Horning, A. Makarov, D. Phanstiel, G. Stafford, D. L. Swaney, J. E. P. Syka, V. Zabrouskov, and J. J. Coon, *A proteomics grade electron transfer dissociation-enabled hybrid linear ion trap-orbitrap mass spectrometer.* Journal of Proteome Research, 2008. 7 (8): p. 3127-3136.

71. D. L. Swaney, G. C. McAlister, and J. J. Coon, *Decision tree-driven tandem mass spectrometry for shotgun proteomics.* Nature Methods, 2008. 5 (11): p. 959-964.

72. D. K. Williams, G. C. McAlister, D. M. Good, J. J. Coon, and D. C. Muddiman, *Dual electrospray ion source for electron-transfer dissociation on a hybrid linear ion trap-orbitrap mass spectrometer.* Analytical Chemistry, 2007. 79: p. 7916-7919.

73. G. C. McAlister, D. Phanstiel, D. M. Good, W. T. Berggren, and J. J. Coon, *Implementation of electron-transfer dissociation on a hybrid linear ion trap-orbitrap mass spectrometer.* Analytical Chemistry, 2007. 79 (10): p. 3525-3534.

74. D. L. Swaney, G. C. McAlister, M. Wirtala, J. C. Schwartz, J. E. P. Syka, and J. J. Coon, *Supplemental activation method for high-efficiency electron-transfer dissociation of doubly protonated peptide precursors.* Analytical Chemistry, 2007. 79 (2): p. 477-485.

75. P. A. Grimsrud, D. den Os, C. D. Wenger, D. L. Swaney, D. Schwartz, M. R. Sussman, J. M. Ane, and J. J. Coon, *Large-Scale Phosphoprotein Analysis in Medicago truncatula Roots Provides Insight into in Vivo Kinase Activity in Legumes.* Plant Physiology, 2010. 152 (1): p. 19-28.

76. M. Haubitz, D. M. Good, A. Woywodt, H. Haller, H. Rupprecht, D. Theodorescu, M. Dakna, J. J. Coon, and H. Mischak, *Identification and Validation of Urinary Biomarkers for Differential Diagnosis and Evaluation of Therapeutic Intervention in Anti-neutrophil Cytoplasmic Antibody-associated Vasculitis.* Molecular & Cellular Proteomics, 2009. 8 (10): p. 2296-2307.

77. D. L. Swaney, C. D. Wenger, and J. J. Coon, *Value of Using Multiple Proteases for Large-Scale Mass Spectrometry-Based Proteomics.* Journal of Proteome Research, 2010. 9 (3): p. 1323-1329.

78. C. D. Wenger, G. C. McAlister, Q. W. Xia, and J. J. Coon, *Sub-part-per-million Precursor and Product Mass Accuracy for High-throughput Proteomics on an Electron Transfer Dissociation-enabled Orbitrap Mass Spectrometer.* Molecular & Cellular Proteomics, 2010. 9 (5): p. 754-763.

79. S. J. Duellman, K. L. Thompson, J. J. Coon, and R. R. Burgess, *Phosphorylation sites of Epstein-Barr virus EBNA1 regulate its function.* Journal of General Virology, 2009. 90: p. 2251-2259.
80. J. V. McGivern, D. L. Swaney, J. J. Coon, and M. D. Sheets, *Toward Defining the Phosphoproteome of Xenopus laevis Embryos.* Developmental Dynamics, 2009. 238 (6): p. 1433-1443.
81. D. Phanstiel, J. Brumbaugh, G. C. McAlister, C. D. Wenger, R. Stewart, S. Tian, J. A. Thomson, and J. J. Coon, *New Technology for the Large-scale Proteomic Comparison of Human Embryonic Stem Cells, Induced Pluripotent Stem Cells, and Somatic Cells.* Molecular & Cellular Proteomics, 2009: p. S11-S11.
82. D. L. Swaney, C. D. Wenger, J. A. Thomson, and J. J. Coon, *Human embryonic stem cell phosphoproteome revealed by electron transfer dissociation tandem mass spectrometry.* Proceedings of the National Academy of Sciences of the United States of America, 2009. 106 (4): p. 995-1000.
83. S. Lecchi, C. J. Nelson, K. E. Allen, D. L. Swaney, K. L. Thompson, J. J. Coon, M. R. Sussman, and C. W. Slayman, *Tandem phosphorylation of Ser-911 and Thr-912 at the C terminus of yeast plasma membrane H+-ATPase leads to glucose-dependent activation.* Journal of Biological Chemistry, 2007. 282 (49): p. 35471-35481.
84. D. Phanstiel, J. Brumbaugh, W. T. Berggren, K. Conard, X. Feng, M. E. Levenstein, G. C. McAlister, J. A. Thomson, and J. J. Coon, *Mass spectrometry identifies and quantifies 74 unique histone H4 isoforms in differentiating human embryonic stem cells.* Proceedings of the National Academy of Sciences of the United States of America, 2008. 105 (11): p. 4093-4098.
85. A. Chi, C. Huttenhower, L. Y. Geer, J. J. Coon, J. E. P. Syka, D. L. Bai, J. Shabanowitz, D. J. Burke, O. G. Troyanskaya, and D. F. Hunt, *Analysis of phosphorylation sites on proteins from Saccharomyces cerevisiae by electron transfer dissociation (ETD) mass spectrometry.* Proceedings of the National Academy of Sciences of the United States of America, 2007. 104 (7): p. 2193-2198.
86. N. Khidekel, S. B. Ficarro, P. M. Clark, M. G. Bryan, D. L. Swaney, J. E. Rexach, Y. E. Sun, J. J. Coon, E. G. Peters, and L. C. Hsieh-Wilson, *Probing the dynamics of O-GlcNAc glycosylation in the brain using quantitative proteomics.* Nature Chemical Biology, 2007. 3 (6): p. 339-348.
87. E. L. Huttlin, A. D. Hegeman, A. G. Harms, and M. R. Sussman, *Prediction of error associated with false-positive rate determination for peptide identification in large-scale proteomics experiments using a combined reverse and forward peptide sequence database strategy.* Journal of Proteome Research, 2007. 6 (1): p. 392-398.
88. O. V. Krokhin, S. Ying, J. P. Cortens, D. Ghosh, V. Spicer, W. Ens, K. G. Standing, R. C. Beavis, and J. A. Wilkins, *Use of peptide retention time prediction for protein identification by off-line reversed-phase HPLC-MALDI MS/MS.* Analytical Chemistry, 2006. 78 (17): p. 6265-6269.
89. O. V. Krokhin, *Sequence-specific retention calculator. Algorithm for peptide retention prediction in ion-pair RP-HPLC: Application to 300-and 100-angstrom pore size C18 sorbents.* Analytical Chemistry, 2006. 78 (22): p. 7785-7795.
90. E. W. Deutsch, H. Lam, and R. Aebersold, *PeptideAtlas: a resource for target selection for emerging targeted proteomics workflows.* Embo Reports, 2008. 9 (5): p. 429-434.
91. B. Marzolf, E. W. Deutsch, P. Moss, D. Campbell, M. H. Johnson, and T. Galitski, *SBEAMS-microarray: Database software supporting genomic expression analyses for systems biology.* Bmc Bioinformatics, 2006. 7.
92. V. A. Fusaro, D. R. Mani, J. P. Mesirov, and S. A. Carr, *Prediction of high-responding peptides for targeted protein assays by mass spectrometry.* Nature Biotechnology, 2009. 27 (2): p. 190-198.
93. P. Mallick, M. Schirle, S. S. Chen, M. R. Flory, H. Lee, D. Martin, B. Raught, R. Schmitt, T. Werner, B. Kuster, and R. Aebersold, *eComputational prediction of proteotypic peptides for quantitative proteomics.* Nature Biotechnology, 2007. 25 (1): p. 125-131.
94. P. Lu, C. Vogel, R. Wang, X. Yao, and E. M. Marcotte, *Absolute protein expression profiling estimates the relative contributions of transcriptional and translational regulation.* Nature Biotechnology, 2007. 25 (1): p. 117-124.
95. H. X. Tang, R. J. Arnold, P. Alves, Z. Y. Xun, D. E. Clemmer, M. V. Novotny, J. P. Reilly, and P. Radivojac, *A computational approach toward label-free protein quantification using predicted peptide detectability.* Bioinformatics, 2006. 22 (14): p. E481-E488.
96. B. J. M. Webb-Robertson, W. R. Cannon, C. S. Oehmen, A. R. Shah, V. Gurumoorthi, M. S. Lipton, and K. M. Waters, *A support vector machine model for the prediction of proteotypic peptides for accurate mass and time proteomics.* Bioinformatics, 2008. 24 (13): p. 1503-1509.
97. C. Harscoat-Schiavo, F. Raminosoa, E. Ronat-Heit, R. Vanderesse, and I. Marc, *Modeling the separation of small peptides by cation-exchange chromatography.* Journal of Separation Science, 2010. 33 (16): p. 2447-2457.
98. C. D. Kaplan and J. Kaplan, *Iron acquisition and transcriptional regulation.* Chem Rev, 2009. 109 (10): p. 4536-52.
99. V. K. Mootha, C. Handschin, D. Arlow, X. Xie, J. St Pierre, S. Sihag, W. Yang, D. Altshuler, P. Puigserver, N. Patterson, P. J. Willy, I. G. Schulman, R. A. Heyman, E. S. Lander, and B. M. Spiegelman, *Erralpha and Gabpa/b specify PGC-1alpha-dependent oxidative phosphorylation gene expression that is altered in diabetic muscle.* Proc Natl Acad Sci USA, 2004. 101 (17): p. 6570-5.
100. F. Mignone, G. Grillo, F. Licciulli, M. Iacono, S. Liuni, P. J. Kersey, J. Duarte, C. Saccone, and G. Pesole, *UTRdb and UTRsite: a collection of sequences and regulatory motifs of the untranslated regions of eukaryotic mRNAs.* Nucleic Acids Res, 2005. 33 (Database issue): p. D141-6.
101. S. E. Calvo, D. J. Pagliarini, and V. K. Mootha, *Upstream open reading frames cause widespread reduction of protein expression and are polymorphic among humans.* Proc Natl Acad Sci USA, 2009.
102. V. G. Tusher, R. Tibshirani, and G. Chu, *Significance analysis of microarrays applied to the ionizing radiation response.* Proc Natl Acad Sci USA, 2001. 98 (9): p. 5116-21.
103. J. D. Storey and R. Tibshirani, *Statistical significance for genomewide studies.* Proc Natl Acad Sci USA, 2003. 100 (16): p. 9440-5.

Example 2

Precursor Selection Using an Artificial Intelligence Algorithm Increases Proteomic Sample Comverage and Reproducibility As proteomics moves away from discovery based experiments towards hypothesis driven analyses, the measure of success is no longer the absolute number of proteins identified, but the identification of specific proteins of interest. This trend is exemplified in the surge of interest in selected reaction monitoring (SRM) based protein assays—a powerful tandem mass spectrometry method that can be used to monitor target peptides within a complex protein digest. These experiments typically entail careful optimization of fragmentation parameters, tight regulation of liquid chromatography (LC) conditions, and complex method scheduling. To date, in every mass spectrometer based protein assay, the spectrometer has been a passive agent. The user instructs the instrument on how to survey the precursor ion population, which precursors to interrogate, and how to interrogate those precursors. Essentially, the instruments require careful and detailed administration by the user, requiring laborious methods to produce sensitive, specific, and reproducible results.

As described herein, an artificial intelligence algorithm has been developed that enables the instrument to interpret information collected during the on-going analysis. Using this information the instrument is able to prioritize certain analyses over others. In this manner, the instrument is very efficient at collecting data that has a high-probability of identifying peptides and proteins of interest with minimal input from the user.

Mass Spectrometer Instrument Specifications.

Real-time precursor ion selection using an artificial intelligence algorithm relies on the ability to make a positive identification from the fragment ions of the dissociated precursor. With a mass accuracy of 10 to 20 ppm only about 5 fragment peak matches are required to uniquely identify a peptide. As the mass accuracy decreases the number of required peak matches increases. Above about 100 ppm accuracy, the number of false positive identifications can greatly increase, limiting the utility of this approach. The two fundamental requirements of a mass spectrometer for real-time identification are the ability to fragment the parent ion and the ability to analyze the fragment ion m/z values with an accuracy greater than 100 ppm. Other needed instrument functionalities will very as a function of the method chosen to follow the identification of the parent ion. A few examples of commercial instruments with fragmentation capabilities and mass accuracies better than 100 ppm are:

QTOF Instruments:
Waters QTOF Ultima, Waters QTOF Micro, MDS Sciex Qstar XL, and Bruker BioTOF.

ICR (FT-MS) Instruments:
Bruker Apex IV, Ion Spec 1, Thermo LTQ FT, Thermo Velos Orbitrap, and Thermo Exactive Orbitrap.

In an embodiment, the only input required by the algorithm is a list of peptides and proteins of interest. During operation the instrument focuses on the spectral features that correspond with the predicted m/z values of the precursors (proteins/peptides) of interest. As the analysis progresses, the algorithm collects information about the on-going elution profile by identifying peptides of interest as they elute. This information is used to (1) eliminate needless repeat acquisitions of the same feature, (2) determine what other peptides of interest may be co-eluting based on hydrophobicities, and (3) increase the depth of analysis by excluding the interrogation of peptides for a particular protein once it has been identified.

By moving control of the instrument from the user to the artificial intelligence algorithm, the instrument method becomes highly dynamic (i.e., the instrument method adapts to changing LC conditions on a time scale that would never be feasible if a human were operating the instrument). Because the algorithm considers numerous metrics when collecting data (retention time, m/z, instensity, etc.), the stochastic nature of typical data-dependent analyses is largely negated and run-to-run reproducibility increases dramatically.

In an embodiment, methods of identifying peptides and proteins in a mixture by prioritizing data acquisition based on the predicted m/z values of interest are provided. In an embodiment, methods of selecting and analyzing based on the hydrophobicities of the peptides are also provided.

Inclusion lists, where the user defines the proteins and peptides of interest, is an active area of research for commercial purposes. However, existing solutions are not able to confirm that the proteins and peptides are being correctly identified. More importantly, existing algorithms do not use the information acquired to dynamically control the interrogation being conducted by the apparatus.

The real-time target confirmation algorithm (rtTC) described herein works for two main reasons: (1) the number of possible comparison of each tandem mass spectrum is limited to the number of targets uploaded onto the instrument firmware, and (2) these computations can be performed expediently because matching is done at a high mass accuracy (e.g., 10 ppm or better for a match). From these it has been found that only 5 product ion matches are required in some instances to positively identify a target (~1% FDR).

The rtTC method enables many unique downstream data acquisition possibilities. A simple approach is to remove any identified targets from the inclusion. This allows for the addition of new targets or for a narrower focus on existing ones. One could also remove peptide targets corresponding to a protein when other targets from that same protein have been confirmed as present.

Another benefit is to use the information of which target is eluting to predict which targets may elute next. For example, the retention order of target peptides can be easily computed prior to analysis. This order is then loaded onto the instrument firmware, along with the target list. When a target is confirmed, in real time, the retention order list can be used to determine a subset of the targets that is most likely to be eluting at that time or in the near future. The MS acquisition can then be altered such that particular attention is paid to those targets that are predicted to be present. This list, of course, is continually updated as newer targets are picked off. Implementation of this particular method can be done in at least three different ways: (1) used to guide the instrument to examine specified m/z peaks in the full $MS^1$ scan (i.e., those predicted to be eluting); (2) to isolate narrower regions of the $MS^1$ m/z for increased sensitivity—i.e., m/z regions where the target is predicted to be; and (3) to not acquire $MS^1$ information and simply admit narrow m/z regions for direct MS/MS scanning that correspond with the predicted eluting target precursor m/z region.

Figure 15:
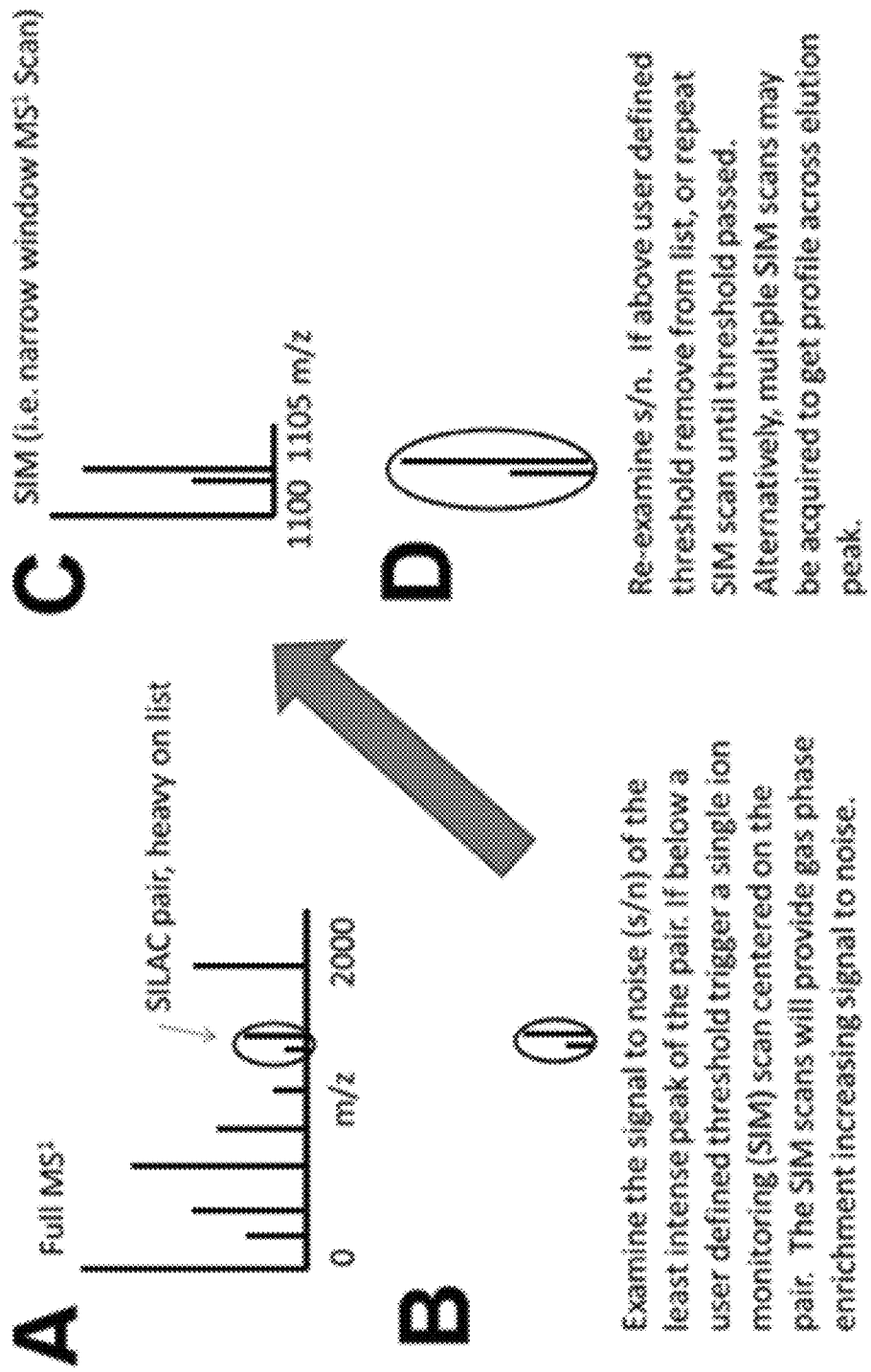

Once a target is confirmed, that information can be used to determine whether sufficient quantitative information is present in the MS/MS scan. If it is not, i.e., the MS1 precursor signal or isobaric tag reporter signal is below a user-defined quality threshold (such as a signal-to-noise ratio), additional scans can be trigged on the eluting target. These scans can be performed iteratively until the quality threshold has been met. An example of this acquisition method is shown in FIG. 15 which provides: a full MS1 scan having a SILAC pair in panel A in which the heavy ion is on a target acquisition list; the step of examining the signal-to-noise ratio of the least intense SILAC peak pair in panel B; narrowing the MS1 scan window to increase the signal-to-noise ratio of the SILAC pair peaks in panel C; and re-examining the signal-to-noise of the SILAC pair peaks in panel D. Because the heavy ion in panel A matches a predicted target on the acquisition list, the circled pair of peaks undergoes the additional SIM scan.

Other pertinent scanning can be triggered from the rtTC confirmation of a target. For instance, if a target contains a site of post-translational modification (PTM) and there are more than one possible amino acids within the sequence that could hold the modification. The instrument firmware can execute an algorithm to determine whether the MS/MS information is sufficient to localize the PTM to a specific site. If the site cannot be localized from the present information, additional procedures can be immediately executed. For instance, dissociation parameters can be altered and subsequent MS/MS scans collected. Other dissociation methods could likewise be triggered. Another possibility, perhaps concurrent, is to spectral average to achieve sufficient signal-to-noise such that site localization can be accomplished.

Preliminary data has shown that for large, complex, tryptic digests of yeast lysates the algorithm-based instrument control method is able to identify more than 90% of the peptides on a list that is ~5,000 entries long. In contrast, standard data-dependent analyses cover ~70% of the same list. The algorithm has also been tested on a list of difficult peptides (e.g., low intensity, poor fragmentation properties, etc.) that contains ~2,000 entries. The present method identifies ~2-fold more than the standard data-dependent method (~1,000 compared to ~500).

Although the description herein contains many specifics, these should not be construed as limiting the scope of the invention, but as merely providing illustrations of some of the embodiments of the invention.

Example 3

Instant Spectral Assignment for Advanced Decision Tree-Driven Mass Spectrometry

Note: numbers in brackets refer to the references listed at the end of this EXAMPLE 3.

This example provides a sequence identification algorithm (inSeq) that processes tandem mass spectra in real-time using the mass spectrometer's (MS) on board processors. inSeq relies on accurate mass tandem MS data for swift spectral matching with high accuracy. In an embodiment, the instant spectral processing technology takes ~16 ms to execute and provides information to enable autonomous, real-time decision making by the MS system. Using inSeq, and its advanced decision tree (DT) logic, the following is demonstrated: (1) real-time prediction of peptide elution windows en masse (~3 minute width, 3,000 targets), (2) significant improvement of quantitative precision and accuracy (~3× boost in detected protein differences), and (3) boosted rates of post-translation modification (PTM) site localization (90% agreement in real-time vs. offline localization rate and a ~25% gain in localized sites). The DT logic enabled by inSeq addresses longstanding problems with the conventional data-dependent acquisition paradigm and provides a direct route to streamlined and expedient targeted protein analysis.

Introduction.

The shotgun sequencing method, where proteins are digested into peptides, chromatographed, and detected by mass spectrometry (MS), has rapidly evolved over the past two decades (1, 2). In this strategy eluting peptide cations have their mass-to-charge (m/z) values measured in the $MS^1$ scan. Then, in order of abundance, precursor m/z values are selected for a series of sequential tandem MS events ($MS^2$). This succession is cycled for the duration of the analysis. The process, called data-dependent acquisition (DDA), is at the very core of shotgun analysis and has not changed for over fifteen years; MS hardware, however, has. Major improvements in MS sensitivity, scan rate, mass accuracy and resolution have been achieved. Orbitrap hybrid systems, for example, routinely achieve low ppm mass accuracy with MS/MS repetition rates of 5-10 Hz (3, 4). Constant operation of such systems generates hundreds of thousands of spectra in days. These $MS^2$ spectra are then mapped to sequence using database search algorithms (5-7).

The DDA sampling strategy offers an elegant simplicity and has proven highly useful, across most any MS platform, for discovery-driven proteomics. Of recent years, however, emphasis has shifted from protein identification to peptide-level quantification—often with certain targets in mind. In this context faults in the DDA approach have become increasingly evident. There are two primary limitations of the DDA approach: First, is poor run-to-run reproducibility and, second, is the inability to effectively target peptides of interest (8). Irreproducibility is caused by the highly stochastic nature of choosing which m/z peaks to sample. Dozens and even hundreds of peptides often co-elute so that low-level signals often get selected in one run and not the next. And selecting m/z peaks to sequence by abundance certainly does not offer the opportunity to inform the system of pre-selected targets.

Several DDA add-ons and alternatives have been examined. Sampling depth, for example, can be increased by preventing selection of an m/z value identified in a prior technical replicate (PANDA) (9). Irreproducibility can be somewhat countered by informing the DDA algorithm of the precursor m/z values of desired targets (inclusion list)—if observed this can ensure their selection for $MS^2$. Frequently, however, low abundance peptides may not have precursor signals above noise so that $MS^2$ scan, which is requisite for identification, is never triggered. This conundrum is avoided altogether in the data-independent acquisition approach (DIA) (10). Here no attention is paid to precursor abundance, or even presence, instead consecutive m/z isolation windows are dissociated and mass analyzed. A main drawback of DIA is that it requires significantly more instrument analysis time as $MS^2$ scans from every m/z window must be collected (11). As such, DDA analysis remains the preeminent method for MS data acquisition.

Besides improvements in MS analyzer performance, numerous alternative dissociation methods and scan types have recently advanced. These include collision, electron and/or photon-based fragmentation (i.e., trapHCD, HCD, ETD, IRMPD, etc.), specialized quantification scans (i.e., selected ion monitoring (SIM) or precursor purification methods (QuantMode, QM)), or simply analysis using varied precursor ion targets, m/z accuracy, etc. (12-17). Each of these techniques show applicability and superlative performance for some subset of peptide precursors. The result is a dizzying alphabet soup of techniques, scan types, and parameter space that is not easily integrated into the current data acquisition paradigm. Recently, a decision tree (DT) algorithm was introduced that used precursor m, z, and m/z to automatically determine, in-real time, whether to employ CAD or ETD during $MS^2$ (18). The approach significantly improved sequencing success rates and was an important first step in a movement toward development of informed acquisition. Unfortunately only a limited amount of knowledge can be gleaned from the very basic information of m, z, and abundance.

Here, the next advance in DT acquisition technology is described—instant sequence confirmation (inSeq). The inSeq algorithm processes $MS^2$ spectra at the moment of collection using the MS system's on board processing power. With sequence in hand the MS acquisition system can process this knowledge to make autonomous, real-time decisions about what type of scan to trigger next. Here, with the inSeq instant identification algorithm, the simple DT method is extended by adding several new decision nodes. These nodes enable novel automated functionalities including: real-time elution prediction, advanced quantification, PTM localization, large-scale targeted proteomics, and increased proteome coverage, among others. This technology provides a direct pathway to transform the current, i.e., DDA, passive data collection paradigm. Specifically, knowing the identity of a peptide that is presently eluting into the MS system permits an ensemble of advanced, automated decision-making logic.

Results.

Instant Sequence Confirmation (inSeq).

An approach to develop an advanced DT acquisition schema, which can seamlessly incorporate the myriad of specialized procedures and scans available on modern day MS systems is to expedite the spectral analysis process—i.e., from off-line to real-time. Knowledge gained from these instant analyses enables automated decision making logic to extract the most information possible from an MS analysis. There are two pathways to incorporate real-time spectral analysis within an MS system. The first approach exports spectra for processing with an external computing system followed by import of the search outcome (19). A second, more elegant strategy, is to perform all computation within the MS on-board computing system (20). The former approach circumvents complications in accessing instrument firmware and allows for the use of more sophisticated processing power; however, a serious constraint is the time required for import/export of the information (i.e., ~40 ms). For this reason technologies and computational algorithms have been pursued that integrate real-time spectral analysis into the MS system's on-board processors and firmware. This method has been named "instant sequence confirmation" or "inSeq".

Figure 19:
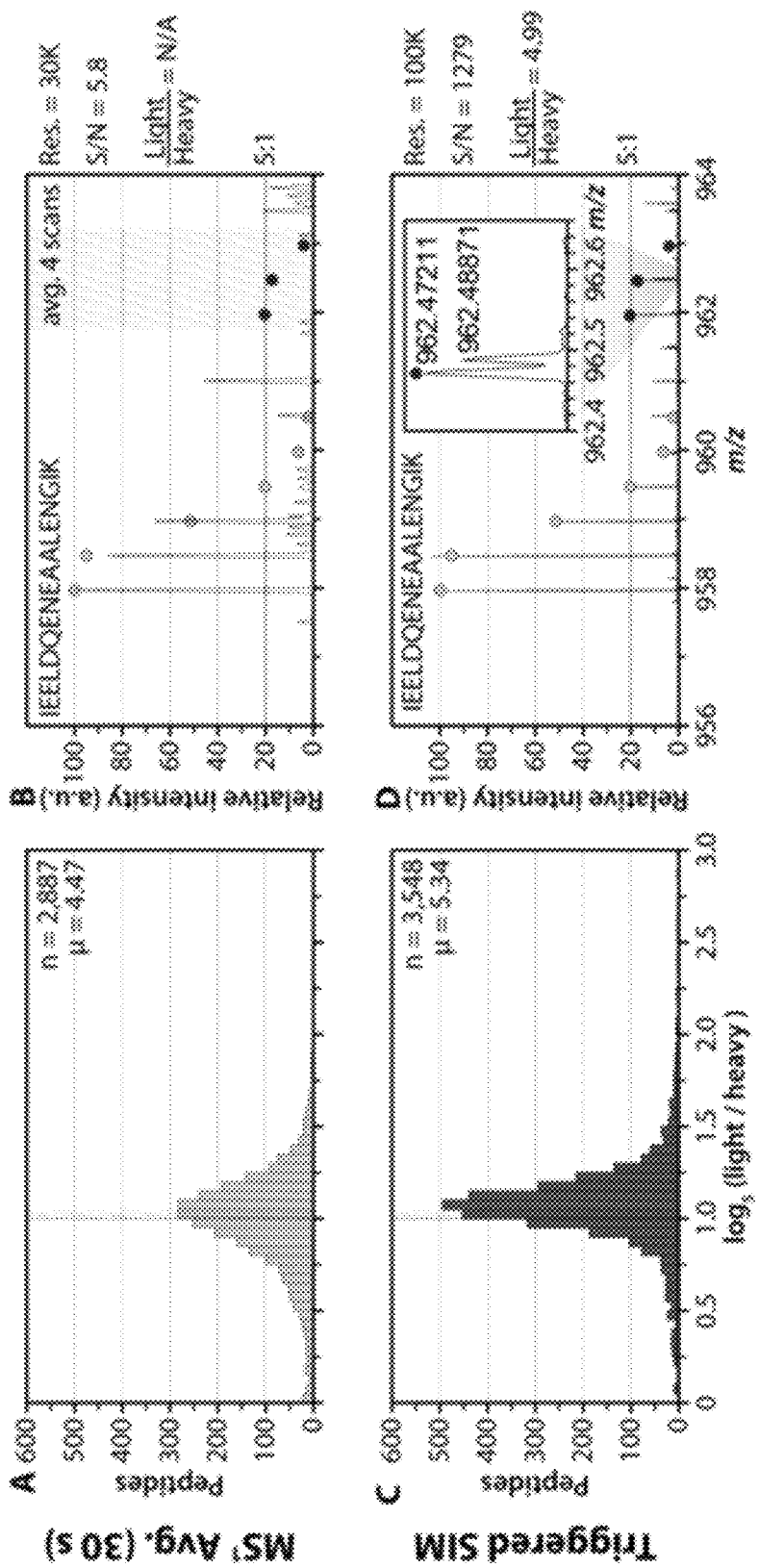
FIG. 19 provides experimental results demonstrating that inSeq can improve quantitative outcomes for SILAC. Following an inSeq confirmation of a peptide having the sequence, IEELDQENEAALENGIK (SEQ ID NO:1), a narrow (8 Th), high-resolution (R=100,000) SIM scan was automatically triggered and increased the S/N from 5.8 to 1,279 (Panels A and B). This SIM scan enabled detection of both partners and yielded the correct ratio of 5:1 (light:heavy). Besides increased dynamic range, the theoretical isotope distribution (shown in open circles) closely matches in the SIM scan (panel B), while the signal for the heavy partner is not even detectable in the $MS^1$ (panel A). Over our entire data set, the inSeq triggered SIM scans improve the mean ratio from 4.47 to 5.34, but, more impressively, produced ~20% more quantifiable measurements (3,548 vs. 2,887).

To establish robustness across platforms inSeq was implemented on two distinct MS systems (operating with different code bases)—a dual cell quadrupole linear ion trap-orbitrap hybrid (LTQ-Velos Orbitrap) and a quadrupole mass filter-orbitrap hybrid (Q-Exactive). In both cases the instrument firmware was modified and extended to quickly (~<20 ms in the case of the more modern Q-Exactive system) and accurately (<2% false discovery rate (FDR)) map MS/MS spectra to sequence. The embedded peptide database-matching algorithm processes MS/MS scans immediately (FIG. 14A-B) by comparing product ions present in the MS/MS scan to those from peptide candidates pre-loaded onto the instrument's firmware. Note the candidate sequences are first filtered so that only sequences whose mass is within 30 ppm of the sampled precursor neutral mass are considered (FIG. 14C). For each candidate sequence the number of +1 product ions (+2 ions are included for precursors >+2) that matched the spectrum at a mass tolerance <10 ppm is recorded (FIG. 14C). The algorithm employs memorization optimization techniques for calculating product ions information, i.e., calculating the information only once and storing the results in a fast reference table. Next, it uses straightforward scoring metrics, providing sufficient evidence for the confirmation of a putative sequence without burdening the system with non-essential calculations. On both MS platforms the real-time confirmation algorithm was expediently executed and required no hardware modification, taking an average of 16 ms to perform (Q-Exactive, FIG. 19). Note similar processing times were achieved on the older Velos-Orbitrap system; however, an additional ~100 ms overhead was included as the existing firmware required complete collection of the Orbitrap transient signal prior to inSeq analysis.

To characterize the inSeq algorithm, a nHPLC-MS/MS experiment was performed on tryptic peptides derived from human embryonic stem cells. Prior to analysis, a database consisting of all theoretical tryptic peptides (up to three missed cleavages, 6-50 in length) contained within the human proteome was uploaded to the instrument's (Q-Excative) on-board computer. A data-dependent top 10 method was employed and analysis proceeded as usual, except following each MS/MS scan the inSeq algorithm was executed and the results logged. This manifest of instant identifications was then compared to those made post-acquisition via traditional database searching at a 1% FDR (reverse-decoy method). It was assumed that the conventional post-acquisition approach to represent the true answer and compared the number of correct instant spectral identifications as a function of matched product ions (FIG. 14D). From these data it was concluded that the detection of >6 product ions at high mass accuracy (<10 ppm) by the inSeq algorithm produces the correct sequence identification >98% of the time.

inSeq represents a simple, expedient approach to correlate sequence to spectrum and is positioned to become an essential technology in transforming the current passive data collection paradigm. Specifically, learning the identity of a peptide that is presently eluting into the MS system permits an ensemble of advanced, automated decision-making logic. These concepts build upon the previous development of the data-dependent decision tree (DT) method. There an on-board algorithm was embedded to make unsupervised, real-time decisions of which fragmentation method to engage, based on precursor charge (z) and m/z. Here, with the inSeq instant identification algorithm, the simple DT method is extended by adding several new decision nodes. These nodes enable automated functionalities including: real-time elution prediction, advanced quantification, PTM localization, large-scale targeted proteomics, and increased proteome coverage, among others (FIG. 14F).

Predicting Peptide Elution.

Liquid chromatography is the conventional approach to fractionate highly complex peptide mixtures prior to measurement by MS. The highest MS sensitivity is achieved when one tunes the MS system to detect a given target (i.e., execute MS/MS) regardless of its presence in the preceding $MS^1$ event (i.e., selected reaction monitoring). SRM measurements deliver both sensitivity and reproducibility at the cost of bandwidth. Specifically, if one does not know the elution time of a target, the duration of the nHPLC-MS/MS analysis must be dedicated to conditions for that specific entity. If elution times are known, then multiple SRM scan events can be programmed allowing for detection of multiple targets; however, chromatographic conditions must remain identical or the scheduled SRM elution windows will no longer align. Still, the bandwidth of that approach is low, ~100 peptide targets per nHPLC-MS/MS analysis, and compiling such an experiment is highly laborious (21).

It was surmised that inSeq could inform the MS system, without human intervention, of which peptide targets are most likely to subsequently elute. Such capability could enable robust, large-scale targeting (>500 per analysis) in an automated manner. This approach relies upon relative peptide elution order and, consequently, bypasses the use of absolute retention times, which shift depending on chromatographic conditions and are not directly portable from multiple disparate experiments. Peptide elution order can be obtained in two ways: First, discovery experiments can be employed to determine retention order by normalizing the measured retention time for each detected peptide sequence. Second, the relative hydrophobicity for any sequence can be theoretically determined using existing software (e.g., SSRCalc) (22-24). From prior experience it is believed that experimentally determined retention order offers better precision; still, it requires prior knowledge which may not be available. However retention order is determined, the real-time confirmation algorithm maintains a rolling average of the calculated elution order (CEO—a number describing the relative elution order of a target peptide) so that target peptides having nearby CEOs are specifically pursued (FIG. 15B). FIG. 15 presents an overview of this approach. This example, 60.39 minutes into the chromatograph, highlights the last five inSeq identified peptides and their average CEO (26.926 a.u.). The on-board algorithm then computes an asymmetric CEO window (5 a.u., 24.926-29.926) that presents a short list of desired targets having CEOs within that range (FIG. 15C). With this information the MS system can trigger specialized $MS^2$ scans specific to this refined target subset. Note that as targets are identified, the CEO window is dynamically adjusted so targets come into and out of the range precisely when they are eluting.

To test this technology, a data-dependent top-10 nHPLC-MS/MS experiment was performed in which tryptic peptides from a human ES cell sample were separated over a 60 minute gradient. Following data collection the resulting MS/MS spectra were mapped to sequence using database searching (1% FDR). The unique peptide identifications (4,237) were sorted by observed retention time—this ordering then served as the CEO. 3,000 of these peptides were randomly selected as "targets" and subsequently loaded onto the instrument firmware (Velos-Orbitrap), along with their respective CEO, as a database for inSeq. The sample was then re-analyzed with inSeq activated, but with a doubled gradient length (120 min). FIG. 15D displays the CEO window as calculated in real-time by the MS system (inSeq) plotted beside the actual elution time of identified peptides. Greater than 95% of the peptides (2,889) fell within the rolling CEO window and were identified by both inSeq and post-acquisition searching. Further, the rolling CEO window width averaged ~4 minutes for each of these 3,000 targets. At present capability, window widths similar to those used in absolute scheduling type experiments (~3-6 minutes) can be achieved on a scale that is 30× larger (e.g., 3,000 targets vs. 100) with minimal effort (21, 25). Further, this approach easily adapts to different chromatographic conditions with no negative effects (FIG. 15D). The key to the high portability and simplicity of this algorithm is the use of inSeq for continual, real-time realignment.

Improvement of Quantitative Accuracy.

The method of stable isotope labeling has greatly propelled large-scale, quantitative analysis (26-31). While generally robust, these techniques can yield spotty data for certain peptide and protein groups—mainly those present at low abundances. For SILAC, low signal-to-noise (S/N) precursor peaks in the $MS^1$ scan often result in either omission of that particular feature or quantitative imprecision, if included (32). For isobaric tagging, low intensity reporter ion signals ($MS^2$) induces similar shortcomings (33). It was surmised that inSeq could be employed to counter these limitations.

First, an inSeq module was developed to improve the quality of isobaric label-based measurements. The module analyzes $MS^2$ spectra, using inSeq, and, when a peptide of interest is detected, the quality of quantitative data is assessed. Should the reporter ion signal fall below a specified threshold, inSeq triggers follow-up scans to generate increased signal at the very instant the target peptide is eluting. In one implementation, inSeq was instructed to automatically trigger three quantitative scans, using the recently developed QuantMode (QM) method, to generate superior quality quantitative data on targets of high value (17). Triggering three additional MS/MS scans commits ~1 second of instrument time to a single precursor. Constitutive operation in this mode would severely hamper duty cycle; however, triggering the scan sequence on only a few hundred pre-selected, high value targets commits a modest time commitment and can deliver exceptional quantitative information on the user-selected peptide targets. The trio of QM scans are then summed offline.

Figure 16:
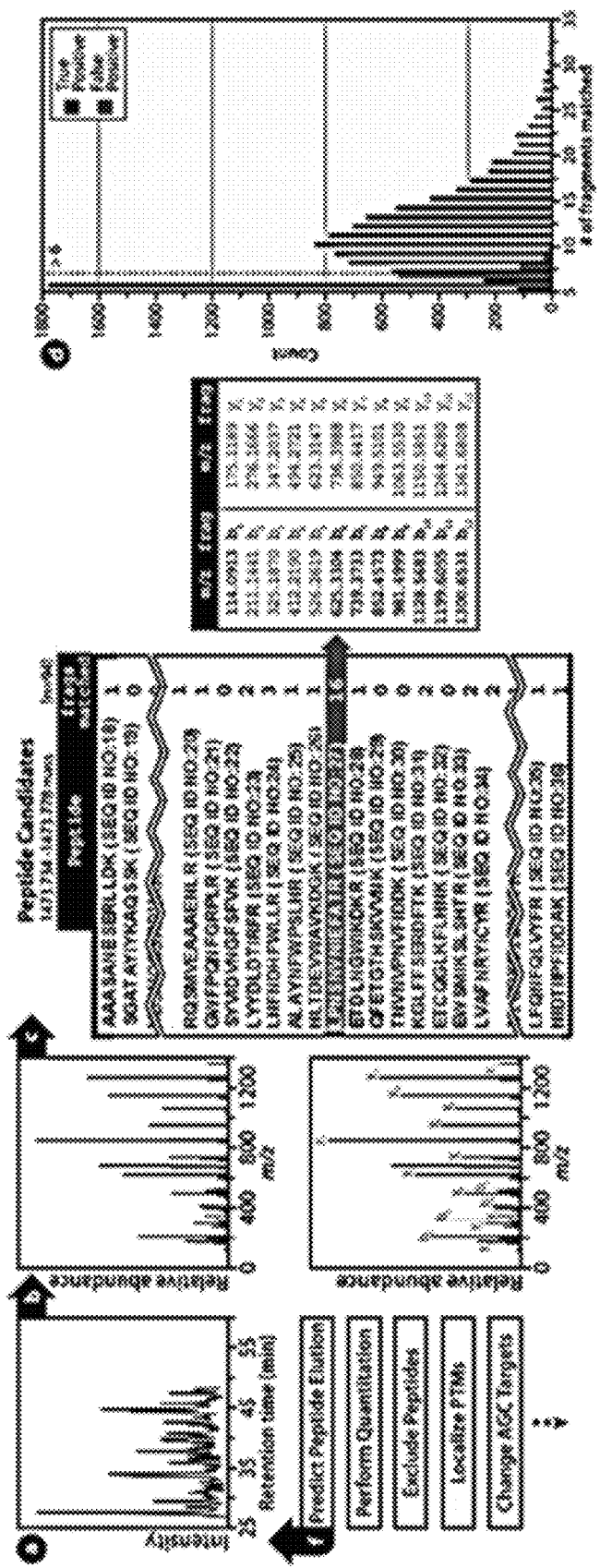
FIG. 16 provides an illustration of a progression of the inSeq logic. (Panel A) A nHPLC-MS/MS chromatogram at 48.35 minutes along with an $MS^2$ scan (panel B) that was acquired at that time following dissociation of a doubly protonated feature of m/z 737.86. Upon collection of the $MS^2$ scan, inSeq groups all peptide candidates (in silico, n=94) whose theoretical mass are within 30 ppm of the experimentally determined precursor neutral mass 1473.756 (panel C). Then inSeq performs in silico fragmentation to produce a theoretical product ion series for each of the 94 candidates and proceeds to compare each to the experimental spectrum (<10 ppm mass accuracy). (panel D) Plot of inSeq identifications compared to conventional post-acquisition searching. inSeq agrees (True Positive)>98% of the time when >6 fragment ions are matched.

To assess this decision node, a sample comprising three biological replicates of human embryonic stem cells (ESCs) was analyzed pre- and two days-post bone morphogenetic protein 4 (BMP4) treatment (i.e., TMT 6-plex, three pre-treatment and three post BMP4 treatment cell populations). BMP4, a growth factor that induces context-dependent differentiation in pluripotent stem cells, is widely used to study differentiation to biologically relevant cell lineages such as mesoderm and endoderm. FIG. 16A demonstrates the benefit of summing isobaric tag intensities from one, two, or three consecutive quantitation scans for an inSeq identified target peptide having the sequence FCADHPFLFFIR (SEQ ID NO:3) from the protein SERPINB8. Here the ratio of change between control and treatment cell lines measured in one QM scan is large (5.86) but not significant (P=0.067, Student's t-test with Storey correction) (34). Note significance testing was accomplished by assessing variation within the three biological replicates of both treatment and control cell lines. The measured ratio remains relatively unchanged (5.22 and 5.43) as reporter tag signal from additional quantitation scans are added; however, the corresponding P-values decrease to 0.014 and 0.012 when two or three quantitation scans are summed. By plotting the $\log_2$ ratio of quantified proteins from the three biological replicates against the average intensity of isobaric labels (FIG. 16B) it was demonstrated that this improved significance results from boosted reporter signal-to-noise. Ideally this $\log_2$ ratio would be zero, indicating perfect biological replication; however, when only one quantitation scan is employed this ratio severely deviates from zero with decreasing tag intensity. To improve overall data quality and to omit potentially erroneous measurements arbitrary reporter signal cutoffs (dashed vertical line in FIG. 16B) can be employed. These cutoffs eliminate many low-abundance peptides which often represent proteins of interest. Summation of additional quantitation scans increases the average reporter tag intensity, raising nearly all of the protein measurements above the intensity cutoff value (74, 9, and 4 proteins omitted using one, two, and three quantification scans, respectively). This quantification decision node also increased the number of proteins within 25% of perfect biological replication (horizontal dashed line).

To determine if the method could improve the number of statistically significant differences between the cell populations, the $\log_2$ ratio of treated vs. control (i.e., 2 days/0 days) was calculated for each of the 596 quantified proteins (P<0.05, Student's t-test with Storey correction, FIG. 16C). To display both fold change and significance the P-value for each protein difference was plotted against its corresponding ratio. Only 28 proteins display significant change when one QM scan is used. By simply adding the reporter tag signal from one additional scan the number of significantly changing proteins increases nearly threefold, from 28 to 83. When all three QM scans are analyzed together, the number of significantly changing proteins increases slightly, to 91.

Many stable isotope incorporation techniques measure heavy and light peptide pairs in $MS^1$ (e.g., SILAC). This approach, of course, requires the detection of both partners; note low abundance peptides are often identified with low, or no, precursor signal in the MS$^1$. It is believed that addition of another inSeq decision node could circumvent this problem. Human embryonic stem cells (ESCs) were cultured in light and heavy media (i.e., Lysine[$^{13}C_6$-$^{15}N_2$]). Protein extract from these cultures was mixed 5:1 (light:heavy), before digestion overnight with LysC. The SILAC node was developed to select precursors from an MS$^1$ scan only if the monoisotopic mass was within 30 ppm of any target on a list which contained 4,000 heavy and light peptides from a previous discovery run. Targets were selected only if the SILAC ratio deviated from the expected ratio of 5 by 25%, i.e., the subset containing the most error. Following MS/MS, the resulting spectra were analyzed using inSeq. When a target of interest was identified, inSeq instructed the system to immediately record a SIM scan surrounding the light/heavy pair with a small, charge-dependent isolation window (~8-10 Th). The narrow isolation range provides gas phase enrichment of low abundance target precursors and enables accurate quantification of many peptides whose data would otherwise be discarded.

Figure 17:
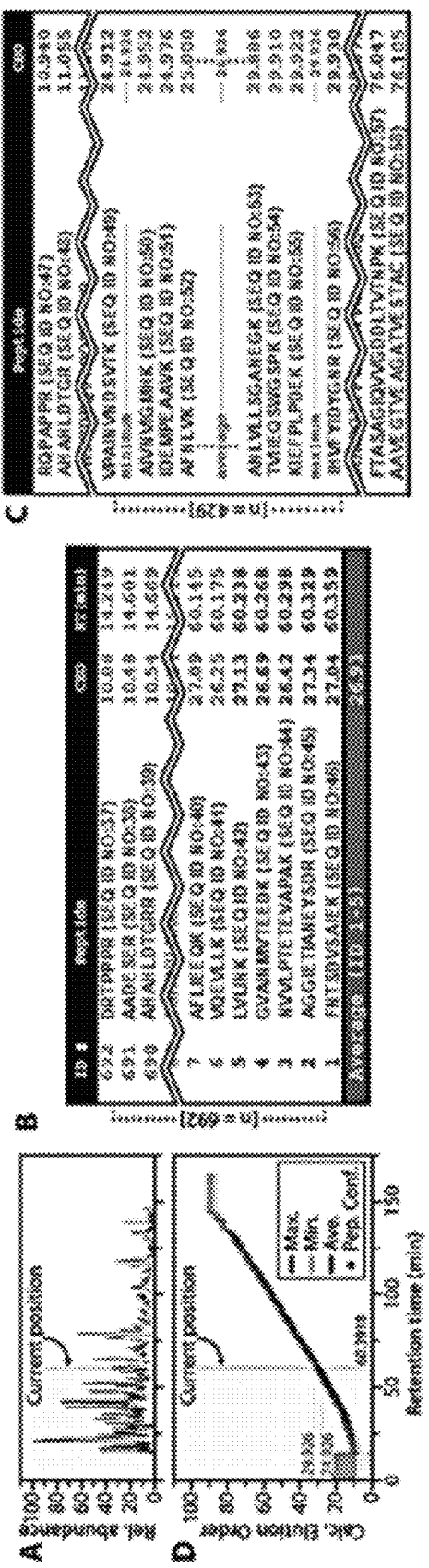
FIG. 17 provides experimental results demonstrating embodiments using elution order prediction using inSeq. (Panel A) Experimental chromatogram, 60.39 minutes into a 120 minute gradient, obtained while inSeq was recording instant identifications. (Panel B) The inSeq calculated elution order (CEO) obtained by averaging the CEOs of the preceding 5 instantly identified peptides. (Panel C) The asymmetric window (5 a.u.) surrounding the instant CEO average ($\mu$=26.926) and their corresponding sequences. inSeq can then refine a target list to only include those having CEOs within the predicted window. (Panel D) This analysis is repeated following each new peptide confirmation to constantly realign the CEO window based on current chromatographic conditions.

The average ratio of the light and heavy peptides subtly, but significantly, shifted from 4.47 under normal analysis to 5.34 for the inSeq triggered SIM scans (Student's t-test, p-value<$6 \times 10^{-20}$). More importantly, the number of useable measurements, i.e., when both partners of the pair are observed, increased by ~20% (2,887 under normal analysis to 3,548 with inSeq). The overall distribution of these data is plotted in FIG. 17A. Panel B of FIG. 17 displays an example of the inSeq-triggered SIM scan and the increase in S/N and accuracy it affords. Here the MS/MS scan of the light partner was mapped, in real-time, to the sequence IEELDQENEAALENGIK (SEQ ID NO:1), a pre-defined target. This event triggered a high resolution SIM scan (8 Th window), which determined the ratio of 4.99:1 (correct ratio 5:1). Here gas phase enrichment was essential to quantify the relative abundance, as the isotopic envelope of the heavy partner was not observed, even with extensive spectral averaging of successive MS$^1$ scans (~30 s, FIG. 17B). Whether for MS$^1$ or MS$^2$ centric methods, it is believed that inSeq technology will significantly improve the quality of quantitative data with only a minimal impact on duty cycle.

Post-Translational Modification Site Localization.

The presence, or lack, of post-translational modifications (PTMs) on proteins plays a major role in cellular function and signaling. Unambiguous localization of PTMs to residue demands observation of product ions resulting from cleavage of the residues adjacent to the site of modification, i.e., site-determining fragments (SDFs). Phosphorylation analysis has become increasingly widespread; however, in a typical analysis only about half of the identified phosphorylation sites can be mapped with single amino acid resolution. These ambiguous spectra stymie systems-level data analysis and prevent use of thousands of identified phosphopeptides. It was reasoned that inSeq could be leveraged to boost PTM localization rates by dynamically modifying MS$^2$ acquisition conditions when necessary. As such, an online PTM localization decision node was developed to determine, within milliseconds, whether a MS/MS spectrum contains SDFs to unambiguously localize the PTM. Should SDFs be lacking, inSeq instantly orchestrates further interrogation.

The PTM localization node is engaged when inSeq confirms the detection of a PTM-bearing peptide. After the sequence is confirmed, inSeq assesses the confidence with which the PTM(s) can be localized to a particular amino acid residue. This procedure is accomplished by computing an online probability score similar to post-acquisition PTM localization software—i.e., AScore (35). Using the MS system's embedded processors, inSeq compares all possible peptide isoforms against the MS/MS spectrum. For each SDF the number of matches at <10 ppm tolerance is counted and an AScore is calculated (inSeq uses similar math). If the AScore of the best fitting isoform is above 13 (p<0.05) the PTM is declared localized and the inSeq routine ends. When the AScore is lower than 13, however, inSeq triggers further characterization of the eluting precursor until either the site has been deemed localized or all decision nodes have been exhausted. Additional characterization can include many procedures such as acquisition of MS/MS spectra using different fragmentation methods (e.g., CAD, HCD, ETD, PD, etc.), varied fragmentation conditions (e.g., collision energy, reaction time, laser fluence, etc.), increased spectral averaging, MS$^n$, pseudo MS$^n$, modified dynamic exclusion, and altered AGC target values, among others (36).

Figure 18:
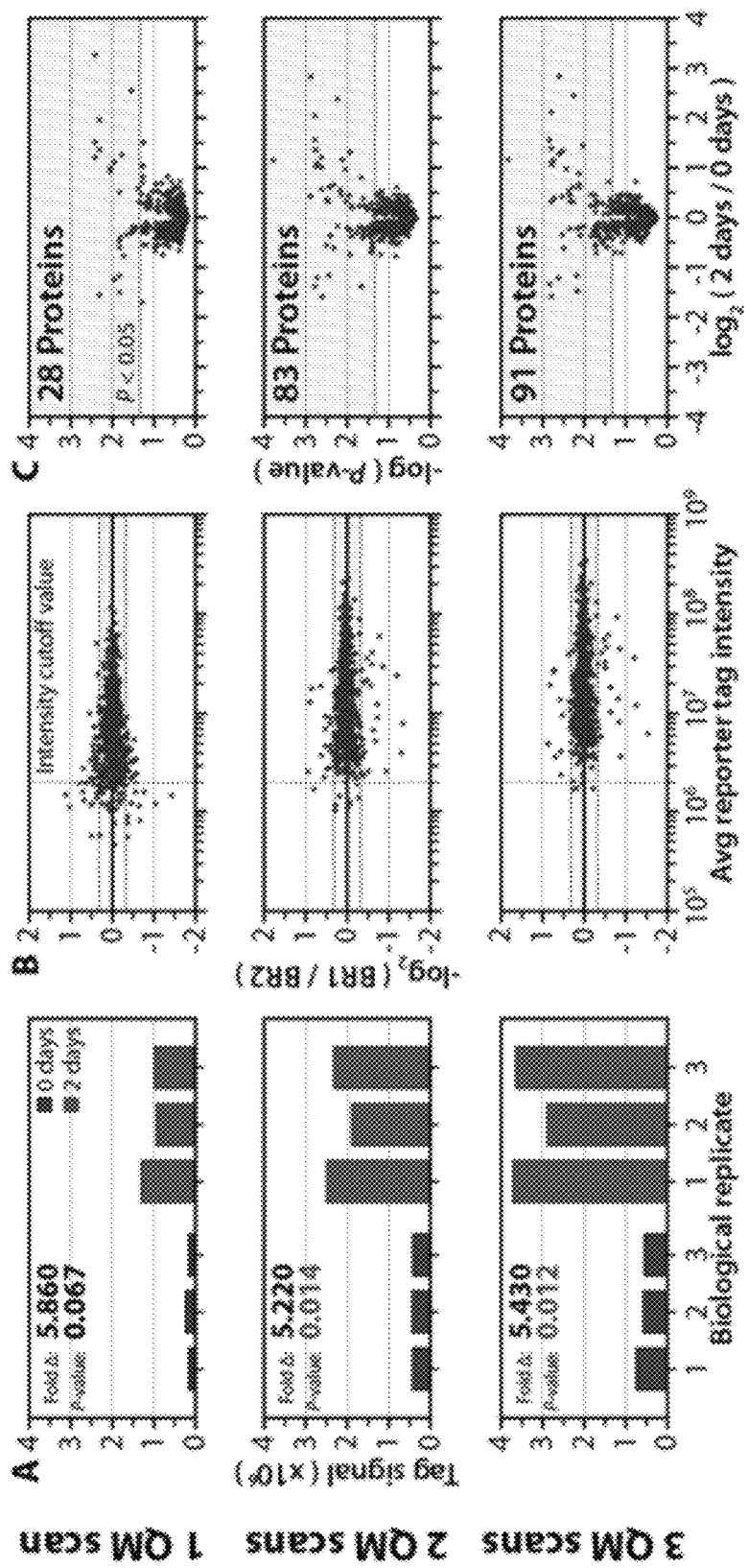
FIG. 18 provides experimental results demonstrating that inSeq improves quantitative outcomes for isobaric tagging. An inSeq decision node was written to so that a real-time identification of a target sequence prompted automatic acquisition of three consecutive QuantMode (QM) scans. (Panel A) Summing the reporter ion tag intensity from one, two, or three QM scans greatly improves the statistical significance of the measurement. (Panel B) Summation of QM technical replicates reduces the variation in biological replicate measurement by increasing reporter ion S/N. (Panel C) inSeq-triggered QM scans increase the number of significantly changing proteins from 28 to 91.
Figure 20:
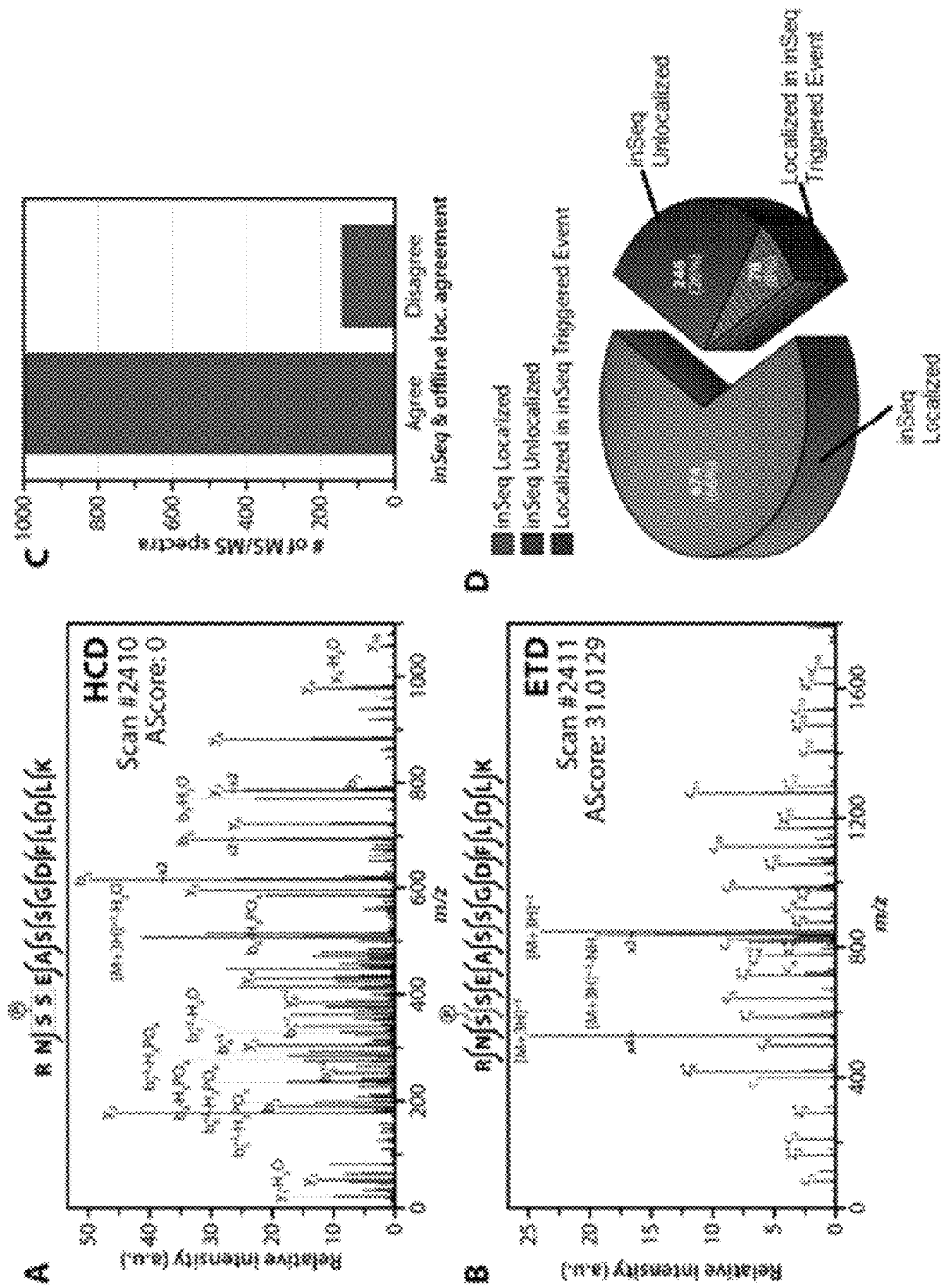
FIG. 20 provides experimental results demonstrating that inSeq can improve PTM localization rates. Following $MS^2$ (HCD) of the singly-phosphorylated precursor RNsSEASS-GDFLDLK (SEQ ID NO:2), inSeq could not find sufficient information to confidently localize the modification to either Ser 3 or 4 (panel A, AScore=0). inSeq immediately triggered an ETD $MS^2$ scan event on the same precursor (panel B). This spectrum was assigned an AScore of 31.0129 (phosphorylation on Ser3) and was considered confidently localized—note the SDFs $c_3$ and $z_{.12}$ ions. (panel C) Globally, the inSeq localization calculation agreed with offline analysis using the actual AScore algorithm. (Panel D) Using a simple dissociation method DT, inSeq produced a confidently localized phosphorylation site for 78 of 324 unlocalizable sites.
Figure 21:
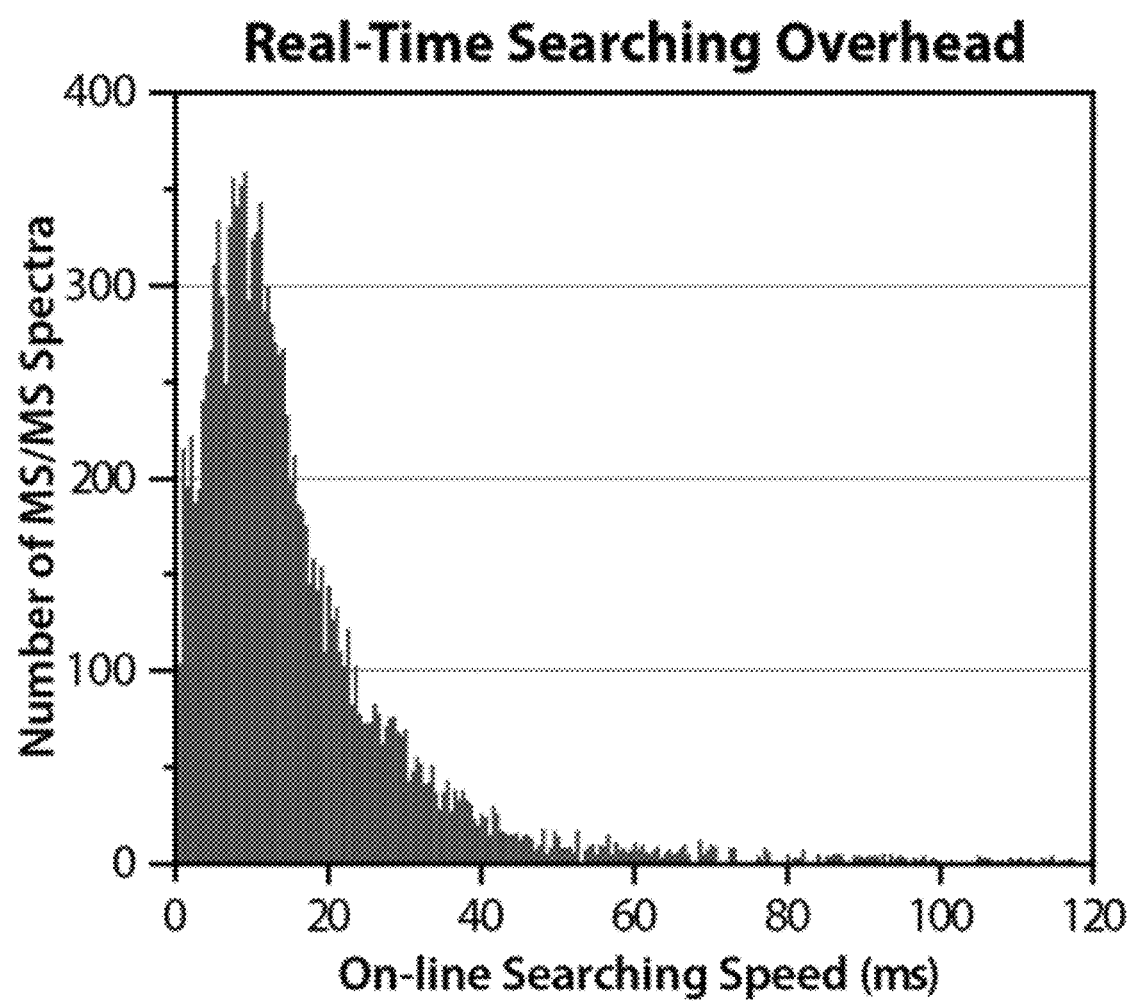
FIG. 21 provides a distribution of inSeq instant analysis times (Q-Exactive). The complete yeast proteome (6,717 proteins) was digested in silico, trypsin specificity up to 3 missed cleavages) and the resulting peptides sorted to only retain those between 6-50 residues in length for a database of 1,174,780 unique sequences. The overhead accrued by inSeq is small ($\mu$=16 ms/spectrum) compared to the overall acquisition rate (~100-250 ms/spectrum), with over 95% of the $MS^2$ events taking less than 45 ms to search.
Figure 22:
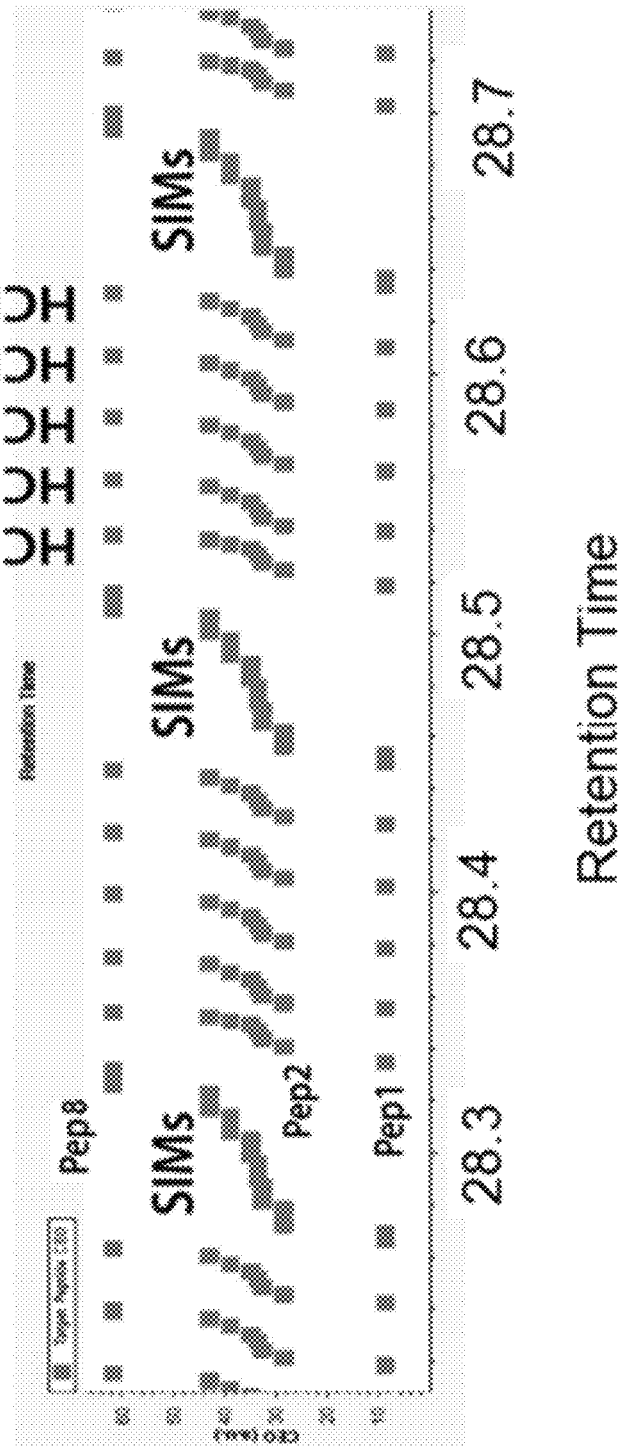
FIG. 22 provides experimental results testing inSeq (Q-Exactive) detection capabilities. Twenty five AQUA™ peptides (Sigma-Aldrich) were spiked into yeast whole cell lysate at 2 fmol (on column). Eight of these peptides were targeted by performing 5 HCD (PRM) scans followed by 1 SIM for the whole run (90 min).

To obtain proof-of-concept results, a simple inSeq node was written that triggered an ETD MS/MS scan of phosphopeptides that were not localized following HCD MS$^2$. An example of how this logic can function is presented in FIG. 18 where a target phosphopeptide was detected during a shotgun experiment. The sequence, RNSSEASSGDFLDLK (SEQ ID NO:2), was confirmed to contain a phosphoryl group; however, the inSeq algorithm could not confidently localize the PTM to any of the four Ser residues (AScore=0). inSeq determined the most probable sites as either Ser 3 or Ser 4. Next, inSeq triggered an ETD MS$^2$ scan of the same precursor (FIG. 18B). The resulting spectrum was then analyzed for the presence of the SDFs, $c_3/z_{12}$. Both of these fragments were present and the phosphorylation site was localized to Ser 3 with an AScore of 31.0129 (p<0.00079). Post-acquisition analysis confirmed the results of the online inSeq approach—both spectra (HCD and ETD) were confidently identified and their calculated AScores were 0 and 45.58, respectively. When compared on a global scale, 993 of the 1,134 inSeq-identified phosphopeptides had localization judgments that matched post-acquisition A-Score analysis (FIG. 18). These data demonstrate that the localization node is highly effective at instantaneously determining whether a PTM site can be localized. Still, this information must be acted upon to achieve markedly improved localization outcomes. Unfortunately, only marginal gains were achieved in this basic implementation as most precursors were doubly charged and, therefore, not effectively sequenced by ETD. Next, the inSeq decision node was modified to incorporate a dissociation method DT. Here a follow-up ETD or combination ion trap CAD/HCD scan was triggered depending upon precursor charge (z) and m/z. With the slightly evolved algorithm the inSeq method detected 998 phosphopeptides in a single shotgun experiment. It determined that 324 of these identifications lacked the information to localize the PTM site and, in those cases, triggered the new dissociation decision node. 78 of these unlocalizable sites were confidently mapped with this technique—salvaging nearly 25% of the unlocalized sites (FIG. 20D). These encouraging results demonstrate that inSeq addresses the issues of PTM localization in a highly automated fashion. The disclosed methods are also applicable to a variety of other useful device parameters and MS conditions, such as collision energy, reaction time, laser fluence, spectral averaging, MS$^n$, adjustment of AGC target values, targeting of a different charge state, etc., to explore in the continued advancement of this PTM localization decision node.

Discussion

Here is described an instant sequencing algorithm (inSeq) that operates using the pre-existing processors of the mass spectrometer. inSeq relies on accurate mass MS$^2$ data for expedient spectral matching with high accuracy. Rapid real-time sequencing affords several novel data acquisition opportunities. To orchestrate these opportunities, an advanced decision tree logic was constructed that extends the earlier use of the method to intelligently select dissociation type. The approach can circumvent longstanding problems with the conventional DDA paradigm. Three such examples are provided herein. First, it is provided that knowledge of which peptide sequences are eluting can facilitate the prediction of soon to elute targets. This method shows strong promise to revolutionize the way in which targeted proteomics is conducted. Second, quantitative decision nodes were used that fired when inSeq detected a peptide sequence of interest. With either SILAC or isobaric tagging, significant gains in quantitative outcomes were documented. Third, inSeq was endowed with an instant PTM site-localization algorithm to determine whether or not to initiate more rigorous follow-up at the very instant the peptide of interest was eluting. It is shown that the inSeq site localizer is highly effective (90% agreement with post-acquisition analysis) and that triggering a simple dissociation method DT can improve site localization by—25%. Further development will doubtless deliver additional gains.

Targeted proteomics is an area of increasing importance. Following discovery analysis it is natural to cull the list of several thousand detected proteins to several hundred key players. In an ideal world these key proteins are then monitored in dozens or even hundreds of samples with high sensitivity and reproducibility, without rigorous method development. And this, of course, must be done expediently as hundreds of samples are involved. It is envision that advanced DT analysis with inSeq could offer such a platform. Using the retention time prediction algorithm introduced here one can foresee the inSeq algorithm quickly and precisely monitoring hundreds of peptides without the extensive labor and pre-planning required by the selected reaction monitoring (SRM) technique, current state-of-the-art (37). Other possibilities include automated pathway analysis where user-defined proteins, within a collection of pathways, are simply uploaded to the MS system. Then, inSeq automatically determines the best peptides to track, their retention times, and constructs the method. Two key advantages over current SRM technology make this operation possible. First, knowledge of specific fragmentation transitions are not necessary as all products are monitored with high mass accuracy. Second, precise elution time scheduling is not necessary as inSeq can use CEO, experimental or theoretical, to dynamically adjust the predicted elution of targets. In this fashion the most tedious components of the SRM workflow can be avoided.

Materials and Methods

Cell Culture, Cell Lysis, Digestion, Isobaric Labeling, and Phosphopeptide Enrichment.

Cells were lysed by sonication and protein extracted. For SILAC experiments protein from the two cell cultures was mixed 5:1 light:heavy before digestion. For all experiments, protein was digested either by LysC or LysC/Trypsin before desalting. For isobaric labeled experiments peptides were labeled, mixed, and desalted before nHPLC-MS/MS analysis. For phosphopeptide experiments, phosphopeptides were enriched via IMAC. Further details are provided in SI Text.

inSeq Configuration, nHPLC, MS, Database Searching, Phosphosite Localization, and Peptide and Protein Quantification.

For all experiments, inSeq target lists and method parameters were loaded into the instruments firmware. All experiments were performed on LTQ Orbitrap Velos and Q-Exactive mass spectrometers (Thermo Fisher Scientific). All MS/MS spectra were searched using OMSSA (Open Mass Spectrometry Search Algorithm). Peptide FDR, Protein FDR, and peptide and protein quantification using isobaric labels was performed using COMPASS. Phosphosite localization and SILAC quantitation was performed using in-house software. Additional details are provided in SI Text.

Cell Culture.

Human embryonic stem cells (line H1) were maintained in feeder independent media as previously described (Chen et al). For SILAC experiments, DMEM/F12 lacking lysine and arginine (Mediatech Inc.) was supplemented with light arginine (Sigma-Alrich) and either heavy labeled lysine (Cambridge Isotopes Laboratories) or light lysine (Sigma-Aldrich). Cells were cultured on Matrigel (BD Biosciences) and split 1:8 at approximately 80% confluency using 0.1 mM EDTA. To harvest cells, TripLE Express (Invitrogen) was applied for five minutes at 37 degrees C. Following cell detachment, an equivalent volume of ice-cold DPBS (Invitrogen) was added before centrifugation. Cell pellets were subsequently washed twice in ice-cold DPBS and stored at −80 degrees C. BMP4-treated cells were grown and harvested as described above, except that 5 ng/mL BMP4 (R&D Systems) was added into the media and cells were split using TrypLE (Invitrogen). For BMP4 experiments, single cells were plated at the density of $4 \times 10^4/cm^2$, for 1, 1.5, 2, 3 and 4 days of treatment. Approximately $10^8$ cells were collected for each analysis. (For lysis, labeling, enrichment, and n-LC methods see supporting information)

Cell Lysis.

For all analysis, human embryonic stem cells were lysed in ice-cold 8M urea, 40 mM NaCl, 50 mM tris (pH 8), 2 mM $MgCl_2$, 50 mM NaF, 50 mM b-glycero phosphate, 1 mM sodium orthovanadate, 10 mM sodium pyrophosphate, 1× mini EDTA-free protease inhibitor (Roche Diagnostics), and 1× phosSTOP phosphatase inhibitor (Roche Diagnostics). To solubilize protein and ensure complete lysis, samples were sonicated three times for 15 seconds with 30 second pauses. Total protein was then quantified using a BCA protein assay kit (Thermo Scientific Pierce).

Isobaric Label Sample Preparation.

For analysis, 250 ug of protein from each sample was reduced by adding DTT to a final concentration of 5 mM, and alkylated with 15 mM iodoacetamide before final capping with 5 mM DTT. Digestion was carried out by adding LysC (Wako Chemicals) at a 1:100 enzyme-to-protein ratio and incubating at 37 degrees C. for 2 hours. At this time, the lysate was diluted with 25 mM tris (pH 8) to a final urea concentration of 1.5 M and further digested for 12 hours at 37 degrees C. with trypsin (Promega) at a 1:100 enzyme to protein ratio. Peptides were then acidified with TFA to quench the reaction and de-salted using C-18 solid phase extraction (SPE) columns (Waters). TMT labeling was carried out per manufacturer's directions (Thermo Scientific Pierce). Samples were mixed in a 1:1:1:1:1:1 ratio before analysis.

SILAC Sample Preparation.

Protein from the light and heavy embryonic stem cell cultures was mixed in a 5:1 ratio (light:heavy) by pooling 2.5 mg of light protein and 0.5 mg of heavy protein. The sample was reduced by adding DTT to a final concentration of 5 mM, and alkylated with 15 mM iodoacetamide before final capping with 5 mM DTT. Digestion was carried out by adding LysC (Wako Chemicals) at a 1:100 enzyme-to-protein ratio and incubating at 37 degrees C. overnight. Peptides were then acidified with TFA to quench the reaction and de-salted using C-18 solid phase extraction (SPE) columns (Waters).

Phosphopeptide Sample Preparation.

From an embryonic stem cell culture, 1 mg of protein was reduced by adding DTT to a final concentration of 5 mM, and alkylated with 15 mM iodoacetamide before final capping with 5 mM DTT. Digestion was carried out by adding LysC (Wako Chemicals) at a 1:100 enzyme-to-protein ratio and incubating at 37 degrees C. for 2 hours. At this time, the lysate was diluted with 25 mM tris (pH 8) to a final urea concentration of 1.5 M and further digested for 12 hours at 37 degrees C. with trypsin (Promega) at a 1:100 enzyme to protein ratio. Peptides were then acidified with TFA to quench the reaction and de-salted using C-18 solid phase extraction (SPE) columns (Waters).

Phosphopeptides were enriched via immobilized metal affinity chromatography (IMAC) using magnetic beads (Qiagen). Following equilibration with water, the beads were treated with 40 mM EDTA (pH 8.0) for 30 minutes with shaking, and washed 3× with water again. The beads were then incubated with 100 mM FeCl3 for 30 minutes with shaking and finally were washed 3 times with 80% acetonitrile/0.1% TFA. Samples were likewise resuspended in 80% acetonitrile/0.15% TFA and incubated with beads for 45 minutes with shaking. The resultant mixture was washed 3 times with 1 mL 80% acetonitrile/0.1% TFA, and eluted using 1:1 acetonitrile:0.7% NH4OH in water. Eluted phosphopeptides were acidified immediately with 4% formic acid and lyophilized to ~5 µL.

Nano-High Performance Liquid Chromatography.

For all samples online reverse-phase chromatography was performed using a NanoAcquity HPLC system (Waters). Peptides were loaded onto a pre-column (75 µm ID, packed with 7 cm C18 particles, Alltech) for 10 min at a flow rate of 1 µm/min. Samples were then eluted over an analytical column (50 µm ID, packed with 15 cm C18 particles, Alltech) using either a 60 or 120 min linear gradient from 2% to 35% acetonitrile with 0.2% formic acid and a flow rate of 300 nL/min.

Target List Construction and inSeq Setup.

For all experiments, the monoisotopic mass, charge state, and previously determined retention time of target peptides was included for use by the inSeq algorithm. In addition, peptides modified on methionines or tyrosines were omitted from all target lists. For peptide elution and isobaric label quantitation inSeq experiments, a target list of 4,000 peptides was constructed from a previous nHPLC-MS/MS experiment employing a 90 min nHPLC gradient. For SILAC inSeq experiments, peptides identified at 1% FDR in a discovery nHPLC-MS/MS experiment were analyzed to determine the light:heavy partner ratio. A target list of 2,000 peptide pairs (4,000 total peptides) whose ratio deviated from the expected value of 5 by at least 25% was constructed. This subset of peptides included many measurements in which the signal to noise was low, or a partner was missing. For phosphorylation inSeq experiments, phosphopeptides identified at 1% FDR in a discovery nHPLC-MS/MS experiment were analyzed by the Phosphinator to assign phosphosite locations. A target list comprising 2,174 phosphopeptides was constructed and used for both ETD only and decision tree (DT) inSeq methods.

Target lists were loaded into the instrument's firmware for instant access during acquisition. Peptide lists were stored in an internal database and sorted based on their precursor mass for fast look ups using a binary search algorithm. A parameter file was preloaded into the firmware prior to each experiment to specific scan sequences and instrument parameters needed for the intended experiment.

Mass Spectrometry.

All experiments were performed on Thermo LTQ Orbitrap Velos and Q-Exactive mass spectrometers. The LTQ Orbitrap Velos used firmware version 2.6.0.1065 SP3 with additional ion trap control language (ITCL) modifications to enable inSeq operation. MS1 scans were performed in the Orbitrap at 30,000 resolution at a max injection time of 500 ms and a target value of 1e6. MS2 scans were also performed in the Orbitrap at a resolution of 7,500 and with HCD normalize collision energy (NCE) of 27%, for a max fill time of 500 ms. The Q-Exactive was operated using version 2.0 Build 142800 with a modified python code base for inSeq data acquisition control. Q-Exactive MS1 scans were collected at 70,000 resolution for a max injection time of 120 ms or if the 1e6 AGC target value was reached. MS2 events were measured at 17,500 resolution at a target value of 1e5, 120 ms max injection time and 26% NCE. Instrument methods for both the LTQ Orbitrap Velos and Q-Exactive were overridden during acquisition by the instrument's firmware to provide for dynamic inSeq operation.

Database Searching and FDR Estimation.

MS/MS data was analyzed using the Coon OMSSA Proteomics Software Suite (COMPASS) (38). The Open Mass Spectrometry Search Algorithm (OMSSA; version 2.1.8) was used to search spectra against the International Protein Index (IPI) human database version 3.85 (39). Precursor mass tolerance was set to ±4.5 Da and monoisotopic mass tolerance was set to ±0.015 Da for fragments ions. For all experiments, carbamidomethylation of cysteines was included as a fixed modification, while oxidation of methionines was set as a variable modification. For TMT experiments, TMT on the N-terminus and TMT on lysines were included as fixed modifications and TMT on tryosines was added as a variable modification. For SILAC experiments heavy lysine was added as a variable modification. Results were filtered to a 1% FDR at both the peptide and protein level. For phosphopeptides, the Phosphinator software was used to localize phosphorylation sites (30).

Protein and Peptide Quantification.

TMT quantification was performed using TagQuant within COMPASS. This program extracts reporter ion intensities multiplies them by injection times to determine counts. Purity correction was performed as previously described. Tag intensities were normalized to ensure that the total signal from each channel was equal. For evaluation of multiple Quant-Mode (QM) scans, data was analyzed at the peptide level by only quantifying the first, the sum of first and second, or the sum of the first, second, and third QM scans using TagQuant. Peptides were then combined into protein groups (Protein-Herder) and quantified at the protein level (ProteinTagQuant) within COMPASS. Experimental ratios and p-values (Student's t-test assuming equal variance) were determined using Microsoft Excel. To correct for multiple hypothesis testing, Storey correction was applied using the freely available program QVALUE (34).

SILAC quantification was performed with in-house software that retrieved the peak intensities of both SILAC partners from either a single inSeq-triggered SIM scan (monoisotopic peak) or performed an extract ion chromatogram (30 sec window) of identified precursor. A ratio of partner abundance was only calculated if both SILAC partners had an intensity at least twice that of the noise.

PRM: Testing Detection Capabilities.

Figure 23:
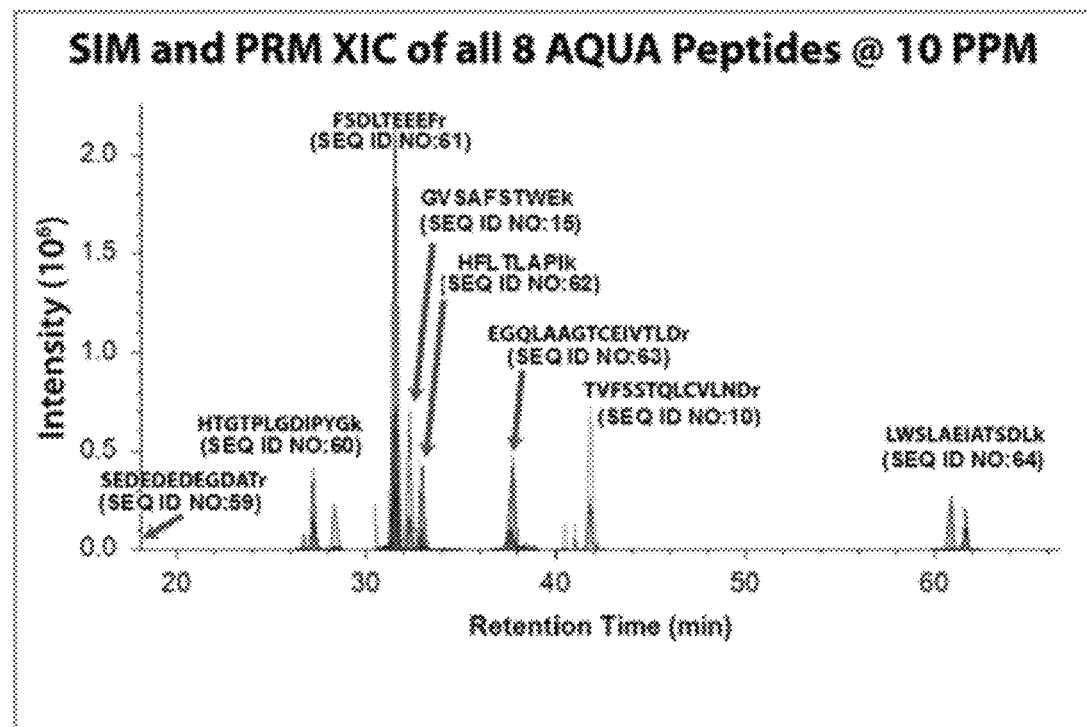
FIG. 23 provides SIM and PRM extracted ion chromatograms (XIC) for the 8 AQUA™ peptides targeted in FIG. 22.

Having demonstrated that multiple peptides can be targeted simultaneously using inSeq-triggered PRM while maintaining normal DDA-type acquisition, it was examined how the inSeq method compared to normal DDA acquisition. inSeq PRM was performed on the Q-Exactive device to test the detection capabilities of the system. Twenty five human heavy (AQUA™ peptides, Sigma-Aldrich) were spiked into a 1 µg/µl yeast background matrix. Two fmol of the peptides were loaded on a column and targeted using inSeq PRM. Eight of these peptides were targeted by performing 5 HCD scans (1 Hz/peptide, 2.0 TH) followed by 1 SIM for the whole run (90 min, 0.2 Hz/peptide, 3.0 TH iso) (FIG. 23). The resulting SIM and PRM extracted ion chromatograms (XIC) at 10 ppm for these peptides are shown in FIG. 23. inSeq was able to detect each of the 8 peptides at 2 fmol (peptide-spectrum match by OMSSA at 1% FDR), while only 1 to 3 of these peptides were detected at 2 fmol using Top 10 data-dependent acquisition (DDA).

inSEQ: Instant Sequence Confirmation

Figure 26:
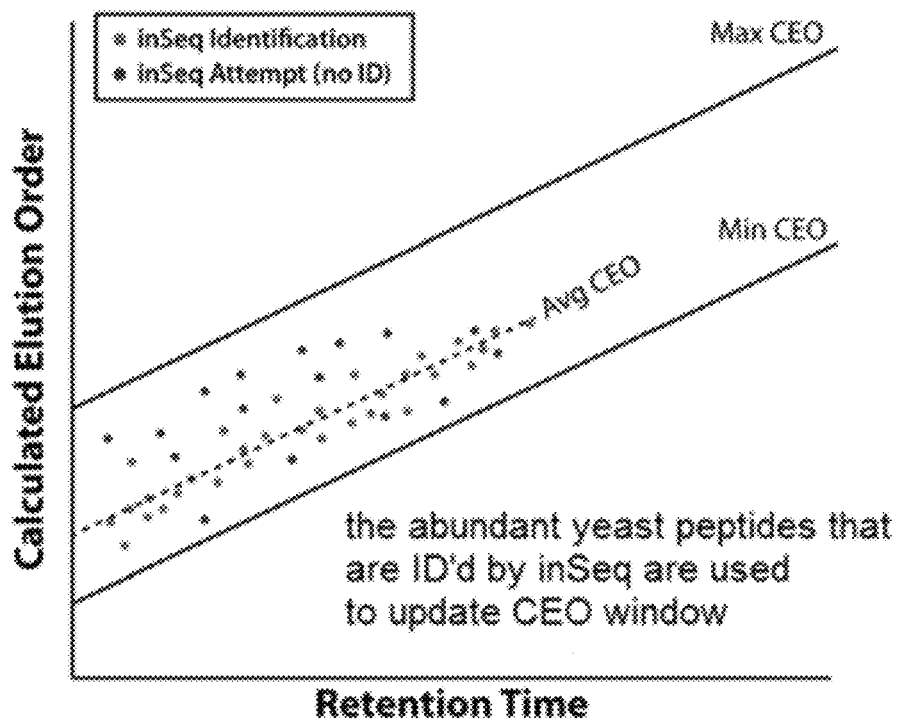
Figure 27:
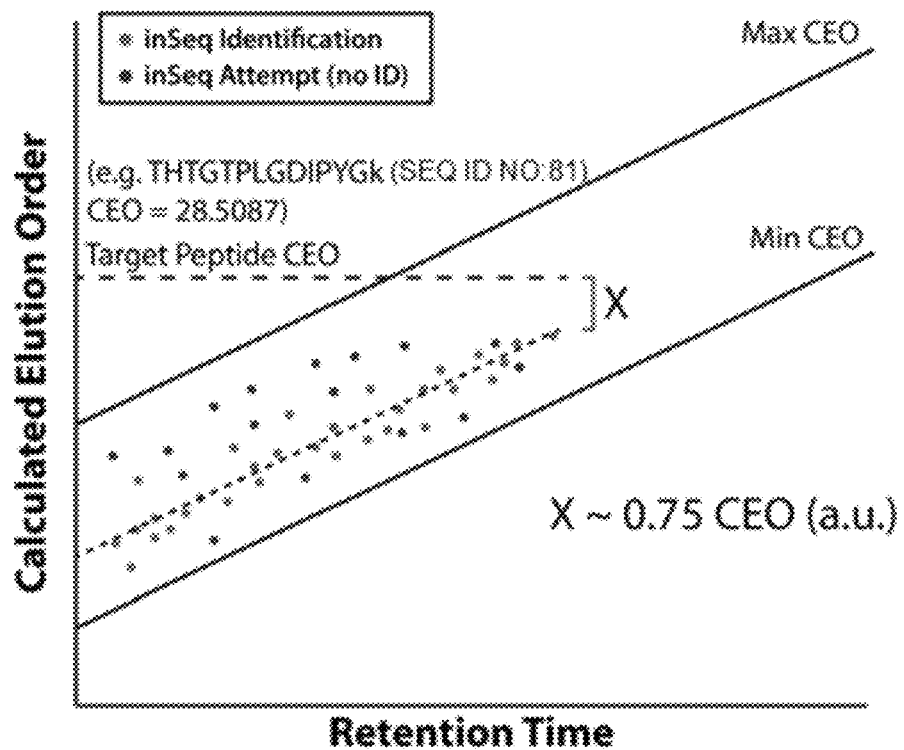
Figure 28:
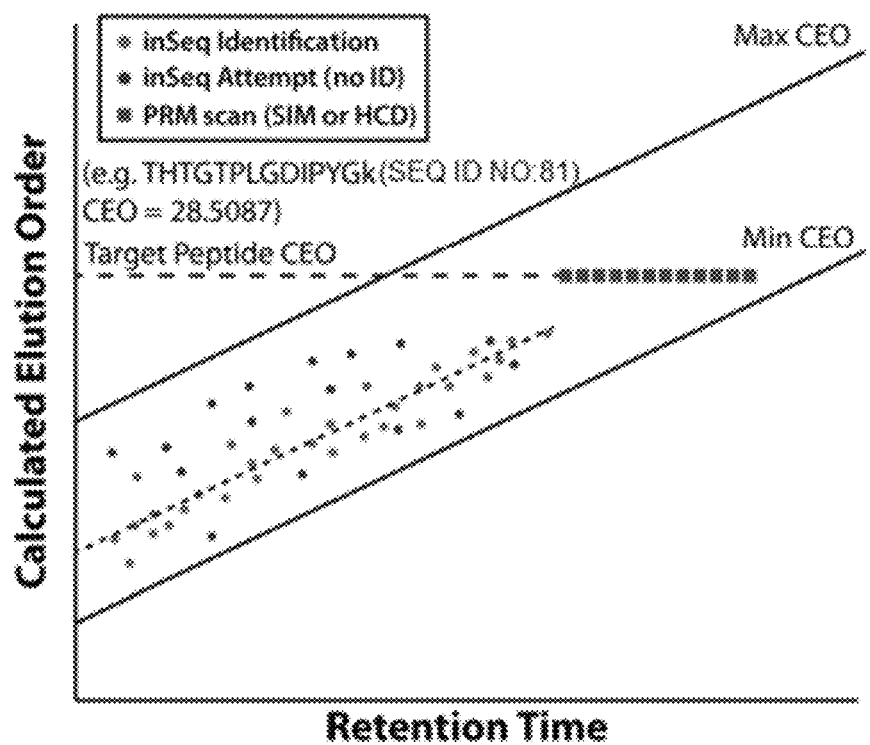
Figure 29:
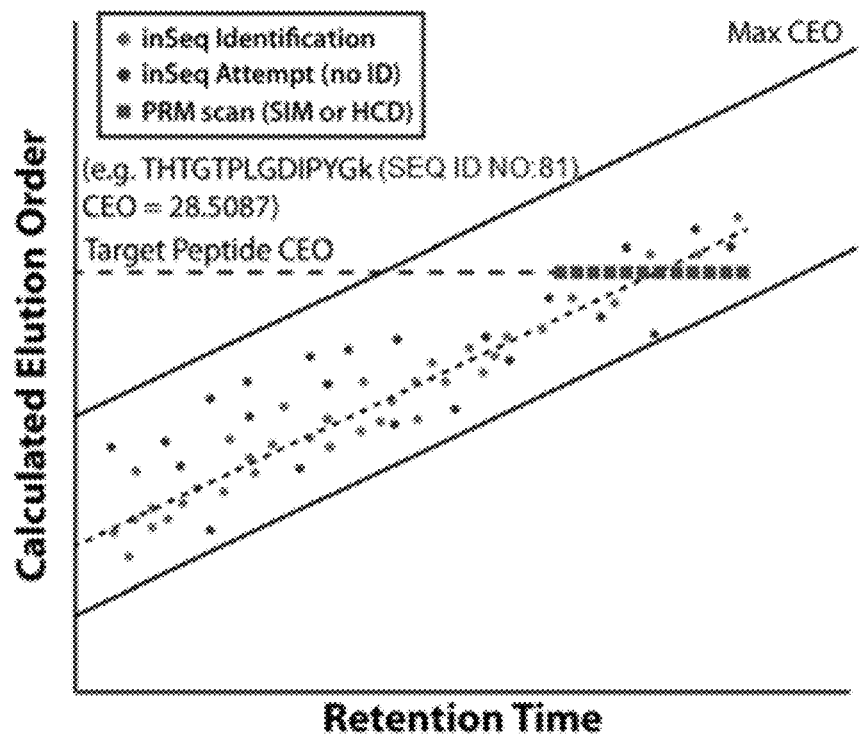
Figure 30:
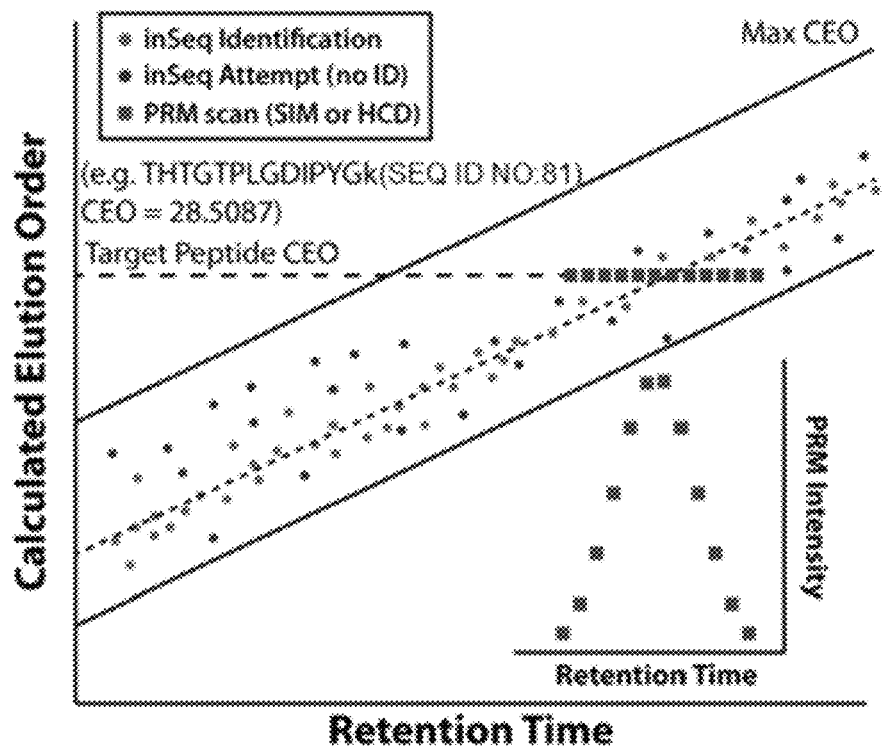

FIGS. 25-30 provide schematic steps 1-6 for an instant sequence confirmation using inSeq. In step 1, a list of peptide targets is constructed from previous DDA experiments and sorted according to elution order (CEO). As illustrated in the partial list depicted in FIG. 25, the full list can contain one or more target peptides, such as the eight AQUA™ peptides from the previous experiments. In step 2, DDA is performed using an inclusion list from the list of peptides loaded onto the instrument (FIG. 26). The peptides that are ID'd by inSeq can be used to update the CEO window. In step 3, the PRM cycle for a target peptide is initiated when the average CEO approaches the CEO for that target (FIG. 27). In step 4, PRM scans are started at a regular frequency (e.g. 0.5 Hz) for a set time period (FIG. 28). In step 5, DDA scan are resumed to update the CEO window once the device is free to begin additional scans (FIG. 29). In step 6, the process is repeated and DDA is performed with the inclusion list until the next target approaches the CEO window for that target wherein a new PRM cycle is started (FIG. 30). Ideally, sampling is started early enough so as to capture the whole peptide elution.

inSeq Implementation and Data Structures

Figure 31:
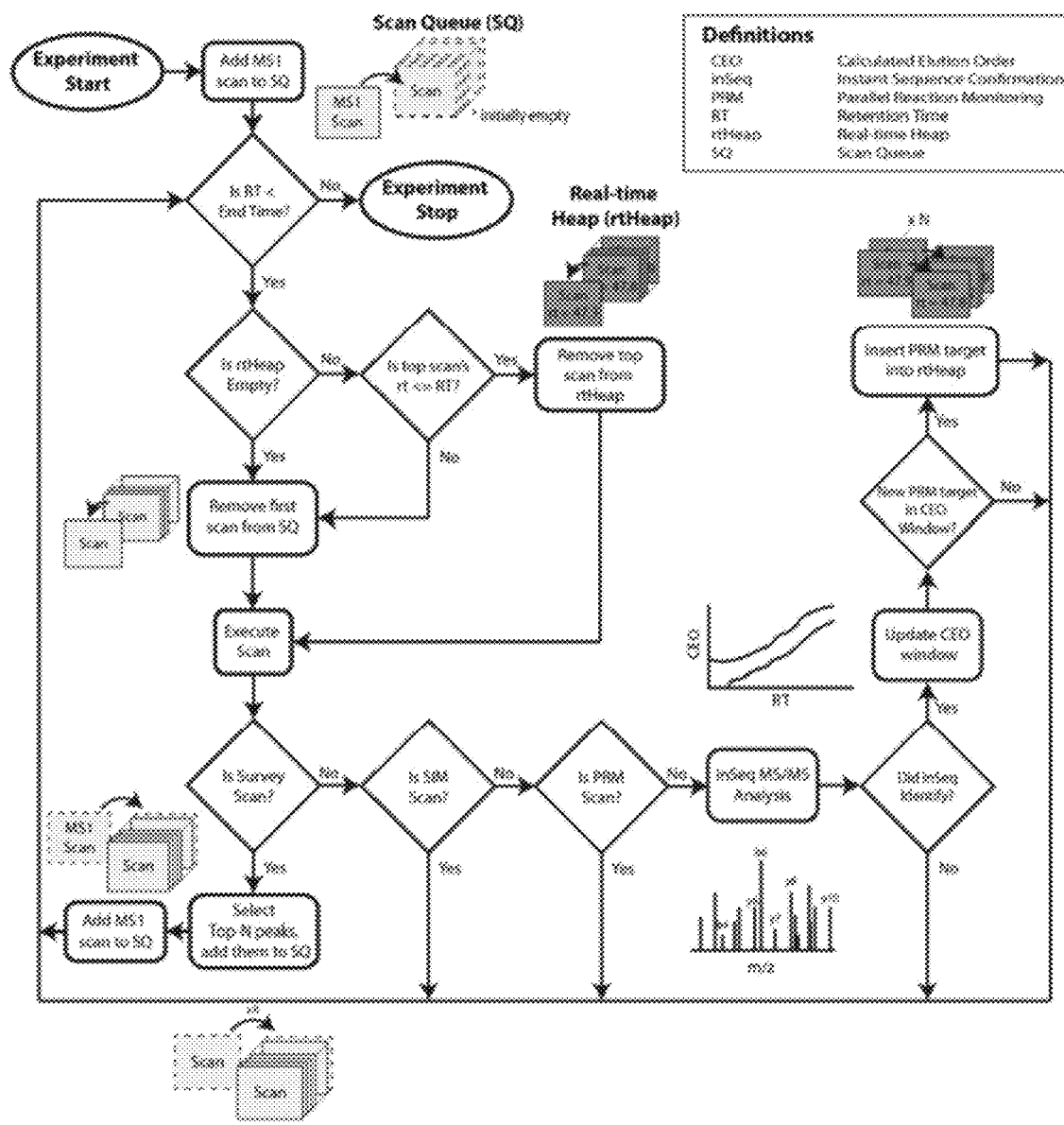
FIG. 31 provides a flow diagram showing implementation of an inSeq process. This process contains two data structures to store upcoming scans for the mass spectrometer to perform: 1) a Scan Queue (SQ) data structure, and 2) a Real-Time Heap (rtHeap) data structure, with scan in the rtHeap taking precedence over any scans in the SQ.

FIG. 31 provides a detailed flow diagram showing the operational steps of a real time inSeq process. The process depicted in this figure contains two data structures to store upcoming scans for the mass spectrometer to perform: 1) a Scan Queue (SQ) data structure, and 2) a Real-Time Heap (rtHeap) data structure.

The SQ is a first-in-first-out queue in which the first scan added to the queue is the first scan removed. At the start of the experiment, the only scan stored in the SQ is a $MS^1$ scan. Following an $MS^1$ event, which can be the initial $MS^1$ scan or a subsequent $MS^1$ scan, the top peaks from the $MS^1$ scan are selected and a new scan is created for each selected peak. Each newly created scan is added to the end of the SQ. The $MS^1$ scan itself is then placed at the end of the queue so that the process can repeat itself until the experiment reaches the end time.

In contrast, the rtHeap stores scans in a sorted manner. When new scans are added to the queue, they are positioned within the queue according to their retention time. The scan with the lowest retention time is placed at the front of the queue. When the experiment's retention time exceeds the value in the tp scan in the rtHeap, the top scan is removed and executed immediately. Scans in the rtHeap queue take precedence over, i.e. are executed ahead of, any scans in the SQ. If the rtHeap queue is empty, the system proceeds to the top scan in the SQ. If the SQ scan results in a MS/MS analysis and a new target is identified, the system adds the target to the rtHeap if it is determined that the target is in the current CEO window.

REFERENCES FOR EXAMPLE 3

1. Washburn M P, Wolters D, & Yates J R (2001) Large-scale analysis of the yeast proteome by multidimensional protein identification technology. *Nat Biotechnol* 19:242-247.
2. Nilsson T, et al. (2010) Mass spectrometry in high-throughput proteomics: ready for the big time. *Nat Methods* 7:681-685.
3. Wenger C D, McAlister G C, Xia Q W, & Coon J J (2010) Sub-part-per-million Precursor and Product Mass Accuracy for High-throughput Proteomics on an Electron Transfer Dissociation-enabled Orbitrap Mass Spectrometer. *Mol Cell Proteomics* 9:754-763.
4. Michalski A, et al. (2011) Mass Spectrometry-based Proteomics Using Q Exactive, a High-performance Benchtop Quadrupole Orbitrap Mass Spectrometer. *Mol Cell Proteomics* 10.
5. Eng J K, Mccormack A L, & Yates J R (1994) An Approach to Correlate Tandem Mass-Spectral Data of Peptides with Amino-Acid-Sequences in a Protein Database. *J Am Soc Mass Spectr* 5:976-989.
6. Perkins D N, Pappin D J C, Creasy D M, & Cottrell J S (1999) Probability-based protein identification by searching sequence databases using mass spectrometry data. *Electrophoresis* 20:3551-3567.
7. Geer L Y, et al. (2004) Open mass spectrometry search algorithm. *J Proteome Res* 3:958-964.
8. Liu H B, Sadygov R G, & Yates J R (2004) A model for random sampling and estimation of relative protein abundance in shotgun proteomics. *Anal Chem* 76:4193-4201.
9. Hoopmann M R, Merrihew G E, von Haller P D, & MacCoss M J (2009) Post Analysis Data Acquisition for the Iterative MS/MS Sampling of Proteomics Mixtures. *J Proteome Res* 8:1870-1875.
10. Venable J D, Dong M Q, Wohlschlegel J, Dillin A, & Yates J R (2004) Automated approach for quantitative analysis of complex peptide mixtures from tandem mass spectra. *Nat Methods* 1:39-45.
11. Panchaud A, et al. (2009) Precursor Acquisition Independent From Ion Count: How to Dive Deeper into the Proteomics Ocean. *Anal Chem* 81:6481-6488.
12. McAlister G C, Phanstiel D H, Brumbaugh J, Westphall M S, & Coon J J (2011) Higher-energy Collision-activated Dissociation Without a Dedicated Collision Cell. *Mol Cell Proteomics* 10.
13. Olsen J V, et al. (2007) Higher-energy C-trap dissociation for peptide modification analysis. *Nat Methods* 4:709-712.
14. Syka J E P, Coon J J, Schroeder M J, Shabanowitz J, & Hunt D F (2004) Peptide and protein sequence analysis by electron transfer dissociation mass spectrometry. *P Natl Acad Sci USA* 101:9528-9533.
15. Little D P, Speir J P, Senko M W, Oconnor P B, & Mclafferty F W (1994) Infrared Multiphoton Dissociation of Large Multiply-Charged Ions for Biomolecule Sequencing. *Anal Chem* 66:2809-2815.
16. Olsen J V & Mann M (2004) Improved peptide identification in proteomics by two consecutive stages of mass spectrometric fragmentation. *P Natl Acad Sci USA* 101:13417-13422.
17. Wenger C D, et al. (2011) Gas-phase purification enables accurate, multiplexed proteome quantification with isobaric tagging. *Nat Methods* 8:933-935.
18. Swaney D L, McAlister G C, & Coon J J (2008) Decision tree-driven tandem mass spectrometry for shotgun proteomics. *Nat Methods* 5:959-964.
19. Graumann J, Scheltema R A, Zhang Y, Cox J, & Mann M (2011) A framework for intelligent data acquisition and real-time database searching for shotgun proteomics. *Molecular & cellular proteomics: MCP.*
20. Bailey D J, et al. (2011) How High Mass Accuracy Measurements Will Transform Targeted Proteomics. *Proceedings of the 59th ASMS Conference on Mass Spectrometry and Allied Topics*, (ASMS, Denver, Colo.).
21. Yan W, et al. (2011) Index-ion Triggered MS2 Ion Quantification: A Novel Proteomics Approach for Reproducible Detection and Quantification of Targeted Proteins in Complex Mixtures. *Mol Cell Proteomics* 10.
22. Krokhin O V, et al. (2004) An improved model for prediction of retention times of tryptic peptides in ion pair reversed-phase HPLC—Its application to protein peptide mapping by off-line HPLC-MALDI MS. *Mol Cell Proteomics* 3:908-919.
23. Krokhin O V (2006) Sequence-specific retention calculator. Algorithm for peptide retention prediction in ion-pair RP-HPLC: Application to 300- and 100-angstrom pore size C18 sorbents. *Anal Chem* 78:7785-7795.
24. Kiyonami R, et al. (2011) Increased Selectivity, Analytical Precision, and Throughput in Targeted Proteomics. *Mol Cell Proteomics* 10:-.
25. Schmidt A, et al. (2008) An Integrated, Directed Mass Spectrometric Approach for In-depth Characterization of Complex Peptide Mixtures. *Mol Cell Proteomics* 7:2138-2150.
26. Gruhler A, et al. (2005) Quantitative phosphoproteomics applied to the yeast pheromone signaling pathway. *Mol Cell Proteomics* 4:310-327.
27. Choe L, et al. (2007) 8-Plex quantitation of changes in cerebrospinal fluid protein expression in subjects undergoing intravenous immunoglobulin treatment for Alzheimer's disease. *Proteomics* 7:3651-3660.
28. de Godoy L M F, et al. (2008) Comprehensive mass-spectrometry-based proteome quantification of haploid versus diploid yeast. *Nature* 455:1251-U1260.
29. Xiao K H, et al. (2010) Global phosphorylation analysis of beta-arrestin-mediated signaling downstream of a seven transmembrane receptor (7TMR). *P Natl Acad Sci USA* 107:15299-15304.
30. Phanstiel D H, et al. (2011) Proteomic and phosphoproteomic comparison of human ES and iPS cells. *Nat Methods* 8:821-U884.
31. Lee M V, et al. (2011) A dynamic model of proteome changes reveals new roles for transcript alteration in yeast. *Mol Syst Biol* 7.
32. Bakalarski C E, et al. (2008) The Impact of Peptide Abundance and Dynamic Range on Stable-Isotope-Based Quantitative Proteomic Analyses. *J Proteome Res* 7:4756-4765.
33. Zhang Y, et al. (2010) A Robust Error Model for iTRAQ Quantification Reveals Divergent Signaling between Oncogenic FLT3 Mutants in Acute Myeloid Leukemia. *Mol Cell Proteomics* 9:780-790.
34. Storey J D & Tibshirani R (2003) Statistical significance for genomewide studies. *P Natl Acad Sci USA* 100:9440-9445.
35. Beausoleil S A, Villen J, Gerber S A, Rush J, & Gygi S P (2006) A probability-based approach for high-throughput protein phosphorylation analysis and site localization. *Nat Biotechnol* 24:1285-1292.
36. Schroeder M J, Shabanowitz J, Schwartz J C, Hunt D F, & Coon J J (2004) A neutral loss activation method for improved phosphopeptide sequence analysis by quadrupole ion trap mass spectrometry. *Anal Chem* 76:3590-3598.
37. Picotti P, et al. (2010) High-throughput generation of selected reaction-monitoring assays for proteins and proteomes. *Nat Methods* 7:43-U45.
38. Wenger C D, Phanstiel D H, Lee M V, Bailey D J, & Coon J J (2011) COMPASS: A suite of pre- and post-search proteomics software tools for OMSSA. *Proteomics* 11:1064-1074.
39. Kersey P J, et al. (2004) The International Protein Index: An integrated database for proteomics experiments. *Proteomics* 4:1985-1988.

STATEMENTS REGARDING INCORPORATION BY REFERENCE AND VARIATIONS

Each reference cited herein is hereby incorporated by reference in its entirety. However, if any inconsistency arises between a cited reference and the present disclosure, the present disclosure takes precedent. Some references provided herein are incorporated by reference to provide details concerning the state of the art prior to the filing of this application, other references can be cited to provide additional or alternative device elements, additional or alternative materials, additional or alternative methods of analysis or applications of the invention. Patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

U.S. Provisional Patent Application No. 61/471,464, filed Apr. 4, 2011, is hereby incorporated by reference in its entirety to the extent not inconsistent with the present description.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, methods steps set forth in the present description. As will be clear to one of skill in the art, methods and devices useful for the present methods can include a large number of optional composition and processing elements and steps.

One of ordinary skill in the art will appreciate that device elements, as well as materials, shapes and dimensions of device elements, as well as methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention.

When a Markush group or other grouping is used herein, all individual members of the group and all combinations and possible subcombinations of the group are intended to be individually included in the disclosure. Every combination of components or materials described or exemplified herein can be used to practice the invention, unless otherwise stated. One of ordinary skill in the art will appreciate that methods, device elements, and materials other than those specifically exemplified can be employed in the practice of the invention without resort to undue experimentation. All art-known functional equivalents, of any such methods, device elements, and materials are intended to be included in this invention. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this invention. The invention illustratively described herein suitably can be practiced in the absence of any element or elements, limitation or limitations which is not specifically disclosed herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The term "comprising" is intended to be broader than the terms "consisting essentially of" and "consisting of", however, the term "comprising" as used herein in its broadest sense is intended to encompass the narrower terms "consisting essentially of" and "consisting of:", thus the term "comprising" can be replaced with "consisting essentially of" to exclude steps that do not materially affect the basic and novel characteristics of the claims and "comprising" can be replaced with "consisting of" to exclude not recited claim elements.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims.

Although the description herein contains many specifics, these should not be construed as limiting the scope of the invention, but as merely providing illustrations of some of the embodiments of the invention.

What is claimed is:

1. A method of identifying or quantifying an analyte in a sample using mass spectrometry, the method comprising:
   (a) providing a list of target analytes and target analyte product information, wherein the list comprises from 25 to 5,000,000 target analytes;
   (b) providing a sample containing an analyte;
   (c) generating a distribution of precursor analyte ions from the sample;
   (d) fragmenting precursor analyte ions having a preselected distribution of mass-to-charge ratios, thereby generating product ions;
   (e) measuring mass-to-charge ratios of at least a portion of the product ions in a mass analyzer, wherein the mass analyzer has a mass accuracy of at least 1000 ppm, thereby generating product ion mass spectrometry data;
   (f) optimizing analyte identification or quantitation during data acquisition by comparing the product ion mass spectrometry data to the list of target analytes and target analyte product information;
   (g) calculating a chromatography column elution order of the analyte in the list of target analytes and target analyte product information, thereby generating an elution order list;
   (h) sorting the elution order list from first eluting analyte to last eluting analyte, thereby generating a sorted elution order list;
   (i) fractionating the sample with a chromatography column prior to generating a distribution of precursor analyte ions from the sample;
   (j) identifying target analyte product information in the product ion mass spectrometry data corresponding to a target analyte, thereby identifying a target analyte;
   (k) comparing the identified target analyte to the sorted elution order list during data acquisition; and
   (l) identifying one or more target analytes from the sorted elution order list which are within X analytes of the identified analyte, wherein X is equal to 20% of the total number of target analytes in the elution order list,
   thereby identifying or quantifying an analyte in the sample using mass spectrometry.

2. The method of claim 1, wherein:
   the list of target analytes and target analyte product information comprises target peptides and target peptide product information corresponding to one or more proteins;
   the analyte comprises peptides corresponding to proteins;
   the step of (d) fragmenting precursor analyte ions having a preselected distribution of mass-to-charge ratios, thereby generating product ions; comprises fragmenting precursor peptide ions having a preselected distribution of mass-to-charge ratios, thereby generating product ions; and
   the step of (f) optimizing analyte identification or quantitation during data acquisition by comparing the product ion mass spectrometry data to the list of target analytes and target analyte product information; comprises optimizing peptide or protein identification or quantitation during data acquisition by comparing the product ion mass spectrometry data to the list of target analytes and target analyte product information comprising target peptides and target peptide product information corresponding to one or more proteins.

3. The method of claim 2, further comprising:
   identifying target peptides or peptide product information in the product ion mass spectrometry data corresponding to a target peptide, thereby identifying a target peptide; and
   removing the identified target peptide or peptide product information from the list of target peptides and target peptide product information corresponding to one or more proteins during data acquisition.

4. The method of claim 2, further comprising:
   selecting a target peptide having one or more sites of post-translational modification;
   comparing the product ion mass spectrometry data to the list of target peptides and target peptide products corresponding to one or more proteins to determine if the sites of the target peptide having one or more post-translational modifications can be uniquely identified; and
   adjusting a fragmentation parameter during data acquisition until sites of the target peptide having the one or more post-translational modifications can be uniquely identified;
   wherein the fragmentation parameter corresponds to a fragmentation pressure, gas, electron energy, wavelength of electromagnetic radiation, power of electromagnetic radiation, illumination time of electromagnetic radiation, flux of electromagnetic radiation, total dose of electromagnetic radiation, collision energy, or reaction time.

5. The method of claim 1, further comprising:
   identifying one or more analytes in the list of next predicted eluting analytes during data acquisition;
   selecting a range of mass-to-charge ratios of precursor ions corresponding to the one or more analytes in the list of next predicted eluting analytes; and
   measuring the mass-to-charge ratios of the range of mass-to-charge ratios corresponding to the one or more analytes in the list of next predicted eluting analytes,
   thereby generating precursor mass spectrometry data.

6. The method of claim 1, further comprising:
   identifying one or more analytes in the list of next predicted eluting analytes during data acquisition;
   wherein in step (d), the precursor analyte ions having a preselected distribution of mass-to-charge ratios correspond to the one or more analytes in the list of next predicted eluting analytes.

7. The method of claim 1, further comprising:
   identifying one or more analytes in the list of next predicted eluting analytes during data acquisition;
   selecting a range of mass-to-charge ratios of precursor ions corresponding to the one or more analytes in the list of next predicted eluting analytes;
   fragmenting precursor ions having mass-to-charge ratios within the selected range of mass-to-charge ratios; and
   measuring the mass-to-charge ratios of the fragmented precursor ions, thereby generating product ion mass spectrometry data.

8. The method of claim 1, wherein the mass-to-charge ratios of multiple product ions are measure simultaneously.

9. The method of claim 1, wherein the multiple product ions are generated from different precursor analyte ions.

10. The method of claim 1 further comprising:
    measuring mass-to-charge ratios of at least a portion of the distribution of precursor analyte ions, thereby generating precursor analyte ion mass spectrometry data; and
    optimizing analyte identification or quantitation during data acquisition by comparing the precursor analyte ion mass spectrometry data to the list of target analytes and target analyte product information, wherein said list further comprises target analyte precursor ion information and landmark precursor ion signal information.

11. The method of claim 1 further comprising:
measuring the mass-to-charge ratios of a range of mass-to-charge ratios corresponding to the distribution of precursor analyte ions, thereby generating precursor mass spectrometry data;
determining a signal-to-noise ratio of two or more peaks in the precursor mass spectrometry data corresponding to one or more analytes in the list of target analytes and target analyte products, during data acquisition;
wherein at least one of the two or more peaks in the precursor mass spectrometry data corresponding to one or more analytes corresponds to a labeled analyte and at least one corresponds to an un-labeled analyte; and
repeating steps (c)-(f) if the signal-to-noise ratio of the least intense of the two or more peaks in the precursor mass spectrometry data corresponding to one or more analytes in the list of target analytes and target analyte products is less than two-to-one.

12. A mass spectrometer system for analyzing an analyte in a sample, the system comprising:
an ion source for generating ions from the analyte;
first ion separation optics in communication with the ion source for separating ions according to their mass-to-charge ratios;
ion fragmentation optics in communication with the first ion separation optics for generating product ions;
a mass analyzer in communication with the ion fragmentation optics for separating ions according to their mass-to-charge ratios; wherein the mass analyzer comprises an ion detector for detecting ions separated according to their mass-to-charge ratios;
a controller operably connected to the first and second ion separation optics, the first ion detector, and the ion fragmentation optics; wherein the controller comprises a memory module; and
a chromatography column in communication with the ion source for fractionating the sample,
wherein the controller controls the memory module, ion optics, mass analyzer and detector so as to:
(a) receive a list of target analytes and target analyte product information into the memory module, wherein the list comprises from 25 to 5,000,000 target analytes;
(b) provide a sample containing an analyte;
(c) generate a distribution of precursor analyte ions from the sample;
(d) fragment precursor analyte ions having a preselected distribution of mass-to-charge ratios, thereby generating product ions;
(e) measure the mass-to-charge ratios of at least a portion of the product ions in the mass analyzer, wherein the mass analyzer has a mass accuracy of at least 1000 ppm, thereby generating product ion mass spectrometry data;
(f) optimize analyte identification or quantitation during data acquisition by comparing the product ion mass spectrometry data to the list of target analytes and target analyte product information;
(g) calculate a chromatography column elution order of the peptides in the list of target peptides and target peptide product information corresponding to one or more proteins, thereby generating an elution order list;
(h) sort the elution order list from first eluting peptide to last eluting peptide, thereby generating a sorted elution order list;
(i) fractionate the sample with the chromatography column prior to generating a distribution of precursor peptide ions from the sample;
(j) identify target peptide product information in the product ion mass spectrometry data corresponding to a target peptide, thereby identifying a target peptide;
(k) compare the identified target peptide to the sorted elution order list during data acquisition; and
(l) identify one or more target peptides from the sorted elution order list which are within X peptides of the identified Peptide, wherein X is equal to 20% of the total number of target peptides in the elution order list, thereby generating a list of next predicted eluting peptides.

13. The system of claim 12, wherein the controller further controls the memory module, ion optics, mass analyzer, chromatography column and detector so as to:
identify one or more peptides in the list of next predicted eluting peptides during data acquisition;
select a range of mass-to-charge ratios of precursor ions corresponding to the one or more peptides in the list of next predicted eluting peptides; and
measure the mass-to-charge ratios of the range of mass-to-charge ratios corresponding to the one or more peptides in the list of next predicted eluting peptides, thereby generating precursor mass spectrometry data.

14. The system of claim 12, wherein the controller further controls the memory module, ion optics, mass analyzer, chromatography column and detector so as to:
identify one or more peptides in the list of next predicted eluting peptides during data acquisition;
wherein in step (d), the precursor peptide ions having a preselected distribution of mass-to-charge ratios correspond to the one or more peptides in the list of next predicted eluting peptides.

15. The system of claim 14, wherein the controller further controls the memory module, ion optics, mass analyzer and detector so as to:
identify target analyte product information in the product ion mass spectrometry data corresponding to a target analyte, thereby identifying a target analyte; and
remove the identified target analyte from the list of target analytes and target analyte product information during data acquisition.

16. The system of claim 12, wherein the controller further controls the memory module, ion optics, mass analyzer and detector so as to: add target analytes and target analyte product information to the list of target analytes and target analyte product information during data acquisition.

17. The system of claim 12, wherein the controller controls the memory module, ion optics, mass analyzer and detector so as to measure the mass-to-charge ratios of multiple product ions simultaneously.

18. The system of claim 12, wherein the controller controls the memory module, ion optics, mass analyzer and detector so as to fragment multiple precursor analyte ions to generate product ions, wherein the mass-to-charge ratios of the product ions generated from the multiple precursor analyte ions are measured simultaneously.

19. A method of identifying or quantifying an analyte in a sample using mass spectrometry, the method comprising:
(a) providing a list of target peptides, wherein the target list comprises from 25 to 5,000,000 target peptides;
(b) calculating a chromatography column elution order and elution time of the peptides in the list of target peptides, thereby generating an elution order list and predicted elution times for each target peptide;

(c) sorting the elution order list from first eluting peptide to last eluting peptide, thereby generating a sorted elution order list;
(d) providing a sample containing an analyte, wherein said analyte comprises peptides corresponding to one or more proteins;
(e) generating a distribution of precursor analyte ions from the sample at elution times corresponding to the predicted elution times for the target peptides, wherein said analyte ions comprises peptide ions;
(f) fragmenting precursor analyte ions having a preselected distribution of mass-to-charge ratios from at least a portion of the distribution of precursor analyte ions, thereby generating product ions;
(g) measuring the mass-to-charge ratios of at least a portion of the product ions collected in a mass analyzer, wherein the mass analyzer has a mass accuracy of at least 1000 ppm, thereby generating product ion mass spectrometry data; and
(h) identifying target peptides or peptide product information in the product ion mass spectrometry data corresponding to a target peptide by comparing the product ion mass spectrometry data to the list of target peptides and target peptide product information,
thereby identifying or quantifying an analyte in the sample using mass spectrometry.

20. The method of claim 19 further comprising performing one or more data dependent acquisition scans comprising:
generating a second distribution of precursor analyte ions from the sample, wherein the elution times of the second distribution of precursor analyte ions do not correlate to the predicted elution times for the target peptides;
fragmenting precursor analyte ions from at least a portion of the second distribution of precursor analyte ions, thereby generating a second set of product ions; and
measuring the mass-to-charge ratios of the second set of product ions, thereby generating data dependent product ion mass spectrometry data.

21. The method of claim 20 further comprising:
(i) identifying one or more peptides in the sorted elution list as peptides predicted to elute next during data acquisition;
(j) selecting a range of mass-to-charge ratios of precursor ions corresponding to the one or more peptides predicted to elute next; and
(k) measuring the mass-to-charge ratios of the range of mass-to-charge ratios corresponding to the one or more peptides predicted to elute next, thereby generating precursor mass spectrometry data.

* * * * *